United States Patent [19]
Diamond et al.

[11] Patent Number: 5,877,295
[45] Date of Patent: Mar. 2, 1999

[54] ANTIBODIES WHICH BIND A SUBPOPULATION OF MAC-1 (CD11B/CD18) MOLECULES WHICH MEDIATE NEUTROPHIL ADHESION TO ICAM-1 AND FIBRINOGEN

[75] Inventors: Michael Diamond, Cambridge; Timothy A. Springer, Chestnut Hill, both of Mass.

[73] Assignee: The Center for Blood Research, Boston, Mass.

[21] Appl. No.: 517,589

[22] Filed: Aug. 22, 1995

Related U.S. Application Data

[63] Continuation of Ser. No. 964,156, Oct. 22, 1992, abandoned, which is a continuation-in-part of Ser. No. 953,904, Sep. 30, 1992, abandoned.

[51] Int. Cl.⁶ .............................. C07K 16/28; C12N 5/12
[52] U.S. Cl. .................................. 530/387.73; 530/387.1; 530/388.1; 530/388.2; 530/388.22; 530/388.7; 530/389.6; 435/326; 435/332; 435/334; 435/343; 435/343.1
[58] Field of Search .............................. 530/387.1, 388.1, 530/388.7, 389.6, 388.22, 388.23; 435/70.21, 325, 326, 343.4, 172.2, 332, 334, 343.2, 343, 346

[56] References Cited

PUBLICATIONS

Diamond et al. J. Cell Biol. 120: 1031–1043 (1993).
Harris et al. Tibtech 11: 42–46 (1993).
Diamond et al. J. Cell Biology 120: 545–556 (1993).
Diamond et al. In Leukocyte Typing: IV (Ed; Knapp del.) Oxford, 1989 pp. 570–574.
Diamond et al. J. Cell Biology 111: 3129–3139 (1990).
Altieri et al. J. Immunol. 141: 2656–2660 (1988).
Stacker et al. J. Immunol. 146: 648–655 (1991).
Altieri, D.C. et al., Oligospecificity of the Cellular Adhesion Receptor MAC–1 Encompasses an Inducible Recognition Specificity for Fibrinogen, *J. Cell. Biol.* 107:1893–1900 (Nov. 1988).
Altieri, D.C. et al., The Saturable High Affinity Association of Factor X to ADP–stimulated Monocytes Defines a Novel Function of the Mac–1 Receptor, *J. Biol. Chem.* 263(15):7007–7015 (May 25, 1988).
Altieri, D.C. et al., A Unique Recognition Site Mediates the Interaction of Fibrinogen with the Leukocyte Integrin Mac–1 (CD11b/CD18), *J. Biol. Chem.* 265(21):12119–12122 (Jul. 25, 1990).
Altieri, D.C., Occupancy of CD11b/CD18 (Mac–1) Divalent Ion Binding Site(s) Induces, Leukocyte Adhesion, *J. Immunol.* 147(6):1891–1898 (Sep. 15, 1991).
Anderson, D.C. et al., Leukocyte Adhesion Deficiency: An Inherited Defect in the Mac–1, LFA–1, and p150,95 Glycoproteins, *Ann. Rev. Med.* 38:175–194 (1987).
Anderson, D.C. et al., Contributions Of The Mac–1 Glycoprotein Family To Adherence–Dependent Granulocyte Functions: Structure–Function Assessments Employing Subunit–Specific Monoclonal Antibodies, *J. Immunol.* 137:15–27 (Jul. 1, 1986).

Anderson, D.C. et al., Impaired Transendothelial Migration by Neonatal Neutrophils: Abnormalities of Mac–1 (CD11b/CD18)–Dependent Adherence Reactions, *Blood* 76(12):2613–2621 (Dec. 15, 1990).
Arnaout, M.A. et al., Amino Acid Sequence of the Alpha Subunit of Human Leukocyte Adhesion Receptor Mo1 (Complement Receptor Type 3), *J. Cell Biol.* 106:2153–2158 (Jun. 1988).
Beller, D.I. et al., Anti–Mac–1 Selectively Inhibits The Mouse And Human Type Three Complement Receptor, *J. Exper. Med.* 156:1000–1009 (Oct. 1982).
Berger, M. et al., Human Neutrophils Increase Expression of C3bi as well as C3b Receptors Upon Activation, *J. Clin. Invest.* 74:1566–1571 (Nov. 1984).
Bullock, W.E. et al., Role Of The Adherence–Promoting Receptors, CR3, LFA–1 And p150,95 In Binding Of *Histoplasma Capsulatum* By Human Macrophages, *J. Exper. Med.* 165:195–210 (Jan. 1987).
Butcher, E.C., Cellular and Molecular Mechanisms That Direct Leukocyte Traffic, *Amer. J. Pathol.* 136(1):3–11 (Jan. 1990).
Buyon, J.P. et al., Dissociation Between Increased Surface Expression Of Gp165/95 And Homotypic Neutrophil Aggregation, *J. Immunol.* 140(9):3156–3160 (May 1, 1988).
Coller, B.S., A New Murine Monoclonal Antibody Reports an Activation–dependent Change in the Conformation and/or Microenvironment of the Platelet Glycoprotein IIb/IIIa Complex, *J. Clin. Invest.* 76:101–108 (Jul. 1985).
Corbi, A.L. et al., cDNA cloning and complete primary structure of the α subunit of a leukocyte adhesion glycoprotein, p150,95, *EMBO J.* 6(13):4023–4028 (1987).
Corbi, A.L. et al., The Human Leukocyte Adhesion Glycoprotein Mac–1 (Complement Receptor Type 3, CD11b) α Subunit, *J. Biol. Chem.* 263(25):12403–12411 (Sep. 1988).
D'Souza, S.E. et al., A discrete sequence in a platelet integrin is involved in ligand recognition, *Nature* 350:66–68 (Mar. 7, 1991).
D'Souza, S.E. et al., Localization of an Arg–Gly–Asp Recognition Site Within an Integrin Adhesion Receptor, *Science* 242:91–93 (Oct. 7, 1988).
D'Souza, S.E. et al., The Ligand Binding Site of the Platelet Integrin Receptor GPIIb–IIIa Is Proximal to the Second Calcium Binding Domain of Its α Subunit, *J. Biol. Chem.* 265(6):3440–3446 (Feb. 25, 1990).

(List continued on next page.)

*Primary Examiner*—Lila Feisee
*Assistant Examiner*—Phillip Gambel

[57] ABSTRACT

The present invention is based on the novel observation that upon stimulation of resting myeloid cells, not all of the Mac-1 molecules expressed by the cell become activated. Only select subpopulations of Mac-1 molecules are activated and become capable of binding ligand. Further, the activated Mac-1 molecules were found to possess activation specific epitopes which distinguishes them from non-activated Mac-1 molecules. Based on these observations antibodies are described which selectively bind activated Mac-1 molecules but are substantially incapable of binding non-activated Mac-1.

5 Claims, 39 Drawing Sheets

OTHER PUBLICATIONS

Dana, N. et al., Two Functional Domains In The Phagocyte Membrane Glycoprotein Mo1 Identified With Monoclonal Antibodies, *J. Immunol. 137*:3259–3263 (Nov. 15, 1986).

Davignon, D. et al., Lymphocyte function–associated antigen 1 (LFA–1): A surface antigen distinct from Lyt–2,3 that participates in T lymphocyte–mediated killing, *Proc. Natl. Acad. Sci. USA 78*:4535–4539 (Jul. 1981).

Detmers, P.A. et al., Aggregation of Complement Receptors on Human Neutrophils in the Absence of Ligand, *J. Cell Biol. 105*:1137–1145 (1987).

Detmers, P.A. et al., Neutrophil–Activating Protein 1/Interleukin 8 Stimulates The Binding Activity Of The Leukocyte Adhesion Receptor CD11b/CD18 On Human Neutrophils, *J. Exp. Med. 171*:1155–1162 (Apr. 1990).

Yancey, K.B. et al., Human C5a Modulates Monocyte Fc and C3 Receptor Expression, *J. Immunol. 135*:465–470 (Jul. 1985).

Diamond, M.S. et al., Binding of the Integrin Mac–1 (CD11b/CD18) to the Third Immunoglobulin–like Domain of ICAM–1 (CD54) and Its Regulation by Glycosylation, *Cell 65*:961–971 (Jun. 14, 1991).

Dransfield, I. et al., Regulated Expression of $Mg^{2+}$ binding epitope leukocyte integrin $\alpha$ subunits, *EMBO J. 8(12)*:3759–3765 (1989).

Dransfield, I. et al., Divalent Cation Regulation of the Function of the Leukocyte Integrin LFA–1, *J. Cell Biol. 116(1)*:219–226 (Jan. 1992).

Dreyer, W.J. et al., Neutrophil Accumulation in Ischemic Canine Myocardium: Insights Into Time Course, Distribution, and Mechanism of Localization During Early Reperfusion, *Circulation 84(1)*:400–411 (Jul. 1991).

Dustin, M.L. et al., Lymphocyte Function–associated Antigen–1 (LFA–1) Interaction with Intercellular Adhesion Molecule–1 (ICAM–1) is One of At Least Three Mechanisms for Lymphocyte Adhesion to Cultured Endothelial Cells, *J. Cell Biol. 107*:321–331 (Jul. 1988).

Dustin, M.L. et al., T–cell receptor cross–linking transiently stimulates adhesiveness through LFA–1, *Nature 341*:619–624 (Oct. 19, 1989).

Falanga, P.B. et al., Late Treatment with anti–LFA–1 (CD11a) antibody prevents cerebral malaria in a mouse model, *Eur. J. Immunol. 21*:2259–2263 (1991).

Fischer, A. et al., Prevention Of Graft Failure By An Anti–HLFA–1 Monoclonal Antibody In HLA–Mismatched Bone–Marrow Transplantation, *Lancet 2*:1058–1061 (Nov. 8, 1986).

Griffin, J.D. et al., Expression of Myeloid Differentiation Antigens on Normal and Malignant Myeloid Cells, *J. Clin. Invest. 68*:932–941 (Oct. 1981).

Harlan, J.M. et al., The Role of Neutrophil Membrane Glycoprotein GP–150 in Neutrophil Adherence to Endothelium In Vitro, *Blood 66*:167–178 (Jul. 1985).

Haskard, D. et al., T Lymphocyte Adhesion To Endothelial Cells: Mechanisms Demonstrated By Anti–LFA–1 Monoclonal Antibodies, *J. Immunol. 137*:2901–2906 (Nov. 1986).

Hemler, M.E., VLA Proteins In The Integrin Family: Structures, Functions, and Their Role on Leukocytes, *Annu. Rev. Immunol. 8*:365–400 (1990).

Hibbs, M.L. et al., Regulation of Adhesion to ICAM–1 by the Cytoplasmic Domain of LFA–2 Integrin β Subunit, *Science 251*:1611–1613 (Mar. 29, 1991).

Hogg, N. et al., The p150,95 molecule is a marker of human mononuclear phagocytes: comparison with expression of class II molecules, *Eur. J. Immunol. 16*:240–248 (1986).

Hynes, R.O., Integrins: A Family of Cell Surface Receptors, *Cell 48*:549–554 (Feb. 27, 1987).

Hynes, R.O., Integrins: Versatility, Modulation, and Signaling in Cell Adhesion, *Cell 69*:11–25 (Apr. 3, 1992).

International Search Report for International Application No. PCT/US93/09777, filed Oct. 12, 1993.

Kaufman, Y. et al., Cloning Of The Murine Lymphocyte Function–Associated Molecule–1 $\alpha$–Subunit And Its Expression In Cos Cells, *J. Immunol. 147(1)*:369–371 (Jul. 1, 1991).

Keizer, G.D. et al., Membrane Glycoprotein p150,95 Of Human Cytotoxic T Cell Clones Is Involved In Conjugate Formation With Target Cells, *J. Immunol. 138*:3130–3136 (May 15, 1987).

Keizer, G.D. et al., Role of p150,95 in adhesion, migration, chemotaxis and phagocytosis of human monocytes, *Eur. J. Immunol. 17*:1317–1322 (1987).

Keizer, G.D. et al., A Monoclonal Antibody (NKI–L16) Directed Against A Unique Epitope On The $\alpha$–Chain Of Human Leukocyte Function–Associated Antigen 1 Induces Homotypic Cell–Cell Interactions, *J. Immunol. 140(5)*:1393–1400 (Mar. 1, 1988).

Kishimoto, T.K. et al., The Leukocyte Integrins, *Adv. Immunol. 46*:149–182 (1989).

Krensky, A.M. et al., The Functional Significance, Distribution, And Structure of LFA–1, LFA–2, And LFA–3: Cell Surface Antigens Associated With CTL–Target Interactions, *J. Immunol. 131(2)*:611–616 (Aug. 1983).

Lanier, L.L. et al., p150/95, Third member of the LFA–1/$Cr_3$ polypeptide family identified by anti–Leu M5 monoclonal antibody, *Eur. J. Immunol. 15*:713–718 (1985).

Larson, R.S. et al., Primary Structure of the Leukocyte Function–associated Molecule–1 $\alpha$ Subunit: an Integrin with an Embedded Domain Defining a Protein Superfamily, *J. Cell Biol. 108*:703–712 (Feb. 1989).

Larson, R.S. et al., The leukocyte integrin LFA–1 reconstituted by cDNA transfection in a nonhematopoietic cell line is functionally active and not transiently regulated, *Cell Reg. 1*:359–367 (Mar. 1990).

Lawrence, M.B. et al., Leukocytes Roll on a Selectin at Physiologic Flow Rates: Distinction from and Prerequisite for Adhesion through Integrins, *Cell 65*:859–873 (May 31, 1991).

Lindbom, L. et al., Rabbit Leukocyte Adhesion Molecules CD11/CD18 and Their Participation in Acute and Delayed Inflammatory Responses and Leukocyte Distribution in Vivo, *Clin. Immunol. Immunopathol. 57*:105–119 (1990).

Lo, S.K. et al., Transient Adhesion of Neutrophils to Endothelium, *J. Exp. Med. 169*:1779–1793 (May 1989).

Lo, S.K. et al., Two Leukocyte Receptors (CD11a/CD18 and CD11b/CD18) Mediate Transient Adhesion To Endothelium By Binding To Different Ligands, *J. Immunol. 143(10)*:3325–3329 (Nov. 15, 1989).

Loftus, J.C. et al., A $\beta_3$ Integrin Mutation Abolishes Ligand Binding and Alters Divalent Cation–Dependent Conformation, *Science 249*:915–918 (Aug. 24, 1990).

Micklem, K.J. et al., Isolation of complement–fragment–iC3b–binding proteins by affinity chromatography: The identification of p150,95 as an iC3b–binding protein, *Biochem. J. 231*:233–236 (1985).

Mileski, W.J. et al., Inhibition of CD18–dependent neutrophil adherence reduces organ injury after hemorrhagic shock in primates, *Surgery 108(2)*:206–212 (Aug. 1990).

Miller, L.J. et al., Regulated Expression Of The Mac–1, LFA–1, p150,95 Glycoprotein Family During Leukocyte Differentiation, *J. Immunol. 137*:2891–2900 (Nov. 1, 1986).

Miller, L.J. et al., Stimulated Mobilization of Monocyte Mac–1 and p150,95 Adhesion Proteins from an Intracellular Vesicular Compartment to the Cell Surface, *J. Clin. Invest. 80*:535–544 (Aug. 1987).

Mosser, D.M. et al., The Mouse Macrophage Receptor For C3bi (CR3) Is A Major Mechanism In The Phagocytosis Of Leishmania Promastigotes, *J. Immunol.* 135:2785–2789 (Oct. 1985).

Patarroyo, M. et al., Leukocyte Adhesion to Cells: Molecular Basis, Physiological Relevance, and Abnormalities, *Scan J. Immunol.* 30:129–164 (1989).

Perez, N. et al., In vivo infusion of anti LFA–1 antibody in HLA non–identical bone marrow transplantation in children: serum concentrations and biological effects, *Bone Marrow Transp.* 4:379 (1989).

Philips, M.R. et al., Up–regulation of the iC3b Receptor (CR3) is Neither Necessary Nor Sufficient to Promote Neutrophil Aggregation, *J. Clin. Invest.* 82:495–501 (1988).

Pytela, R., Amino acid sequence of the murine Mac–1 α chain reveals homology with the integrin family and an additional domain related to von Willebrand factor, *EMBO J.* 7:1371–1378 (1988).

Robinson, M.K. et al., Antibody Against The Leu–Cam β–Chain (CD18) Promotes Both LFA–1– And CR3–Dependent Adhesion Events *J. Immunol.* 148(4):1080–1085 (Feb. 15, 1992).

Rosen, H. et al., Monoclonal Antibody To The Murine Type 3 Complement Receptor Inhibits Adhesion Of Myelomonocytic Cells In Vitro And Inflammatory Cell Recruitment In Vivo, *J. Exp. Med.* 166:1685–1701 (Dec. 1987).

Rosen, H. et al., Antibody To The Murine Type 3 Complement Receptor Inhibits T Lymphocyte–Dependent Recruitment Of Myelomonocytic Cells In Vivo, *J. Exp. Med.* 169:535–548 (Feb. 1989).

Ross, G.D. et al., Macrophage cytoskeleton association with CR3 and CR4 regulates receptor mobility and phagocytosis of iC3b–opsonized erythrocytes, *J. Leukoc. Biol.* 51:109–117 (Feb. 1992).

Sanchez–Madrid, F. et al., Three distinct antigens associated with human T–lymphocyte–mediated cytolosis: LFA–1, LFA–2, and LFA–3, *Proc. Natl. Acad. Sci. USA* 79:7489–7493 (Dec. 1982).

Schleiffenbaum, B. et al., The Cell Surface Glycoprotein Mac–1 (CD11b/CD18) Mediates Neutrophil Adhesion And Modulates Degranulation Independently Of Its Quantitative Cell Surface Expression, *J. Immunol.* 142(10):3537–3545 (May 15, 1989).

Simpson, P.J. et al., Sustained Limitation of Myocardial Reperfusion Injury by a Monoclonal Antibody That Alters Leukocyte Function, *Circulation* 81(1):226–237 (Jan. 1990).

Simpson, P.J. et al., Reduction of Experimental Canine Myocardial Reperfusion Injury by a Monoclonal Antibody (Anti–Mo1, Anti–CD11b) That Inhibits Leukocyte Adhesion, *J. Clin. Invest.* 81:624–629 (Feb. 1988).

Smith, C.W. et al., Cooperative Interactions of LFA–1 and Mac–1 with Intercellular Adhesion Molecule–1 in Facilitating Adherence and Transendothelial Migration of Human Neutrophils In Vitro, *J. Clin. Invest.* 83:2008–2017 (Jun. 1989).

Smith, C.W. et al., Recognition of an Endothelial Determinant for CD–18–dependent Human Neutrophil Adherence and Transendothelial Migration, *J. Clin. Invest.* 82:1746–1756 (Nov. 1988).

Smith, J.W. et al., The Arg–Gly–Asp Binding Domain of the Vitronectin Receptor, *J. Biol. Chem.* 263(35):18726–18731 (Dec. 15, 1988).

Springer, et al., The importance of the Mac–1, LFA–1 glycoprotein family in monocyte and granulocyte adherence, chemotaxis, and migration into inflammatory sites: insights from an experiment of nature, in *Biochemistry of Macrophages* (CIBA Foundation Symposium 118), Pitman, London, pp. 102–126 (1986).

Springer, T.A., Adhesion receptors of the immune system, *Nature* 346:425–433 (Aug. 2, 1990).

Springer, T.A. et al., Sticky sugars for selectins, *Nature* 349:196–197 (Jan. 17, 1991).

Staunton, D.E. et al., The Arrangement of the Immunoglobulin–like Domains of ICAM–1 and the Binding Sites for LFA–1 and Rhinovirus, *Cell* 61:243–254 (Apr. 20, 1990).

Taniguchi–Sidle, A. et al., Mutagenesis of the Arg–Gly–Asp Triplet in Human Complement Component C3 Does Not Abolish Binding of iC3b to the Leukocyte Integrin Complement Receptor Type III (CR3, CD11b/CD18) *J. Biol. Chem.* 267(1):635–643 (Jan. 5, 1992).

Todd, R.F. et al., Subcellular Localization of the Large Subunit of Mo1 (Mo1α; formerly gp110), a Surface Glycoprotein Associated with Neutrophil Adhesion, *J. Clin. Invest.* 74:1280–1290 (Oct. 1984).

Uciechowski et al., Cluster Report: CD11, in *Leukocyte Typing IV: White Cell Differentiation Antigens,* Knapp, ed., Oxford University Press, Oxford, England, pp. 543–551 (1989).

van Kooyk, Y. et al., Activation of LFA–1 through a $Ca^{2+}$–dependent Epitope Stimulates Lymphocyte Adhesion, *J. Cell Biol.* 112(2):345–354 (Jan. 1991).

van Kooyk, Y. et al., Enhancement of LFA–1–mediated cell adhesion by triggering through CD2 or CD3 on T lymphocytes, *Nature* 342:811–813 (Dec. 14, 1989).

Vedder, N.B. et al., Increased Surface Expression of CD11b–CD18 (Mac–1) Is Not Required for Stimulated Neutrophil Adherence to Cultured Endothelium, *J. Clin. Invest.* 81:676–682 (Mar. 1988).

Vedder, N.B. et al., A Monoclonal Antibody to the Adherence–promoting Leukocyte Glycoprotein, CD18, Reduces Organ Injury and Improves Survival from Hemorrhagic Shock and Resuscitation in Rabbits, *J. Clin. Invest.* 81:939–944 (Mar. 1988).

Wegner, C.D. et al., Expression and Probable Roles of Cell Adhesion Molecules in Lung Inflammation, *Chest* 101(3 Suppl.):34S–39S (Mar. 1992).

Wright, S.D. et al., Phorbol Esters Cause Sequential Activation And Deactivation Of Complement Receptors On Polymorphonuclear Leukocytes, *J. Immunol.* 136(5):1759–1764 (Mar. 1, 1986).

Wright, S.D. et al., C3bi receptor (complement receptor type 3) recognizes a region of complement protein C3 containing the sequence Arg–Gly–Asp, *Proc. Natl. Acad. Sci. USA* 84:1965–1968 (Apr. 1987).

Wright, S.D. et al., Complement receptor type three (CD11b/CD18) of human polymorphonuclear leukocytes recognizes fibrinogen, *Proc. Natl. Acad. Sci. USA* 85:7734–7738 (Oct. 1988).

Wright, S.D. et al., CR3 (CD11b/CD18) Expresses One Binding Site for Arg–Gly–Asp–Containing Peptides And A Second Site for Bacterial Lipopolysaccharide, *J. Exp. Med.* 169:175–183 (Jan. 1989).

Wright, S.D. et al., Identification of the C3bi receptor of human monocytes and macrophages by using monoclonal antibodies, *Proc. Natl. Acad. Sci. USA* 80:5699–5703 (Sep. 1983).

FIG. 15A

| mAb | Epitope | Isotype | Mac-1 | p150.95 | M-e-X | X-e-M | M-b-X | X-b-M | M-a-X | X-a-M | M-e-X-b-M | X-e-M-b-X | M-b-X-a-M | X-b-M-a-X |
|---|---|---|---|---|---|---|---|---|---|---|---|---|---|---|
| LPM19c | I domain | G2a | ‡‡ | – | – | ‡‡ | ‡‡ | – | ‡‡ | – | – | ‡‡ | ‡‡ | – |
| OKM9 | I domain | G1 | ‡‡ | – | – | ‡‡ | ‡‡ | – | ‡‡ | – | – | ‡‡ | ‡‡ | – |
| LM2/1 | I domain | G1 | ‡‡ | – | – | ‡‡ | ‡‡ | – | ‡‡ | – | – | ‡‡ | ‡‡ | – |
| TMG-65 | I domain | G1 | ‡‡ | – | – | ‡‡ | ‡‡ | – | ‡‡ | – | – | ‡‡ | ‡‡ | – |
| Mn41 | I domain | G1 | ‡‡ | – | – | ‡‡ | ‡‡ | – | ‡‡ | – | – | ‡‡ | ‡‡ | – |
| 14B6E.2 | I domain | M | ‡‡ | – | – | ‡‡ | ‡‡ | – | ‡‡ | – | – | ‡‡ | ‡‡ | – |
| 5A4.C5 | I domain | G1 | ‡‡ | – | – | ‡‡ | ‡‡ | – | ‡‡ | – | – | ‡‡ | ‡‡ | – |
| CBRM1/1 | I domain | G2b | ‡‡ | – | – | ‡‡ | ‡‡ | – | ‡‡ | – | – | ‡‡ | ‡‡ | – |
| CBRM1/2 | I domain | G1 | ‡‡ | – | – | ‡‡ | ‡‡ + | – | ‡‡ + | – | – | ‡‡ | ‡‡ | – |
| CBRM1/4 | I domain | G1 | ‡‡ | – | – | ‡‡ | ‡‡ | – | ‡‡ | – | – | ‡‡ | ‡‡ | – |
| CBRM1/13 | I domain | G2a | ‡‡ | – | – | ‡‡ | ‡‡ | – | ‡‡ | – | – | ‡‡ | ‡‡ | – |
| CBRM1/21 | I domain | G1 | ‡‡ | – | – | ‡‡ | ‡‡ | – | ‡‡ | – | – | ‡‡ | ‡‡ | – |
| CBRM1/22 | I domain | G1 | ‡‡ | – | – | ‡‡ | ‡‡ | +/– | ‡‡ | – | – | ‡‡ | ‡‡ | +/– |
| CBRM1/24 | I domain | G1 | ‡‡ | – | – | ‡‡ | ‡‡ | + | ‡‡ | – | – | ‡‡ | ‡‡ | – |
| CBRM1/27 | I domain | G2a | ‡‡ | – | – | ‡‡ | ‡‡ | – | ‡‡ | – | – | ‡‡ | ‡‡ | – |
| CBRM1/29 | I domain | G1 | ‡‡ | – | – | ‡‡ | ‡‡ | – | ‡‡ | – | – | ‡‡ | ‡‡ | – |
| CBRM1/31 | I domain | G1 | ‡‡ | – | – | ‡‡ | ‡‡ | – | ‡‡ | – | – | ‡‡ | ‡‡ | +/– |
| CBRM1/33 | I domain | G2a | ‡‡ | – | – | ‡‡ | ‡‡ | – | ‡‡ | – | – | ‡‡ | ‡‡ | – |
| CBRM1/34 | I domain | G1 | ‡‡ | – | – | ‡‡ | ‡‡ | – | ‡‡ | – | – | ‡‡ | ‡‡ | – |
| OKM1 | C-terminal | G2b | ‡‡ | – | – | ‡‡ | – | – | – | – | – | – | ‡‡ | – |
| VIM12 | C-terminal | G1 | ‡‡ | – | – | ‡‡ | – | – | – | – | – | – | ‡‡ | – |
| CBRM1/9 | C-terminal | G2a | ‡‡ | – | – | ‡‡ | ‡‡ | ‡‡ | – | ‡‡ | ‡‡ | ‡‡ | ‡‡ | – |
| CBRM1/10 | C-terminal | G1 | ‡‡ | – | – | ‡‡ | ‡‡ | ‡‡ | – | ‡‡ | ‡‡ | ‡‡ | ‡‡ | – |
| CBRM1/16 | C-terminal | G1 | ‡‡ | – | – | ‡‡ | ‡‡ | ‡‡ | – | ‡‡ | ‡‡ | ‡‡ | ‡‡ | – |
| CBRM1/17 | C-terminal | G2a | ‡‡ | – | – | ‡‡ | ‡‡ | ‡‡ | – | ‡‡ | ‡‡ | + | ‡‡ | – |

| mAb | Epitope | Isotype | Mac-1 | p150.95 | M-e-X | X-e-M | M-b-X | X-b-M | M-e-X | X-a-M | M-e-X-b-M | X-e-M-b-X | M-b-X-a-M | X-b-M-a-X |
|---|---|---|---|---|---|---|---|---|---|---|---|---|---|---|
| CBRM1/18 | C-terminal | G2a | +++ | – | – | +++ | – | +++ | – | +++ | +++ | +/– | +++ | – |
| CBRM1/23 | C-terminal | G2a | +++ | – | – | +++ | – | +++ | – | +++ | +++ | – | +++ | – |
| CBRM1/25 | C-terminal | G2a | +++ | – | – | +++ | – | +++ | – | +++ | +++ | – | +++ | – |
| CBRM1/26 | C-terminal | G2b | +++ | – | – | +++ | – | +++ | – | +++ | +++ | – | +++ | – |
| CBRM1/30 | C-terminal | G2b | +++ | – | – | +++ | – | +++ | – | +++ | +++ | – | +++ | – |
| OKM10old | NH$_2$/cation | G2b | ++ | – | – | +/– | – | – | ++ | – | ++ | – | – | – |
| CBRM1/32 | NH$_2$/cation | G1 | ++ | – | – | +++ | – | +/– | ++ | – | ++ | – | – | +/– |
| CBRM1/20 | cation | G1 | ++ | – | – | ++ | – | ++ | +/– | – | ++ | – | – | ++ |
| OKM10new | ? | G2b | – | – | ++ | + | ++ | +/– | ++ | ++ | + | + | ++ | – |
| CBRM1/28 | ? | G1 | – | +++ | +++ | – | ++ | – | +/– | + | – | ++ | + | + |
| p150/4G1 | p150.95 | G2a | – | +++ | – | – | ++ | – | +++ | – | ++ | ++ | – | ++ |
| BLY6 | p150.95 | G1 | – | +++ | ++ | – | – | ++ | – | ++ | – | – | ++ | ++ |
| SHCL3 | p150.95 | G2a | – | +++ | – | + | ++ | ++ | – | ++ | ++ | ++ | – | + |
| TS1/18 | CD18 | G1 | ++ | ++ | ++ | ++ | ++ | ++ | ++ | ++ | ++ | ++ | ++ | ++ |

| mAb | Epitope | iC3b-E Binding | Neutrophil Aggregation | Fibrinogen Binding | ICAM-1 Binding |
|---|---|---|---|---|---|
| | | % Inhibition ± SEM | | | |
| LPM19c | I domain | 94.1 ± 5.9 | 81.2 ± 12.3 | 97.7 ± 1.8 | 100.0 ± 0.1 |
| OKM9 | I domain | 33.6 ± 9.7 | 8.4 ± 1.3 | 70.0 ± 5.6 | 49.9 ± 13.2 |
| LM2/1 | I domain | 18.1 ± 14.7 | 8.7 ± 2.4 | 47.6 ± 9.9 | 11.8 ± 20.4 |
| TMG-65 | I domain | 87.1 ± 14.7 | 35.7 ± 5.9 | 91.8 ± 0.8 | 95.1 ± 3.9 |
| Mn41 | I domain | 91.5 ± 10.6 | 30.4 ± 4.7 | 94.0 ± 0.3 | 93.3 ± 4.0 |
| 14B6E.2 | I domain | 85.0 ± 10.7 | 24.8 ± 8.9 | 78.8 ± 1.0 | 99.7 ± 0.2 |
| 5A4.C5 | I domain | 97.4 ± 0.7 | 14.3 ± 5.3 | 71.7 ± 1.0 | 99.9 ± 0.2 |
| CBRM1/1 | I domain | 55.9 ± 10.0 | 18.1 ± 2.7 | 77.0 ± 6.5 | 100.0 ± 0.1 |
| CBRM1/2 | I domain | 63.1 ± 10.5 | 20.7 ± 5.2 | 76.3 ± 2.4 | 88.7 ± 2.3 |
| CBRM1/4 | I domain | 83.3 ± 7.2 | 19.3 ± 4.4 | 86.7 ± 2.0 | 93.1 ± 3.5 |
| CBRM1/13 | I domain | 36.8 ± 5.0 | 15.3 ± 2.1 | 45.9 ± 11.3 | 32.3 ± 13.3 |
| CBRM1/21 | I domain | 88.6 ± 8.4 | 21.2 ± 1.6 | 86.8 ± 2.9 | 99.4 ± 0.4 |
| CBRM1/22 | I domain | 77.2 ± 11.6 | 18.0 ± 2.0 | 71.9 ± 2.9 | 99.3 ± 0.5 |
| CBRM1/24 | I domain | 93.4 ± 8.0 | 21.4 ± 1.1 | 70.6 ± 3.6 | 83.6 ± 3.6 |
| CBRM1/27 | I domain | 45.0 ± 12.6 | 21.7 ± 8.2 | 84.2 ± 3.5 | 45.3 ± 13.3 |
| CBRM1/29 | I domain | 99.1 ± 1.3 | 51.2 ± 5.9 | 81.8 ± 5.2 | 99.1 ± 0.2 |
| CBRM1/31 | I domain | 45.6 ± 12.0 | 30.9 ± 10.4 | 81.9 ± 3.3 | 77.5 ± 13.2 |
| CBRM1/33 | I domain | 94.7 ± 6.3 | 21.5 ± 6.1 | 71.7 ± 1.9 | 99.0 ± 1.2 |
| CBRM1/34 | I domain | 90.8 ± 3.5 | 29.5 ± 5.7 | 88.6 ± 4.3 | 99.5 ± 0.3 |
| OKM1 | C-terminal | 38.1 ± 9.3 | 2.2 ± 1.5 | -31.9 ± 17.5 | -41.6 ± 28.3 |
| VIM12 | C-terminal | 13.2 ± 9.8 | 1.2 ± 0.6 | -7.3 ± 9.6 | 4.9 ± 2.7 |
| CBRM1/9 | C-terminal | 41.4 ± 2.9 | 0.0 ± 0.7 | 2.8 ± 7.6 | 3.4 ± 3.1 |
| CBRM1/10 | C-terminal | 37.2 ± 2.9 | 2.8 ± 1.0 | 58.0 ± 5.5 | 42.3 ± 4.3 |

| mAb | Epitope | iC3b-E Binding | Neutrophil Aggregation | Fibrinogen Binding | ICAM-1 Binding |
|---|---|---|---|---|---|
| CBRM1/16 | C-terminal | 58.1 ± 11.7 | 1.2 ± 1.9 | -4.7 ± 4.1 | 37.9 ± 15.9 |
| CBRM1/17 | C-terminal | 50.2 ± 7.1 | 0.6 ± 1.5 | -3.4 ± 4.4 | 21.9 ± 12.4 |
| CBRM1/18 | C-terminal | 49.5 ± 12.8 | 1.3 ± 2.0 | 3.6 ± 3.2 | 33.8 ± 16.3 |
| CBRM1/23 | C-terminal | 20.5 ± 11.3 | 1.1 ± 1.1 | 18.0 ± 3.8 | 12.2 ± 17.5 |
| CBRM1/25 | C-terminal | 10.5 ± 11.3 | 2.7 ± 1.5 | 1.4 ± 5.6 | 52.5 ± 10.6 |
| CBRM1/26 | C-terminal | 9.3 ± 14.5 | 3.2 ± 1.4 | 29.6 ± 9.5 | 47.8 ± 18.3 |
| CBRM1/30 | C-terminal | 42.5 ± 9.2 | 3.4 ± 4.2 | -5.7 ± 5.3 | 50.0 ± 14.2 |
| OKM10old | NH2/cation | 80.9 ± 21.6 | ND | ND | ND |
| CBRM1/32 | NH2/cation | 64.8 ± 5.3 | 21.2 ± 7.3 | 84.9 ± 3.8 | 96.8 ± 1.1 |
| CBRM1/20 | cation | 26.7 ± 12.4 | 6.6 ± 0.9 | -12.9 ± 9.8 | 5.4 ± 5.6 |
| OKM10new | ? | -5.7 ± 11.3 | 9.4 ± 1.2 | 9.6 ± 11.0 | 25.3 ± 14.8 |
| CBRM1/28 | ? | 25.7 ± 11.5 | 0.7 ± 0.2 | 8.8 ± 2.4 | 2.4 ± 3.4 |
| TS1/22 | LFA-1 | 0.0 ± 10.9 | 0.4 ± 0.4 | -5.4 ± 6.0 | 2.7 ± 7.0 |
| p150/461 | p150.95 | ND | ND | ND | ND |
| TS1/18 | CD18 | 14.1 ± 3.3 | 75.7 ± 10.2 | 46.5 ± 6.5 | 91.0 ± 3.5 |
| R15.7 | CD18 | 46.6 ± 15.1 | 53.0 ± 2.9 | 89.3 ± 1.8 | 68.3 ± 11.5 |
| R6.5 | CD54 | ND | ND | ND | 86.3 ± 4.6 |

FIG.16B

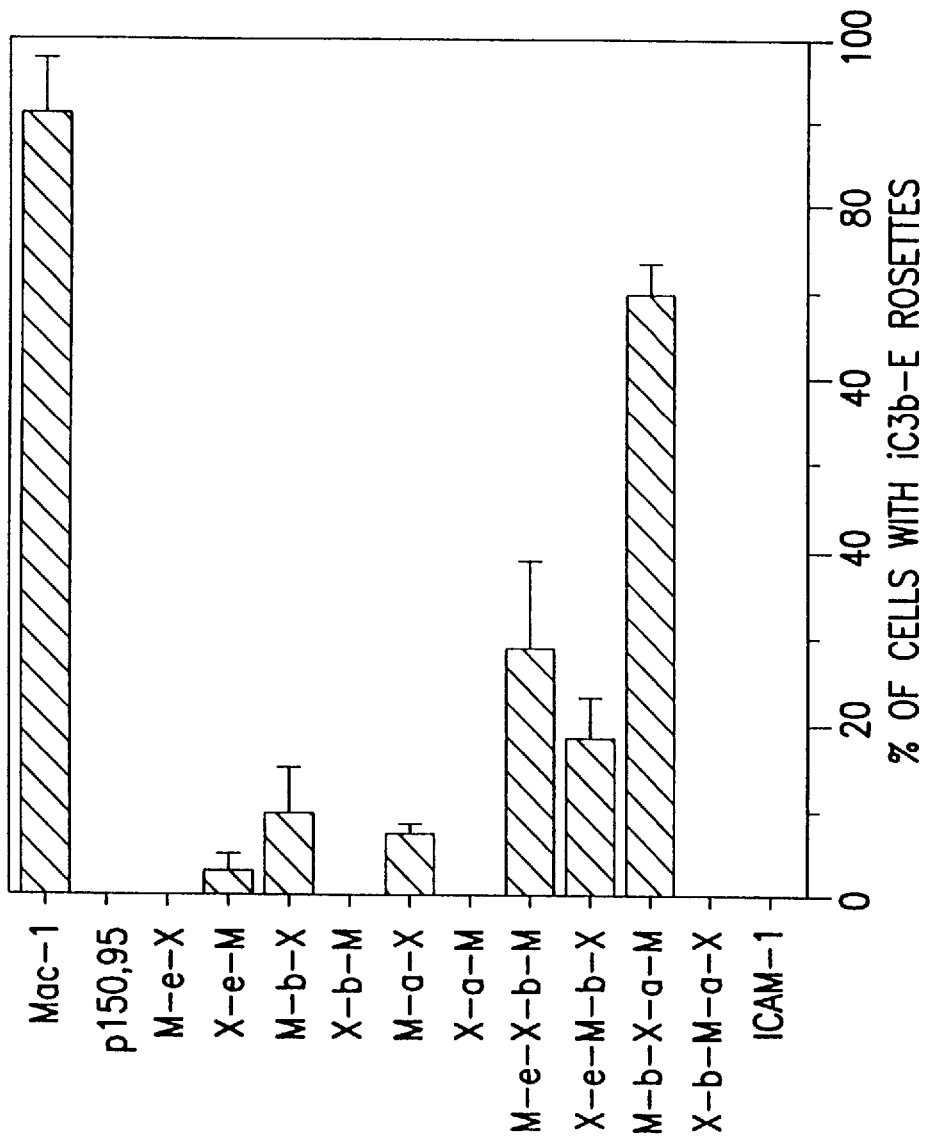

ANTIBODIES WHICH BIND A SUBPOPULATION OF MAC-1 (CD11B/CD18) MOLECULES WHICH MEDIATE NEUTROPHIL ADHESION TO ICAM-1 AND FIBRINOGEN

BACKGROUND OF THE INVENTION

This application is a continuation of prior application Ser. No. 07/964,156, filed Oct. 22, 1992 abandoned; which is a continuation-in-part of application Ser. No. 07/953,904, filed Sep. 30, 1992 (abandoned).

This invention was made with Government support under Grant No. CA31799, awarded by the National Institutes of Health. The Government has certain rights in the invention.

FIELD OF THE INVENTION

The present invention relates to the field of cellular adhesion and the use of anti-adhesion molecules as a means of mediating biological processes which are facilitated by myeloid cell adhesion, migration and activation. Specifically, the present invention discloses that specific subpopulations of Mac-1 are activated when myeloid cells are stimulated and that upon activation, activation specific epitopes appear on the Mac-1 molecule. Based on the identification of activation specific epitopes, a new class of anti-Mac-1 antibodies are disclosed which are capable of binding to an activated form of Mac-1 present on stimulated myeloid cells but are substantially incapable of binding to non-activated Mac-1 and resting myeloid cells.

DESCRIPTION OF THE RELATED ART

Under normal conditions, circulating neutrophils flow through the vascular system making few attachments to the underlying endothelium. Within minutes of an exposure to an inflammatory stimulus, neutrophils roll along the adjacent vessel wall, adhere firmly to the endothelium, and then traffic into the parenchyma (Atherton et al., *J. Physiol.* 222:447–474 (1972)). Recent experiments have identified the molecules on neutrophil and endothelial cell surface that facilitate emigration. Members of the selectin family (Springer et al., *Nature* 349:196–197 (1991)) mediate the initial rolling and members of the integrin family (Hynes, *Cell* 69:11–25 (1992)) strengthen neutrophil attachment to the endothelium (Lawrence et al., *Cell* 65:859–873 (1991)), and then promote transmigration to the underlying tissue (Anderson, et al., *Blood* 76:2613–2621 (1990); Smith, et al., *J. Clin. Invest.* 83:2008–2017 (1989)).

The integrin family of heterodimeric glycoproteins mediate cell adhesion and attachment to the extracellular matrix (Hynes, *Cell* 48:549–554 (1987); Hynes, *Cell* 69:11–25 (1992)). The leukocyte integrin subfamily includes three members, LFA-1 CD11a/CD18), Mac-1 (CD11b/CD18) and p150,95 (CD11c/CD 18) that share a common β subunit that is noncovalently associated with unique but closely related α chains (Kishimoto et al., *Adv. Immunol.* 46:149–182 (1989); Springer, *Nature* 346:425–433 (1990)). These glycoproteins share a common CD18 β subunit (95,000 $M_r$) but have individual unique CD11 α subunits (175,000, 160,000, 150,000$M_r$) respectively, that are structurally homologous (Larson, et al., *J. Cell Biol.* 108:703–712 (1989)). All three members share two prominent features in the extracellular region of the molecule, a putative divalent cation binding region consisting of three tandem repeats of an EF-hand motif, and a 200 amino acid inserted or "I" domain (Arnaout, et al., *J. Cell Biol.* 106:2153–2158 (1988); Corbi, et al., *J. Biol. Chem.* 263:12403–12411 (1988); Corbi, et al., *EMBO J.* 6:4023–4028 (1987); Kaufman, et al., *J. Immunol.* 147:369–371 (1991); Larson, et al., *J. Cell Biol.* 108:703–712 (1989); Pytela, *EMBO J.* 7:1371–1378 (1988)). The I domain is absent in all other known integrin α subunits except for the $\alpha_1$ and $\alpha_2$ subunits of the VLA subfamily of integrins (Hemler, *Annu. Rev. Immunol.* 8:365–400 (1990); Hynes, *Cell* 69:11–25 (1992)).

The leukocyte integrins mediate several adhesive events that are crucial for immune system function. They promote the adhesion that is required for T lymphocyte target cell lysis (Davignon, et al., *Proc. Natl. Acad. Sci. USA* 78:4535–4539 (1981)), T lymphocyte proliferation (Davignon, et al., *Proc. Natl. Acad. Sci. USA* 78:4535–4539 (1981)), natural killing (Krensky et al., *J. Immunol* 131:611–616 (1983)), leukocyte adhesion to, and migration through endothelial cells (Dustin et al., *J. Cell Biol.* 107:321–331 (1988); Harlan et al., *Blood* 66:167–178 (1985); Haskard et al, *J. Immunol.* 137:2901–2906 (1986); Lo et al., *J. Exp. Med.* 169:1779–1793 (1989); Lo et al., *J. Immunol.* 143(10):3325–3329 (1989); Smith, et al., *J. Clin. Invest.* 83:2008–2017 (1989); Smith, et al., *J. Clin. Invest.* 82:1746–1756 (1988)), neutrophil homotypic aggregation, and neutrophil chemotaxis (Anderson, et al., *J. Immunol.* 137:15–27 (1986)).

Mac-1 is expressed in an intracellular, vesicular compartment in circulating neutrophils and monocytes which is mobilized to the cell surface by inflammatory mediators (Todd, et al., *J. Clin. Invest.* 74:1280–1290 (1984); Springer, et al., In: *Biochemistry of Macrophages*(CIBA Symposium 118), Pitman, London, pp. 102–126 (1986); Lanier, et al., *Eur. J. Immunol.* 15:713–718 (1985); Yancey, et al., *J. Immunol.* 135:465–470 (1985)). This mobilization correlates with increased adhesiveness (Anderson, et al., *Ann. Rev. Med.* 38:175–194 (1987)). Mac-1 α-subunit message was detected in blood monocytes and PMA-induced myeloid cell lines, but not in most cells of the T or B lineages, correlating with Mac-1 protein surface expression.

Some cytotoxic T lymphocyte clones have been found to express similar quantities of p150,95 and LFA-1. Monoclonal antibodies to the LFA-1 and p150,95 alpha-subunits inhibit killing by such CTL clones to similar extent and are additive in their inhibitory effects (Keizer, et al., *J. Immunol.* 138:3130–3136 (1987)). Furthermore, antibodies to p150,95 alpha-subunits have been shown to inhibit monocyte attachment to endothelium (Keizer, et al., *Eur. J. Immunol.* 17:1317–1322 (1987)).

Monoclonal antibodies to Mac-1 or p150,95 inhibit neutrophil aggregation and adherence to endothelial cells, protein-coated surfaces, bacteria, protozoan parasites, and fungi (Harlan, et al., *Blood* 66:167–178 (1985); Springer, et al., In: *Biochemistry of Macrophages* (CIBA Symposium 118), Pitman, London, pp. 102–126 (1986); Dana, et al., *J. Immunol.* 137:3259 (1986); Bullock, etal., *J. Exper. Med.* 165:195–210 (1987); Mosser, et al., *J. Immunol.* 135:2785–2789 (1985)).

Mac-1 (CD11b/CD18) is a leukocyte adhesion glycoprotein that has been demonstrated to bind multiple ligands including iC3b (Beller, et al., *J. Exper. Med.* 156:1000–1009 (1982)), fibrinogen (Altieri, et al., *J. Cell. Biol.* 107:1893–1900 (1988); Wright, et al., *Proc. Nat'l. Acad. Sci. (U.S.A.)* 85:7734–7738 (1988)),and Factor X (Altieri, et al., *J. Biol. Chem.* 863:7007–7015 (1988)) in addition to its role in cell-cell and cell-substrate adhesive interactions. Detergent-soluble Mac-1 and p150,95 have been shown to bind to iC3b-Sepharose (Micklem, et al., *Biochem. J.* 231:233–236 (1985)).

The α-subunit of Mac-1 is a transmembrane protein of 1137 residues with a long extracellular domain (1092 residues) and a 19-amino acid cytoplasmic tail. The extracellular domain contains 3 putative divalent cation-binding sequences and 19 potential N-glycosylation sites. The amino acid sequence of Mac-1 α shows that it is a member of the integrin superfamily; Mac-1 α shows 63% identity to the α-subunit of the leukocyte adhesion glycoprotein p150,95 and 25% to the α-subunits of the extracellular matrix receptor platelet glycoprotein IIb/IIIa, the fibronectin receptor and the vitronectin receptor. The Mac-1 α-subunit putative divalent cation-binding sites and the flanking regions exhibit a high degree of identity both to the p150,95 α-subunit (87% identity at the amino acid level) and to the rest of the integrin α-subunits (38%). The α-subunit of Mac-1, like the p150,95 α-subunit, contains a domain of 187 amino acids in the extracellular region which is absent in other integrins. This inserted or "I" domain is homologous to the A domains of van Willebrand factor, which in turn are homologous to regions of the C3-binding proteins factor B and C2. These findings draw attention to this region of Mac-1 as a potential binding site for iC3b.

The functional role of Mac-1 was first illustrated by the ability of anti-Mac-1 α-subunit monoclonal antibodies (MAb) to block the rosetting of iC3b-coated erythrocytes to macrophages and polymorphonuclear leukocytes (Beller, et al., *J. Exper. Med.* 156:1000–1009 (1982)), demonstrating that Mac-1 is indistinguishable from the complement receptor type three (CR3). Subsequently, the involvement of Mac-1 in inflammatory processes was evidenced by the inhibition of neutrophil aggregation and adhesion to endothelial cells by anti-Mac-1 α-subunit and anti-β-subunit-specific MAb (Anderson, et al., *J. Immunol.* 137:15–27 (1986); Dana, et al., *J. Immunol.* 137:3259–3263 (1986); Vedder, et al., *J. Clin. Invest.* 81:672–682 (1988)). Recent epitope mapping studies have suggested that the sites involved in iC3b-binding are distinct from those involved in neutrophil aggregation and adherence to protein-coated plastic (Anderson, et al., *J. Immunol.* 137:15–27 (1986); Dana, et al., *J. Immunol.* 137:3259–3263 (1986), Rosen, et al., *J. Exper. Med.* 166:1685–1701 (1987)). Therefore, Mac-1 appears to be a receptor matures at least 2 sites for its adhesion-related functions.

The expression of functional activity of Mac-1 is regulated during leukocyte differentiation and activation. Differentiation and maturation of myelomonocytic cell lines results in increased Mac-1 expression (Miller, et al., *J. Immunol.* 137:2891–2900 (1986)), while blood monocyte differentiation into tissue macrophages is accompanied by a considerable decrease in the amount of Mac-1 on all cell surfaces (Hogg, et al., *Eur. J. Immunol.* 16:240–248 (19886)). The expression of Mac-1 on the surface of circulating neutrophils and monocytes is upregulated by inflammatory stimuli; Mac-1 is stored in an intracellular vesicular compartment which is rapidly mobilized to the cell surface by chemoattractants (Todd, et al., *J. Clin. Invest.* 74:1280–1290 (1984)); Miller, et al., *J. Clin. Invest.* 80:535–544 (1987)). Although the augmented expression of Mac-1 can lead to increased adhesiveness, qualitative changes after cell activation may also be important in regulation ligand binding (Detmers, et al., *J. Cell Biol.* 105:1137–1145 (1987)). Both the qualitative and quantitative changes may be important in regulation of leukocyte binding to post-capillary endothelium at inflammatory sites.

Thus, in summary, the ability of leukocytes to maintain the health and viability of an animal requires that they be capable of adhering to other cells (such as endothelial cells) and proteins (such as iC3b). This adherence has been found to require contacts which involve specific receptor molecules present on the surface of the leukocytes. Some of these cell surface receptor molecules have been found to be highly related to one another. Humans whose leukocytes lack these cell surface receptor molecules exhibit chronic and recurring infections, as well as other clinical symptoms.

Experiments by several groups have demonstrated that the adhesiveness of the leukocyte integrins is not constitutive, but rather is controlled by intracellular signals transduced from other surface receptors. For example, LFA-1 on resting T lymphocytes is unable to bind to its counter-receptor ICAM-1 until a signal has been delivered through the antigen receptor (Dustin et al., *Nature* 341:619–624 (1989); van Kooyk, et al., *Nature* 342:811–813 (1989)). The signal to adhere is transient, as within thirty minutes of stimulation, T lymphocytes lose their ability to bind ICAM-1. Similarly, Mac-1 on neutrophils does not bind its cellular or soluble ligands including ICAM-1 (Diamond, et al., *Cell* 65:961–971 (1991)), fibrinogen (Altieri, et al., *J. Cell. Biol.* 107:1893–1900 (1988); Wright, et al., *Proc. Natl. Acad. Sci. USA* 85:7734–7738 (1988)), factor X (Altieri et al., *J. Biol. Chem.* 263:7007–7015 (1988)) or iC3b (Wright et al., *J. Immunol.* 136:1759–1764 (1986)) until a specific signal (e.g., chemotactic factor, cytokine, or phorbol ester) has been delivered; stimulation increases the avidity of Mac-1 for its ligands within seconds (Anderson, et al., *J. Immunol.* 137:15–27 (1986); Buyon, et al., *J. Immunol.* 140:3156–3160 (1988); Detmers, et al., *J. Exp. Med.* 171:1155–1162 (1990); Wright et al., *J. Immunol.* 136:1759–1764 (1986)).

While it is clear that activation facilitates leukocyte integrin interaction with ligand, the molecular mechanism for the change in avidity remains poorly understood. Because there is no increase in LFA-1 expression after antigen stimulation or phorbol ester treatment in T cells, the avidity change of LFA-1 for ICAM-1 is believed to occur because of a structural change in the molecule (Dustin et al., *Nature* 341:619–624 (1989)). Alternatively, the change in avidity could stem from a signal to cluster adhesion receptors at the cell surface (Detmers, et al., *J. Cell Biol.* 105:1137–1145 (1987)). The mechanism for avidity regulation of Mac-1 on neutrophils appears analogous, but the analysis is complicated by a greater than tenfold quantitative increase in expression that follows stimulation (Berger, et al., *J. Clin. Invest.* 74:1566–1571 (1984); Detmers, et al., *J. Exp. Med.* 171:1155–1162 (1990); Lo et al., *J. Exp. Med.* 169:1779–1793 (1989); Miller, et al., *J. Clin. Invest.* 80:535–544 (1987); Todd, et al., *J. Clin. Invest.* 74:1280–1290 (1984)). However, the change in surface expression that occurs following stimulation does not parallel the kinetics or magnitude of adhesion (Buyon, et al., *J. Immunol.* 140:3156–3160 (1988); Lo et al., *J. Exp. Med.* 169:1779–1793 (1989)), as ion channel antagonists (Vedder et al., *J. Clin. Invest.* 81:676–682 (1988)) or temperature conditions (Schleiffenbaum, et al., *J. Immunol.* 142:3537–3545 (1989)) that inhibit the quantitative increase in Mac-1 expression do not block Mac-1-dependent adhesion to endothelial cells or in vitro substrates. Thus, Mac-1 is hypothesized to undergo additional, conformational changes that facilitate adhesion (Buyon, et al., *J. Immunol.* 140:3156–3160 (1988); Lo et al., *J. Exp. Med.* 169:1779–1793 (1989); Philips, et al., *J. Clin. Invest.* 82:495–501 (1988); Vedder et al., *J. Clin. Invest.* 81:676–682 (1988)). Studies that show that divalent cations (Altieri, *J. Immunol.* 147:1891–1898 (1991); Dransfield, et al., *J. Cell Biol.* 116:219–226 (1992); Dransfield et al., EMBO J. 8:3759–3765 (1989); van Kooyk, et al., J. Cell Biol. 112:345–354 (1991)) or MAbs against Mac-1 or LFA-1 (Dransfield, et al., J. Cell Biol. 116:1527–1535 (1992); Hibbs et al., Science 251:1611–1613 (1991); Keizer et al., J. Immunol. 140:1393–1400 (1988); Robinson, et al., J. Immunol. 148:1080–1085 (1992)) augment adhesion in the absence of activation, support a model in which direct structural changes to the extracellular regions regulate leukocyte integrin avidity.

Despite the cDNA cloning and the identification of an array of ligand interactions, the region(s) on the α and β subunits of the leukocyte integrins that mediate ligand binding have not been characterized. The platelet adhesion molecule $\alpha_{IIb}$-$\beta_3$ (CD41/CD61) is the integrin family member that is best characterized for the subunit domains which contribute to ligand recognition. Chemical cross-linking experiments (D'Souza, J. Biol. Chem. 265:3440–3446 (1990)) and functional studies (D'Souza, Nature 350:66–68 (1991)) suggest that fibrinogen binds to an 11-residue peptide within the divalent cation binding repeats on $\alpha_{IIb}$, and that R-G-D peptides bind to a site on the $\beta_3$ subunit between amino acid residues 61–203 (D'Souza, Science 242:91–93 (1988); Smith et al., J. Biol. Chem. 263:18726–18731 (1988)). A natural point mutation found in patients with Glanzmann's thrombasthenia on residue 119 of the $\beta_3$ subunit abrogates ligand recognition and disturbs binding of divalent cations (Loftus, et al., Science 249:915–918 (1990)). However, whether the results can be generalized to the leukocyte integrins is not clear. Although Mac-1 was reported to bind to R-G-D-like sequences in some of its ligands (Ross, et al., J. Leukoc. Biol. 51:109–117 (1992); Wright, et al., J. Exp. Med. 169:175–183 (1989); Wright, et al., Proc. Natl. Acad. Sci. USA 84:1965–1968 (1987); Wright, et al., Proc. Natl. Acad. Sci. USA 85:7734–7738 (1988)), recent studies have demonstrated that it does not utilize R-G-D-like sequences to bind iC3b and fibrinogen (Altieri, et al., J. Biol. Chem. 265:12119–12122 (1990); Altieri, et al., J. Cell. Biol. 107:1893–1900 (1988); Taniguchi-Sidle et al., J. Biol. Chem. 267:635–643 (1992)). Similarly, the binding sites on ICAM-1 for LFA-1 (Staunton, et al., Cell 61:243–254 (1990)) and Mac-1 (Diamond, et al., Cell 65:961–971 (1991)) do not contain R-G-D residues. Thus far, no data has been reported on the localization of ligand binding sites for any of the integrins that contain I domains. Because I domains are structurally homologous to ligand binding modules in von Willebrand factor and complement factor B (Larson, et al., J. Cell Biol. 108:703–712 (1989); Pytela, EMBO J. 7:1371–1378 (1988)), it has been speculated that this region is involved in the recognition of ligands by integrins (Hynes, Cell 69:11–25 (1992); Larson, et al., J. Cell Biol. 108:703–712 (1989); Pytela, EMBO J. 7:1371–1378 (1988)).

Mac-1 is one of the most interesting of the integrins that contain an I domain as it promiscuously binds several soluble and cell surface ligands. Because previous studies had demonstrated that distinct Mac-1-dependent adhesive functions could be blocked by disparate groups of MAbs to Mac-1 α (Anderson, et al., J. Immunol. 137:15–27 (1986); Dana, et al., J. Immunol. 137:3259–3263 (1986); Diamond, et al., "Differential Effects on Leukocyte Functions of CD11a, CD11b, and CD18 Monoclonal Antibodies," in Leukocyte Typing IV, Knapp et al., eds., Oxford University, London, 570–574 (1989); Wright, et al., Proc. Natl. Acad. Sci. USA 80:5699–5703 (1983); Wright, et al., Proc. Natl. Acad. Sci. USA 85:7734–7738 (1988)), we hypothesized that separate structural domains of the molecule might confer functional specificity. Because of the high degree of structural identity, antigenic difference, and apparent functional distinction between Mac-1 and p150,95, we designed reciprocal sets of Mac-1/p150,95 chimeras to map the ligand binding sites. In this report, four functionally distinct ligands are examined. We find that the I domain on Mac-1 is critical for the recognition of all of these ligands.

SUMMARY OF THE INVENTION

The present invention is based on the novel observation that when resting myeloid cells are stimulated, not all Mac-1 molecules which are present on the cell surface become activated. Only select sub-populations of Mac-1 molecules become activated and gain the ability to bind ligand. The present invention further discloses that upon activation, activation specific epitopes appear on the Mac-1 molecule. These activation specific epitope can be used to differentiate activated Mac-1 molecules and stimulated myeloid cells from non-activated Mac-1 molecules and resting myeloid cells.

Based on these activation specific epitopes, the present invention discloses the generation of a novel class of monoclonal antibodies, Mabs, which bind to activated Mac-1 molecules present on stimulated myeloid cells. These antibodies were also found to possess the novel ability to bind to purified Mac-1 substrates, as well as detergent solubilized cell lysates.

A member of this class of antibodies, hereinafter CBRM1/5, is described. CBRM1/5 binds to a subset (10–30%) of Mac-1 molecules present on stimulated neutrophils (those that are activated and are capable of binding ligand). CBRM1/5 was further found to be capable of blocking the binding of activated neutrophils to the Mac-1 ligands, fibrinogen and ICAM-1.

Another member of this class of antibodies, hereinafter CBRM1/19, was additionally isolated. This antibody, though binding to an activation specific epitope, recgizes a different subpopulation then that bound by CBRM1/5.

The present invention further provides methods of isolating other members of this class of antibodies. Specifically, antibodies which react with the same subpopulation of stimulated myeloid cells or the same subpopulation of activated Mac-1 can be identified by their ability to bind the same subpopulation of cells, or the same subpopulation of activated Mac-1 molecules as does CBRM1/5 or CBRM 1/19.

The present invention further provides methods of selectively inhibiting the binding of stimulated myeloid cells to a ligand of Mac-1. Specifically, stimulated myeloid cells can be blocked from binding to Mac-1 ligands by supplying to the myeloid cells an antibody, antibody fragment, or antibody derivative which is (1) capable of binding to activated Mac-1 present on stimulated myeloid cells, (2) is substantially incapable of binding to non-activated Mac-1 and resting myeloid cells, and (3) is capable of inhibiting the ligand/Mac-1 interaction which is being targeted. For example, CBRM1/5 when supplied to a myeloid cell, blocks ICAM-1 and fibrinogen binding.

The present invention further provides methods of treating various pathological conditions which are mediated by myeloid cell adhesion, migration, and ligand interaction. Specifically, an inflammatory response which is mediated by the non-specific defense system can be treated by administering an effective amount of an antibody based agent to a patient in need of such treatment. The antibody based agent used in the present method is an antibody, an antibody fragment, or an antibody derivative which is capable of binding to activated Mac-1 present on stimulated myeloid cells but is substantially incapable of binding to non-activated Mac-1 and resting myeloid cells.

The present invention further provides methods of localizing the presence of stimulated myeloid cells within a subject. Specifically, the presence and location of cells expressing an activated form of Mac-1 can be determined within a subject by administering to the subject a detectably labeled antibody, or antibody fragment, which is capable of binding to activated Mac-1 present on stimulated myeloid cells but is substantially incapable of binding to non-activated Mac-1 and resting myeloid cells. The location of the labeled antibodies or antibody fragments can then be detected using known methods.

The present invention further provides methods of identifying agents capable of activating Mac-1 present on resting myeloid cells. Specifically, resting myeloid cells, or deactivated Mac-1 molecules are contacted with an agent which is to be tested. The cells are then contacted with an antibody which is capable of binding to activated Mac-1 present on stimulated myeloid cells but is substantially incapable of binding to non-activated Mac-1 and resting myeloid cells. The cells, or purified Mac-1 are then examined to determine whether the antibody binds to the cells.

The present invention further provides methods of identifying agents capable of deactivating activated Mac-1 which is present on stimulated myeloid cells. Specifically, stimulated myeloid cells, or purified activated Mac-1 molecules are contacted with an agent which is to be tested. The cells are then contacted with an antibody which is capable of binding to activated Mac-1 present on stimulated myeloid cells but is substantially incapable of binding to non-activated Mac-1 and resting myeloid cells. The cells, or purified Mac-1 molecules are then examined to determine whether the cells bind the antibody.

The present invention further provides methods of selectively killing cells expressing activated Mac-1. Specifically, cells which have activated Mac-1 present on their cell surface can be selectively killed by contacting such a cell with a toxin derivatized antibody which comprises a toxin moiety and an antibody, or antibody fragment which is capable of binding to activated Mac-1 surface but is substantially incapable of binding to non-activated Mac-1.

The present invention further provides methods of selectively removing cells expressing activated Mac-1 from a solution or fluid such as blood. Specifically, stimulated myeloid cells which contain activated Mac-1 on their cell surface can be selectively removed from fluid by passing the fluid over an immobilized antibody, or antibody fragment, which is capable of binding to activated Mac-1 but is substantially incapable of binding to non-activated Mac-1. Such a method can be used in standard leukophoresis type procedures to remove stimulated myeloid cells or myeloid tumor cells which express activated Mac-1 from a patients blood without effecting non-stimulated myeloid cells.

Lane 1, CBRIC2/2 (ICAM-2); Lane 2, LM2/1 (Mac-1α); Lane 3, CBRM1/5 (Mac-1α). Molecular weight standards are indicated to the left.

Figure 2A:
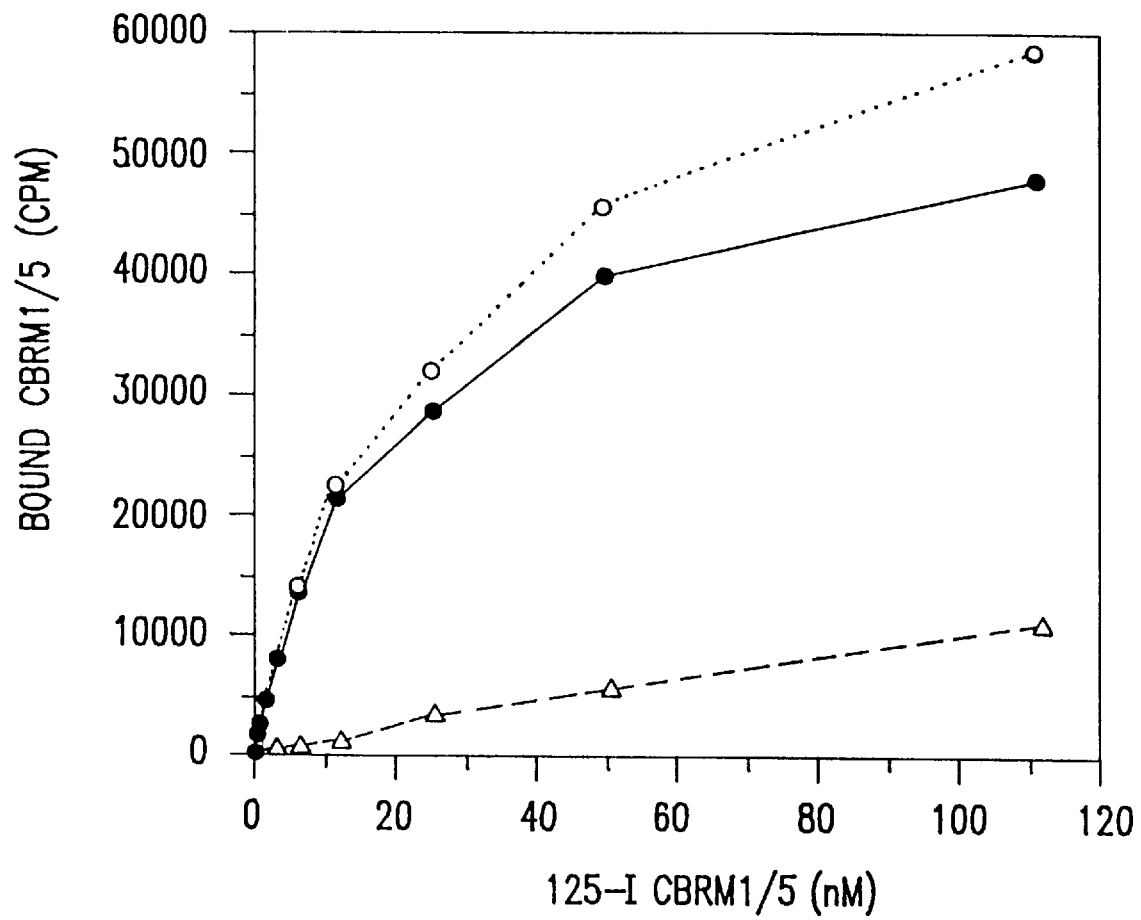
Figure 2B:
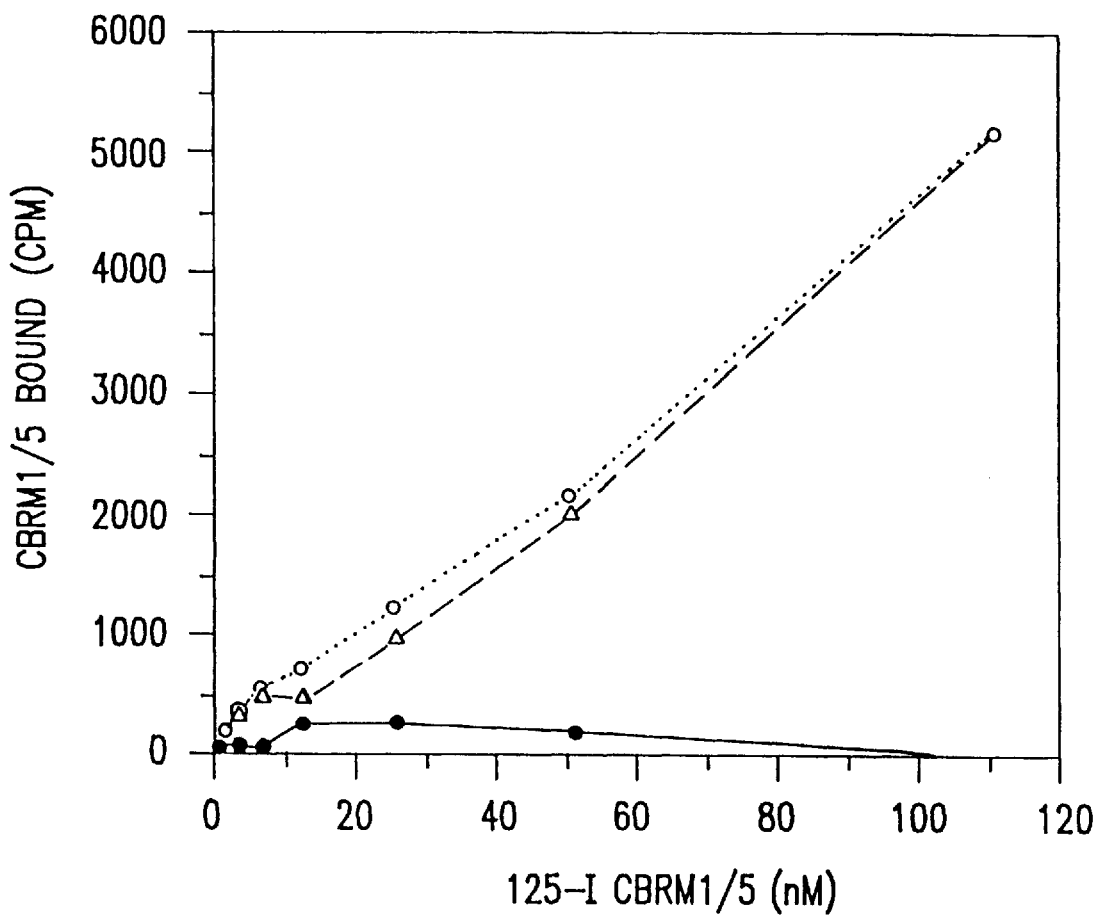
Figure 2C:
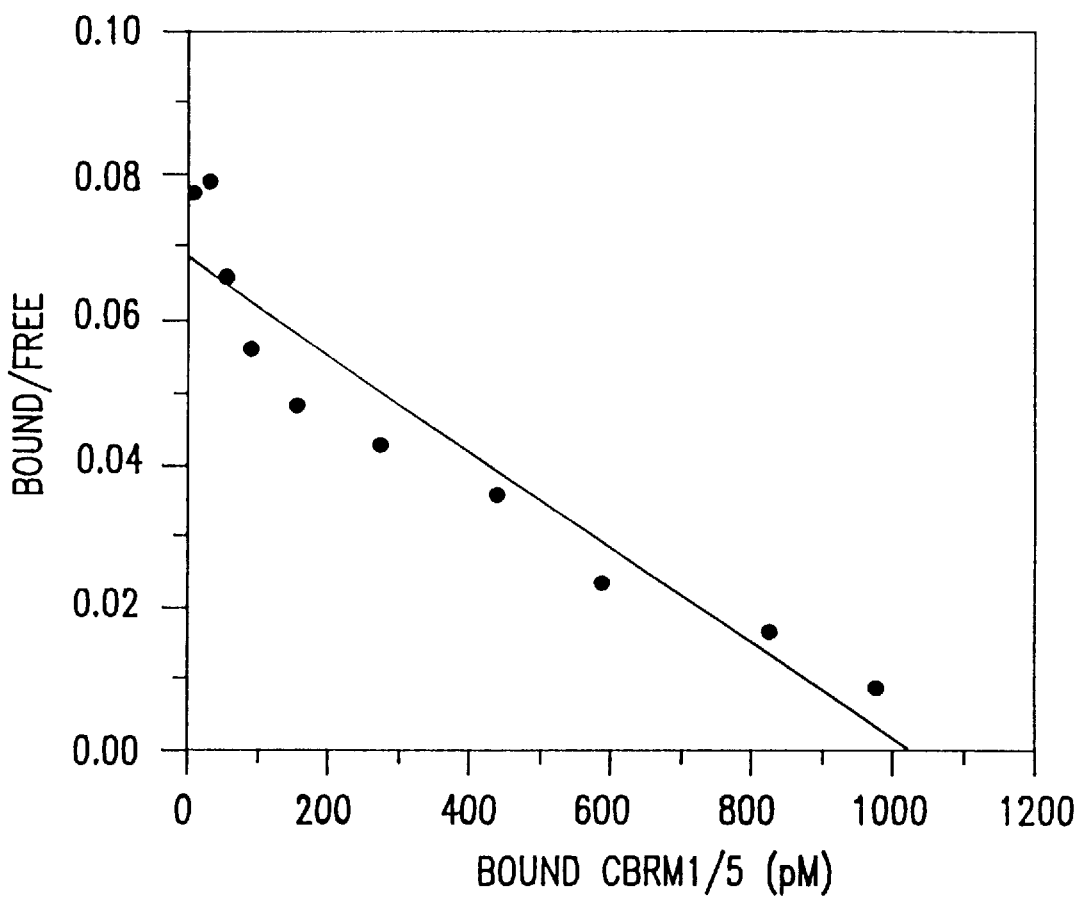
Figure 2D:
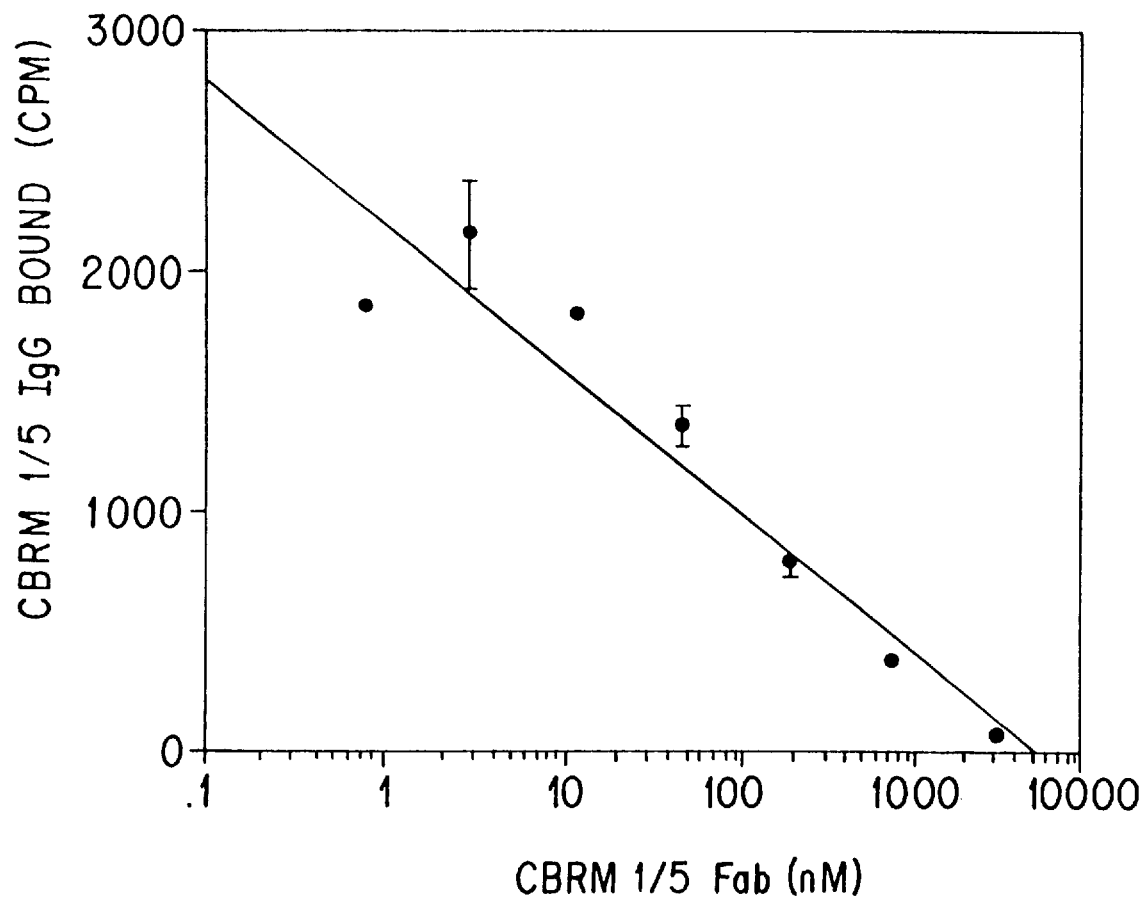
Figure 2E:
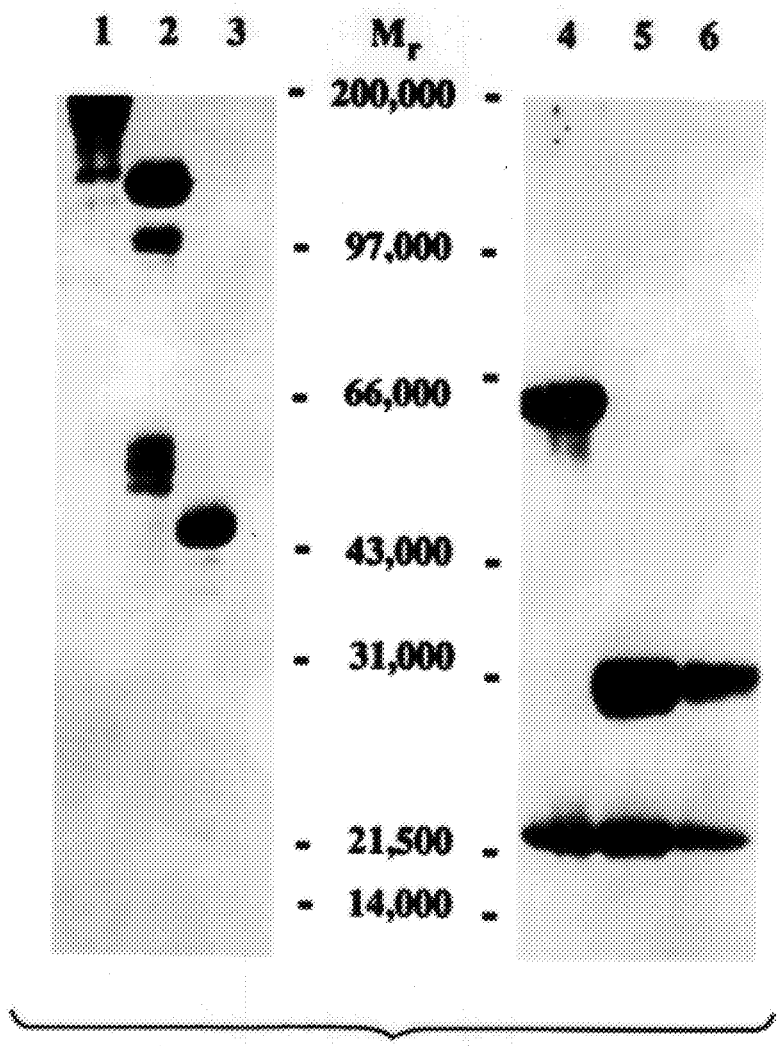

FIG. 2A–2D. Saturation binding of CBRM1/5 IgG and Fab. A, untreated neutrophils; B, neutrophils that were stimulated with PMA (100 ng/ml) for ten minutes at 37° C. Neutrophils were incubated with $^{125}$I-labelled CBRM1/5 either in the absence (open circles) or presence of excess unlabelled CBRM1/5 (open triangles) for 4 hours on ice. Specific binding (closed circles) was measured by subtracting the non-specific from the total binding. FIG. 2C Scatchard plot of the specific binding from the curve in Panel B. The calculated $K_d$ is 15 nM. The x-intercept (1010 pM) is equivalent to 60,800 sites per neutrophil. FIG. 2D Competition of $^{125}$I-CBRM1/5 IgG by CBRM1/5 Fab fragments. Paraformaldehyde fixed neutrophils that had been stimulated with PMA (100 ng/ml) for ten minutes at 37° C. were incubated with a subsaturating concentration of $^{125}$I-CBRM1/5 IgG (1 nM) and increasing concentrations of unlabelled CBRM1/5 Fab fragments for 60 minutes at 37° C. Bars indicate the standard error of the mean for triplicates. FIG. 2E. SDS 6%-PAGE of IgG and Fab fragments of CBRM1/5. Samples (3–5 μgs) of CBRM1/5 IgG (Lane 1,4), CBRM1/5 F(ab')$_2$ (Lane 2,5), or CBRM1/5 Fab (Lane 3,5) were subjected to SDS-8% PAGE under non-reducing (50 mM iodoacetamide, Lanes 1–3) or reducing (5% β-mercaptoethanol, Lanes 4–6) conditions and silver staining. Molecular weight standards under non-reducing and reducing conditions are indicated.

Figure 3A:
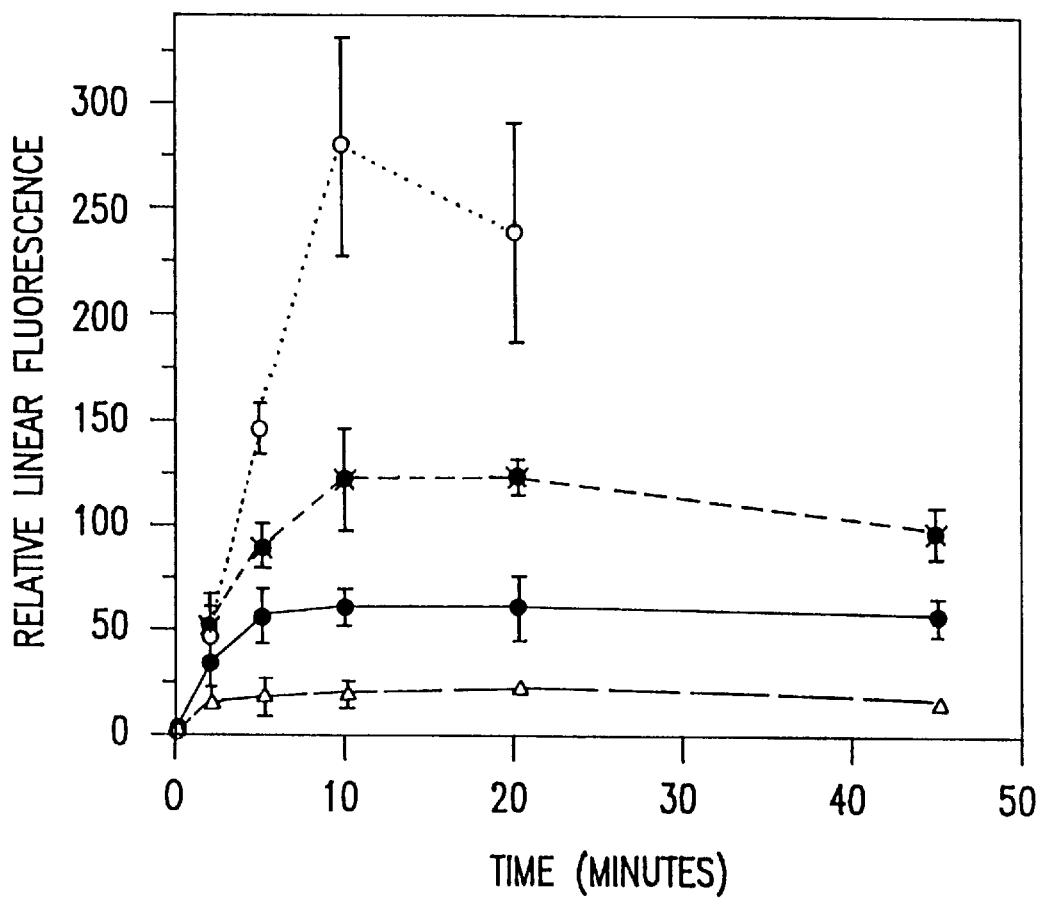
Figure 3B:
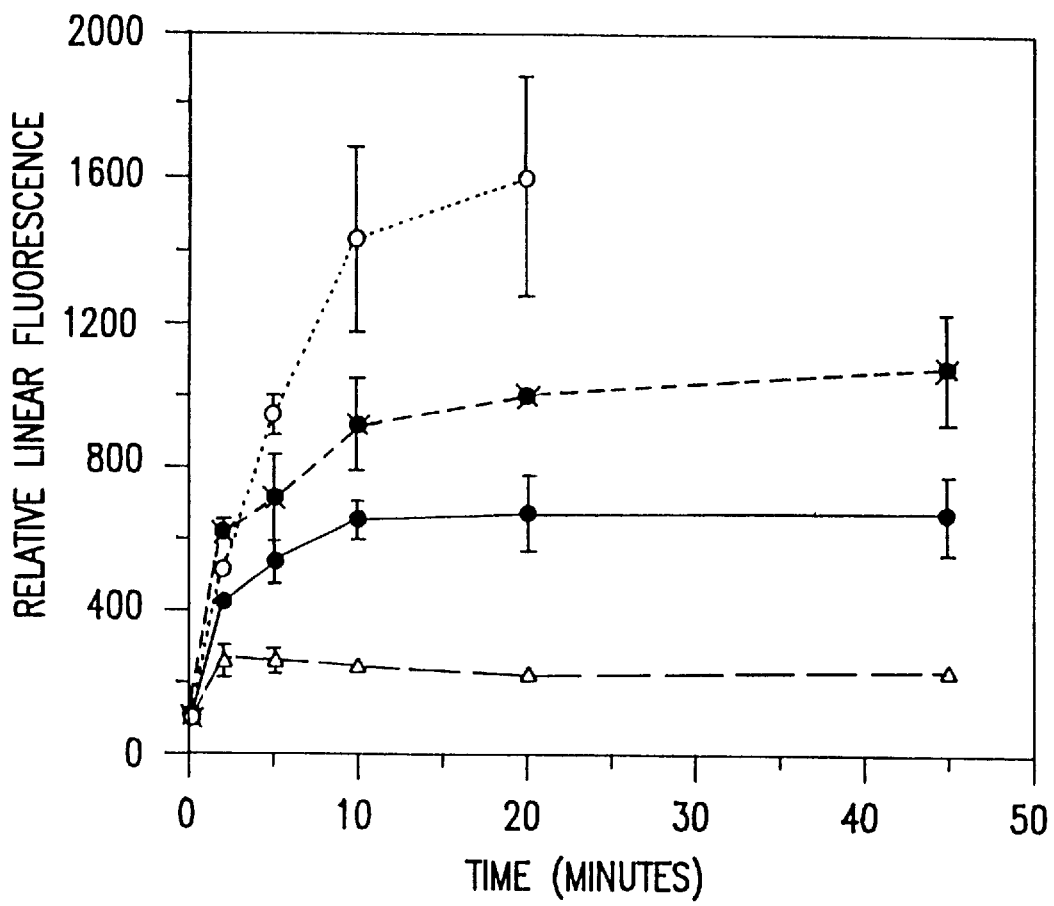

FIG. 3A–3B. Kinetics of expression of Mac-1 epitopes. Neutrophils that were activated at 37° C. for the indicated times with no stimuli (open triangles), FMLP ($10^{-7}$M, solid squares), IL-8 (25 ng/ml, solid circles), or PMA (100 ng/ml, open circles) were immunostained with A, CBRM1/5 or B, LM2/1 and subjected to immunofluorescence flow cytometry. Data are expressed as relative linear fluorescence units and represent the mean of three experiments. The bars indicate the standard error of the mean.

Figure 4A:
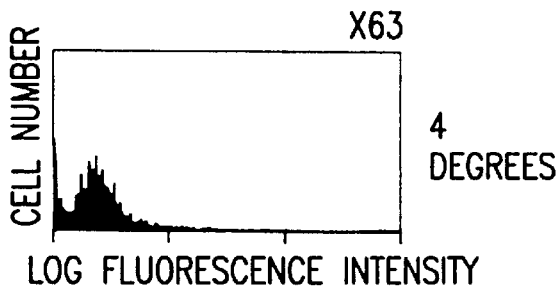
Figure 4E:
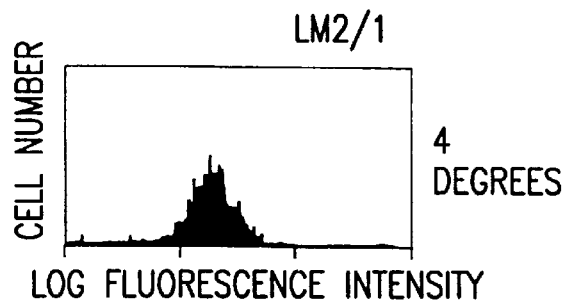
Figure 4B:
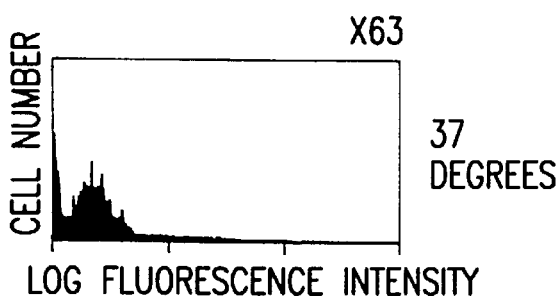
Figure 4F:
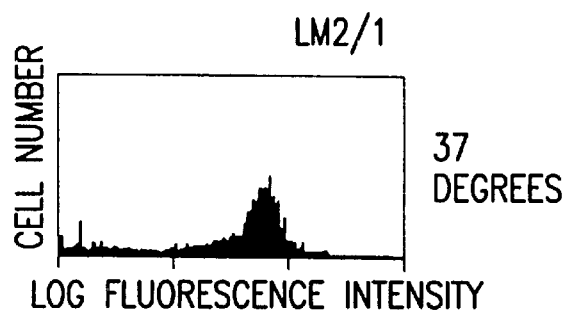
Figure 4C:
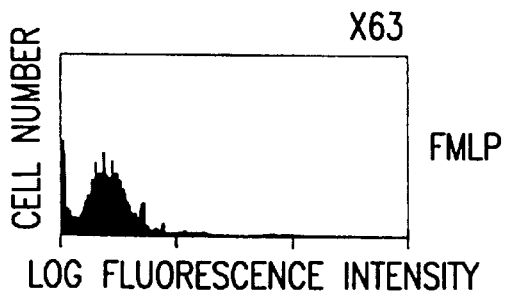
Figure 4G:
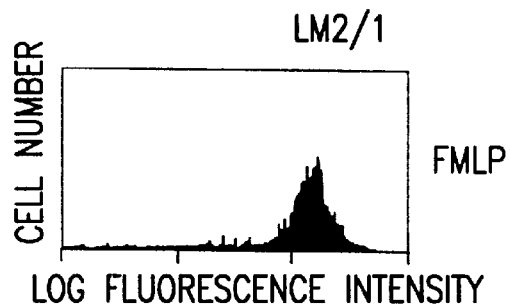
Figure 4D:
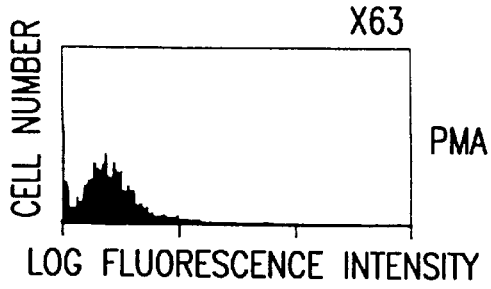
Figure 4H:
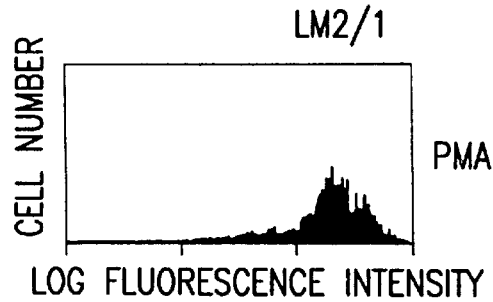
Figure 4I:
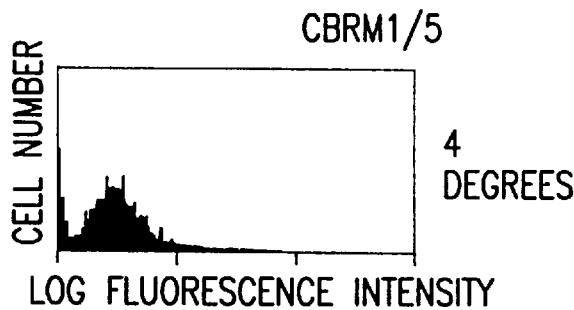
Figure 4M:
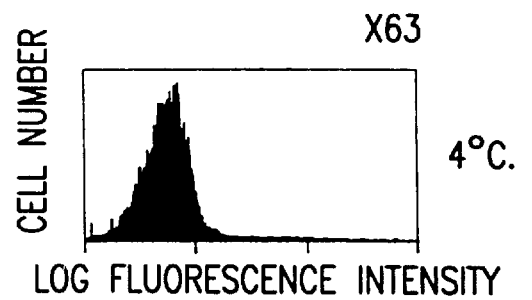
Figure 4J:
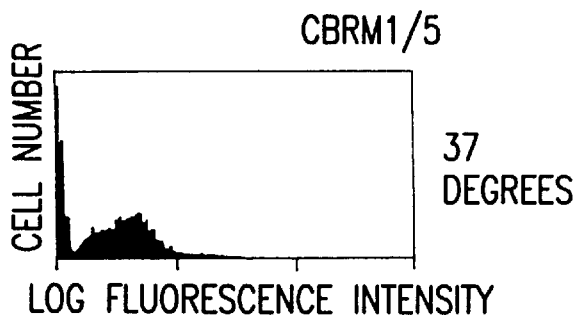
Figure 4N:
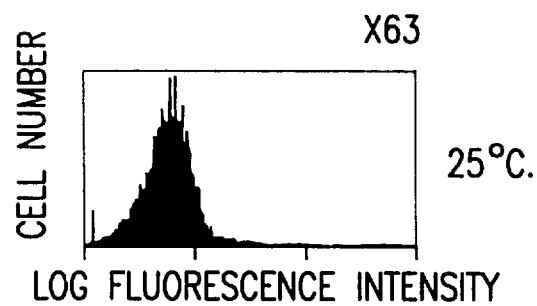
Figure 4K:
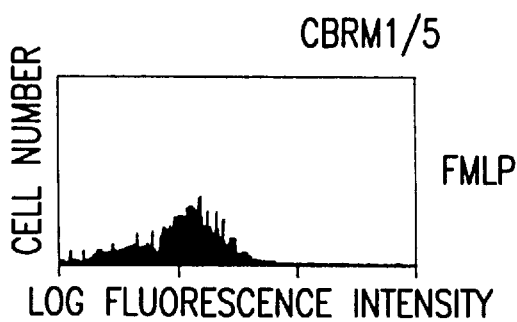
Figure 4O:
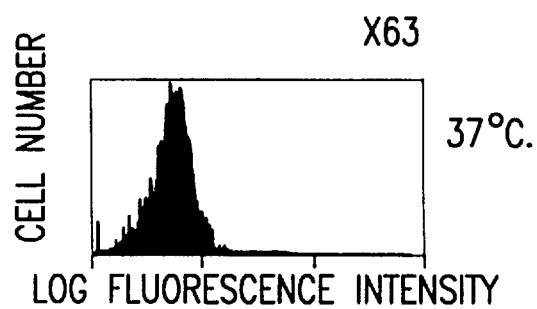
Figure 4L:
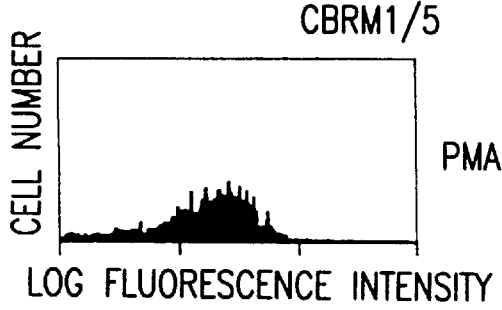
Figure 4P:
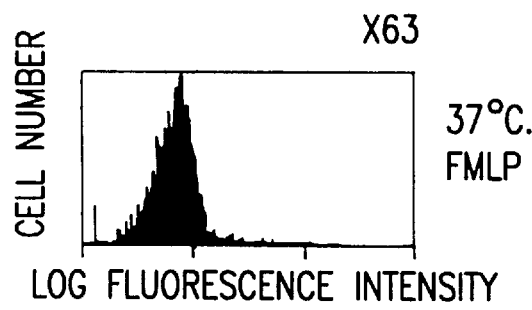
Figure 4Q:
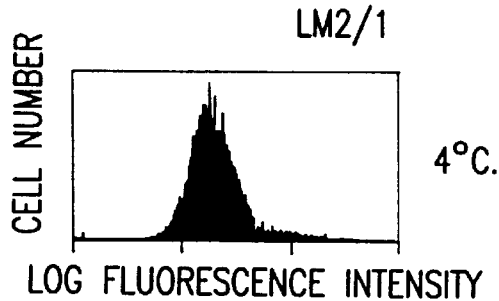
Figure 4U:
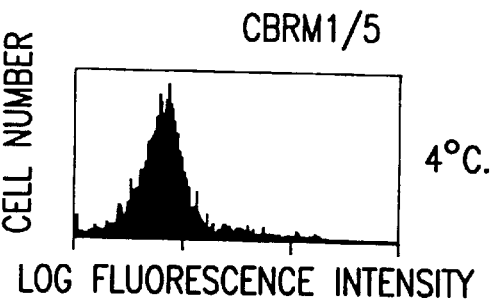
Figure 4R:
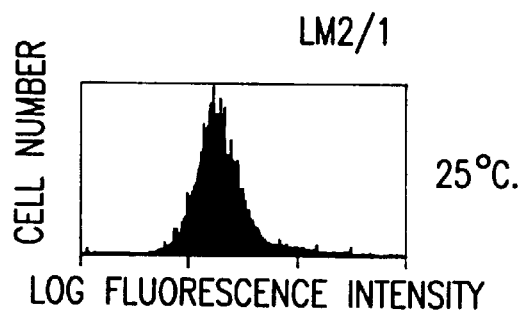
Figure 4V:
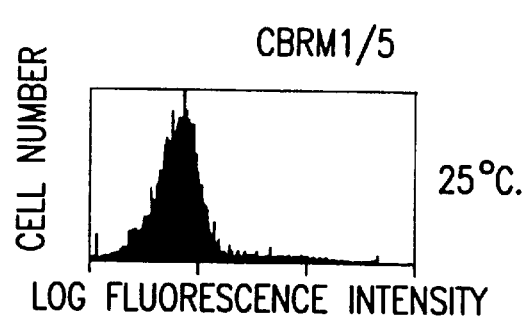
Figure 4S:
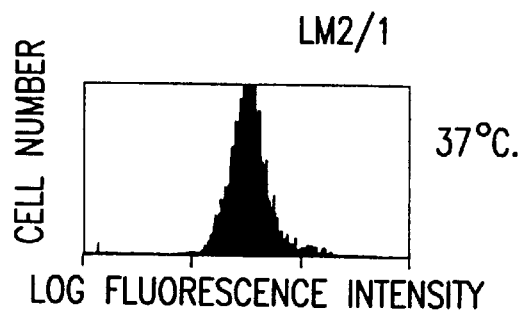
Figure 4W:
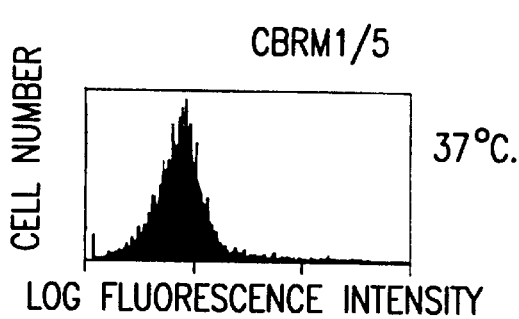
Figure 4T:
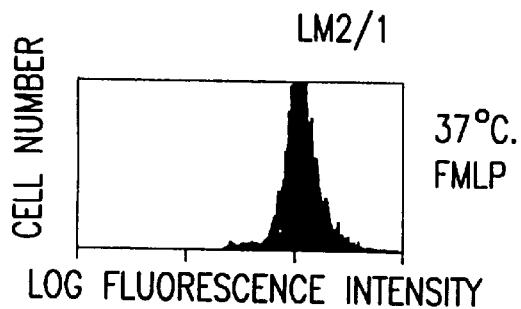
Figure 4X:
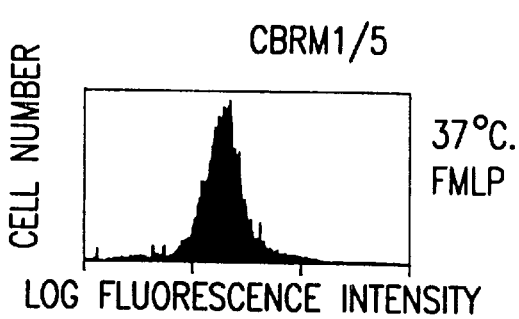

FIG. 4A–4X. The effect of temperature on Mac-1 expression on 4A–4L peripheral blood monocytes and FIGS. 4M–4X neutrophils. Cells were incubated at 4° C., 25° C., and 37° C. in the absence or presence of stimuli (fMLP, $10^{31}$ 7MPMA, 100 ng/ml) for ten minutes, and then immunostained with either a negative control (X63), a MAb to Mac-1 α subunit (LM2/1), or CBRM1/5. Representative histograms show the log fluorescence intensity versus cell number.

Figure 5A:
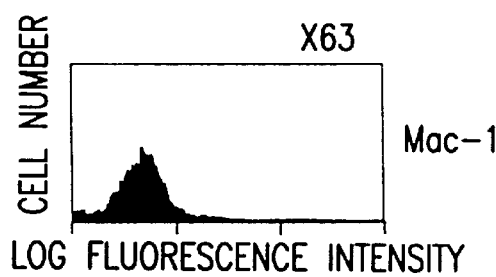
Figure 5E:
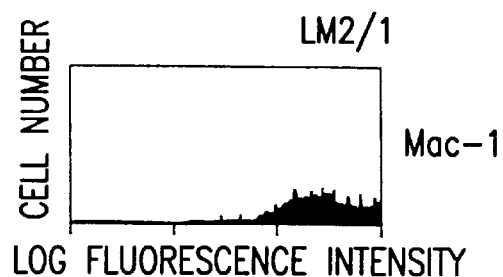
Figure 5B:
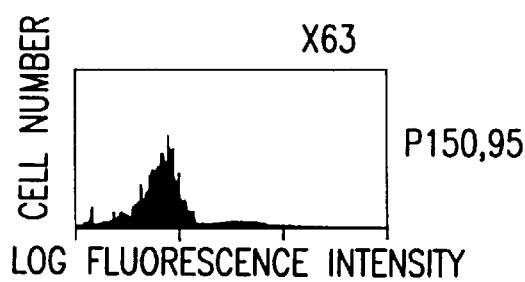
Figure 5F:
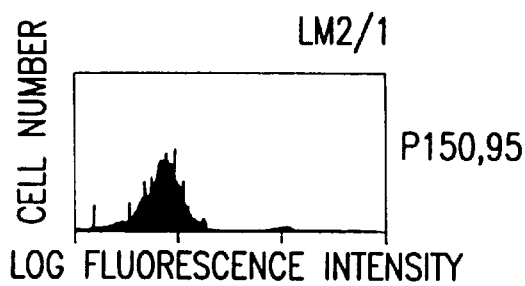
Figure 5C:
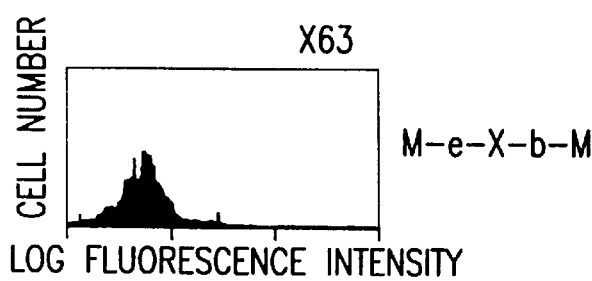
Figure 5G:
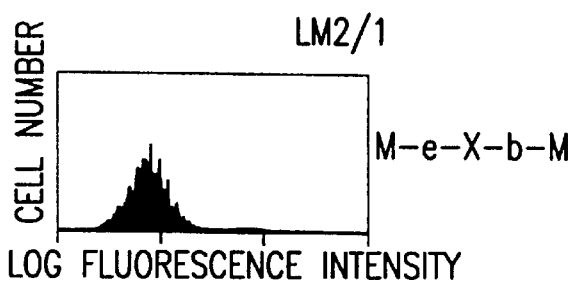
Figure 5D:
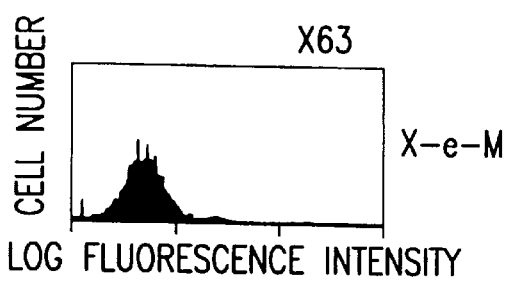
Figure 5H:
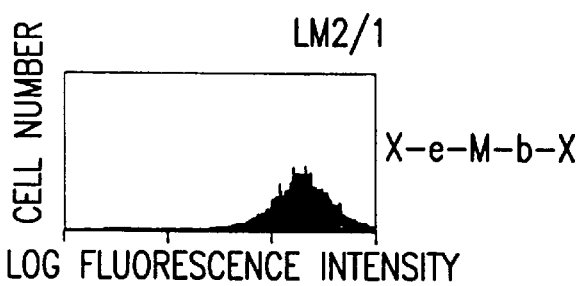
Figure 5I:
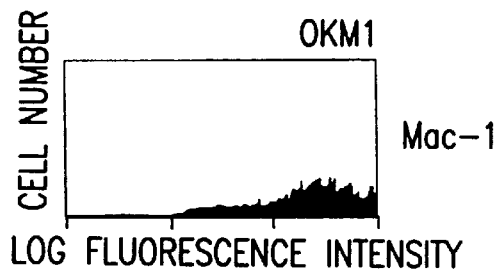
Figure 5M:
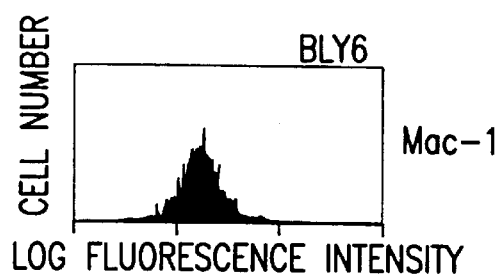
Figure 5J:
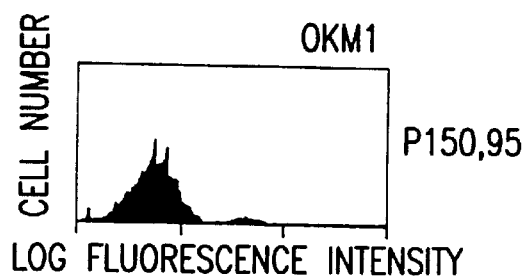
Figure 5N:
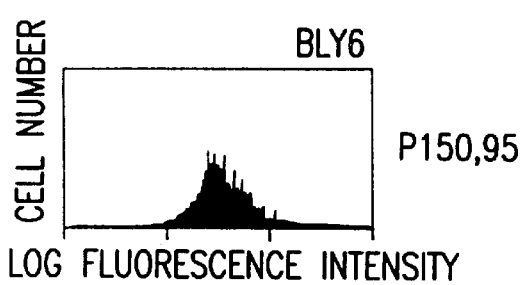
Figure 5K:
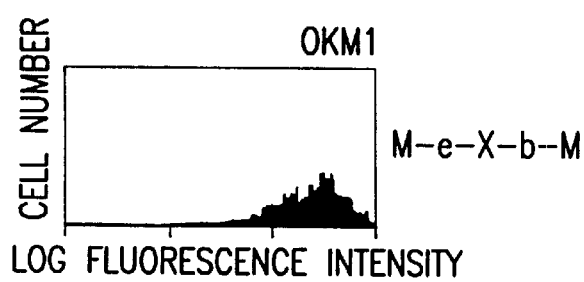
Figure 5O:
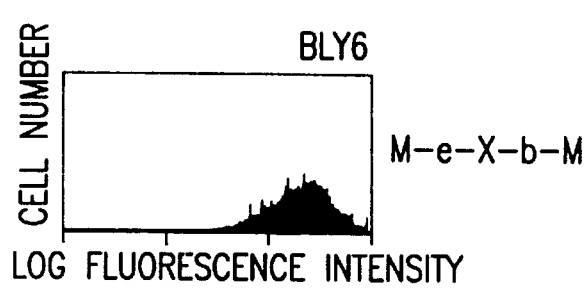
Figure 5L:
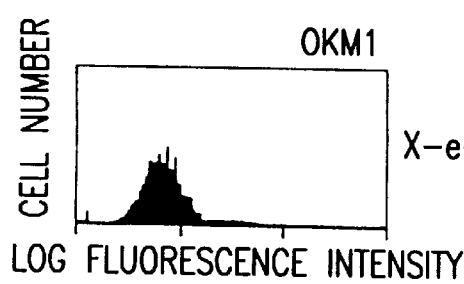
Figure 5P:
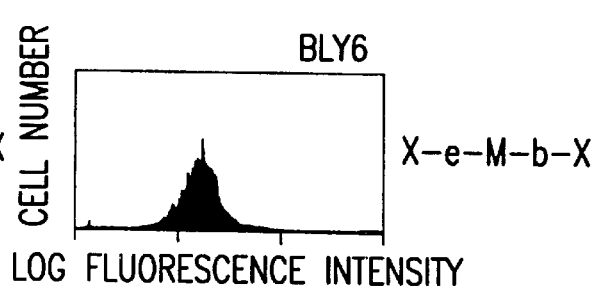
Figure 5Q:
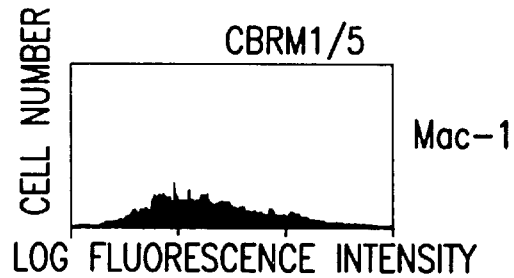
Figure 5R:
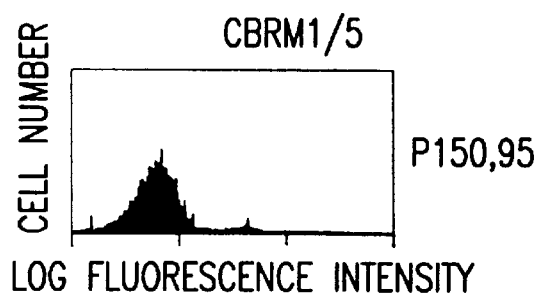
Figure 5S:
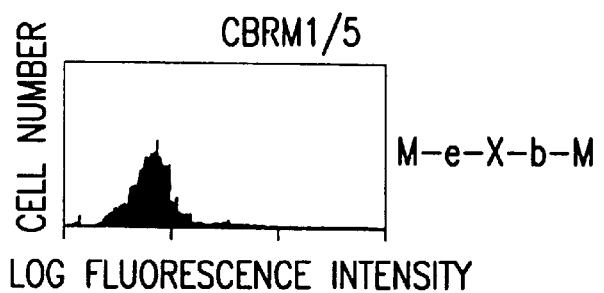
Figure 5T:
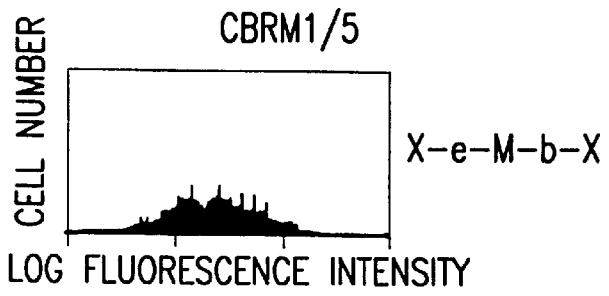
Figure 6:
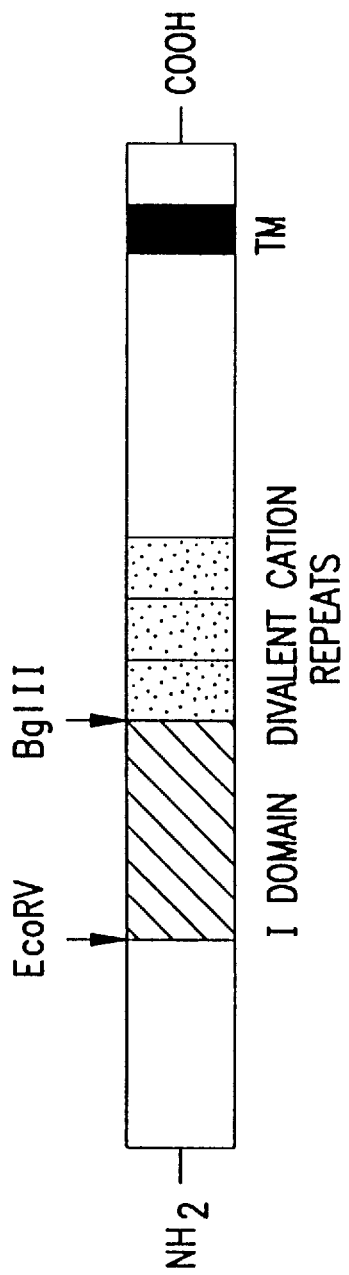

FIG. 5A–5T. Schematic representation and flow cytometric analyses of Mac-1/p150,95 chimeric molecules. A, MAbs used for the flow cytometry were X63 (non-binding control), LM2/1 (anti-Mac-1 α), OKM1 (anti-Mac-1α), BLY6 (anti-p150,95 α) and CBRM1/5. Representative histograms show the log fluorescence intensity versus cell number. FIG. 6, Chimeric molecules were constructed by the ligation of fragments from either p150,95 or Mac-1 cDNA, and expressed stably in CHO cells. Those parts of the chimers from Mac-1 are represented by open bars, those from p150,95 are represented by shaded bars. The region from the EcoRV to the BglII restriction site constitutes the I domain.

Figure 7A:
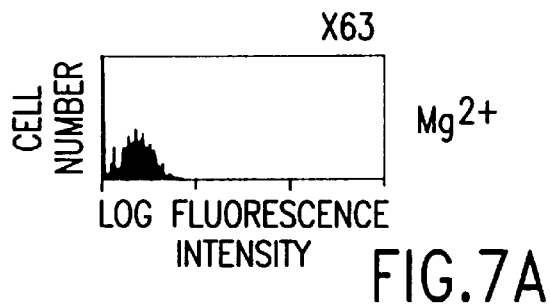
Figure 7E:
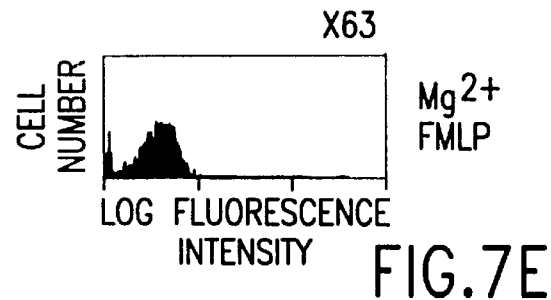
Figure 7B:
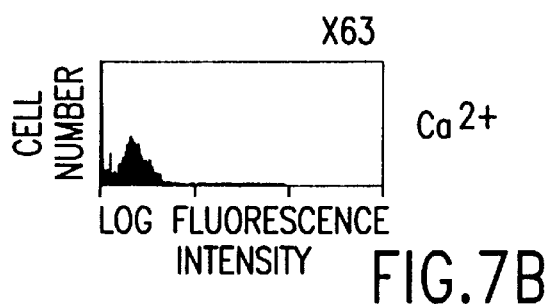
Figure 7F:
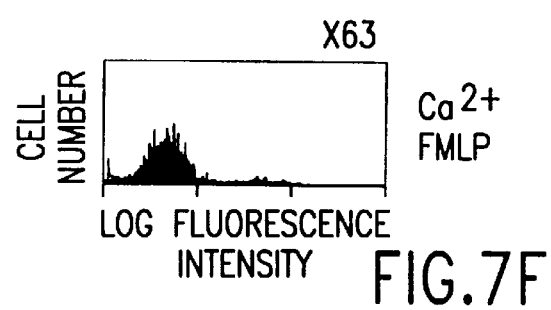
Figure 7C:
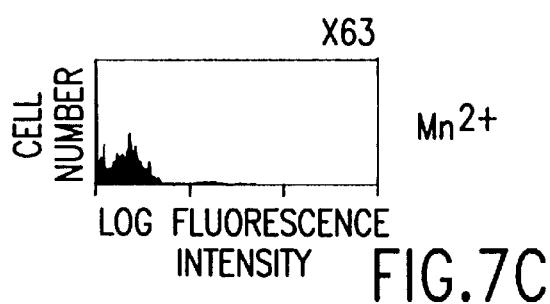
Figure 7G:
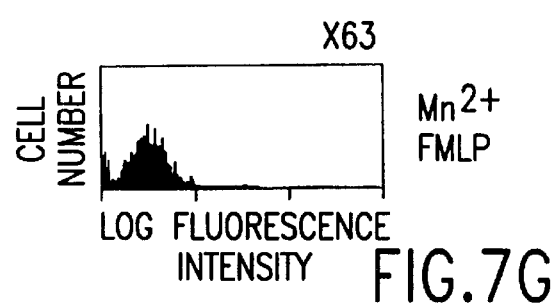
Figure 7D:
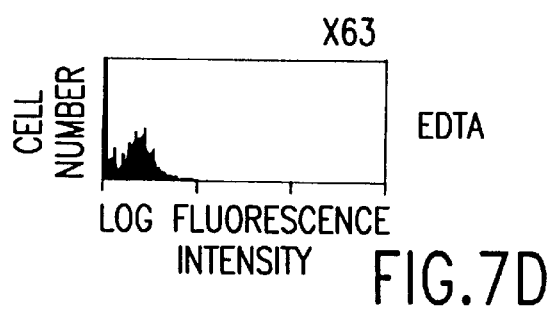
Figure 7H:
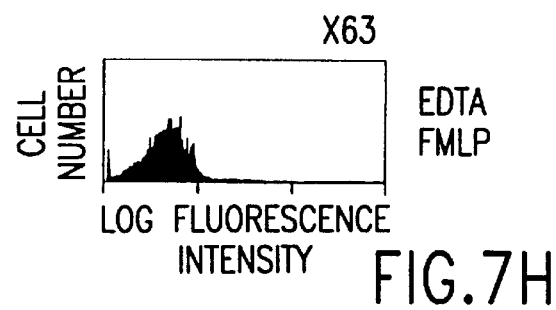
Figure 7I:
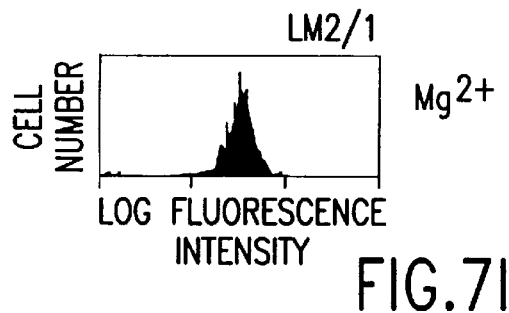
Figure 7M:
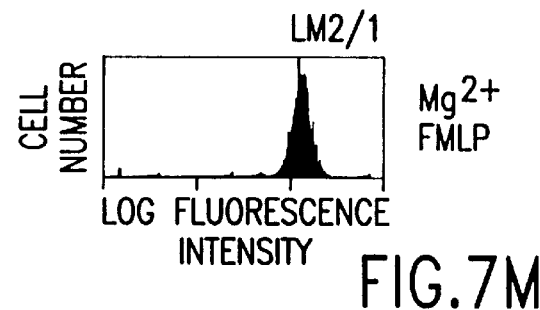
Figure 7J:
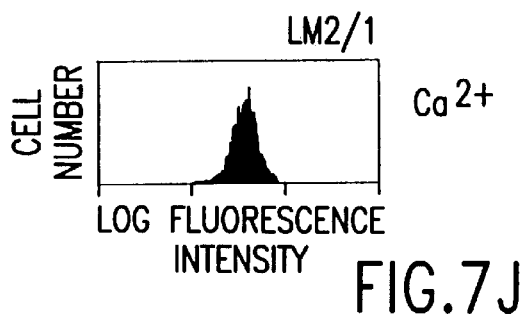
Figure 7N:
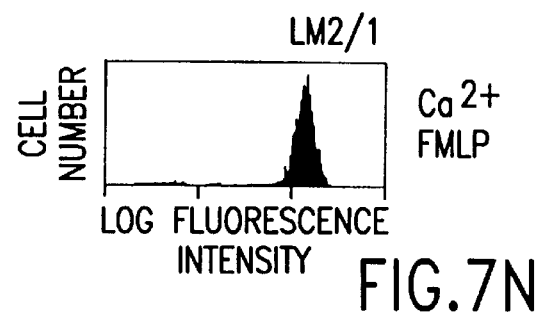
Figure 7K:
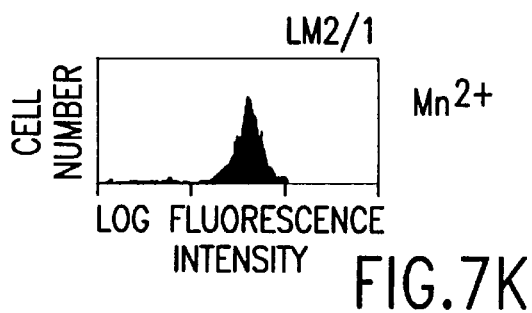
Figure 7O:
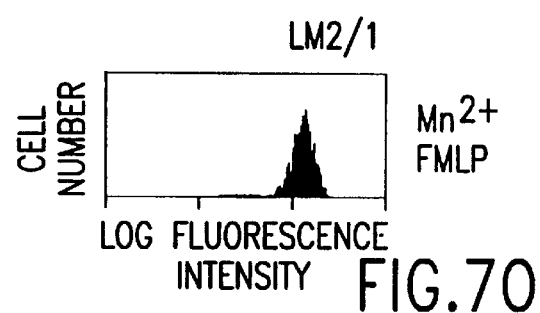
Figure 7L:
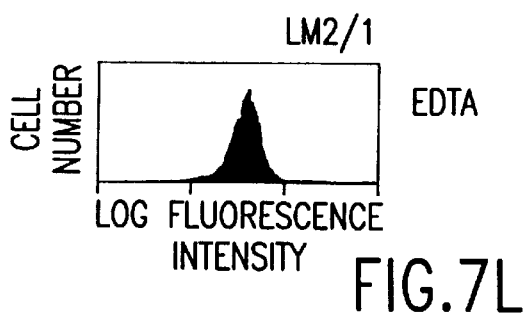
Figure 7P:
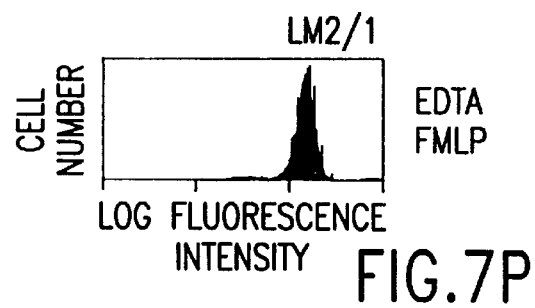
Figure 7Q:
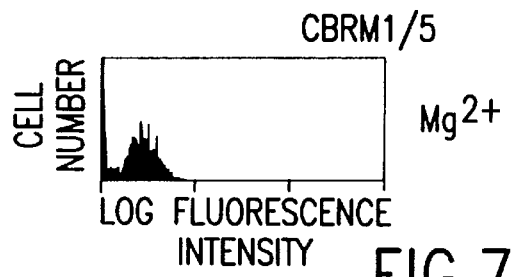
Figure 7U:
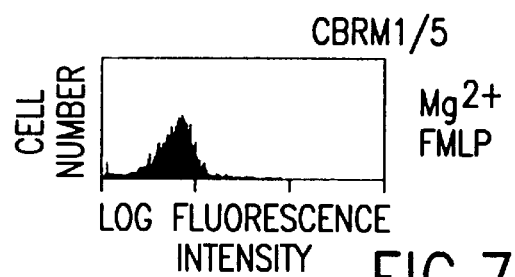
Figure 7R:
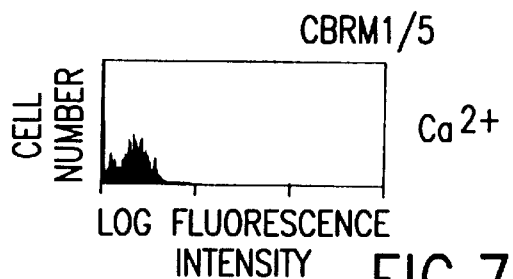
Figure 7V:
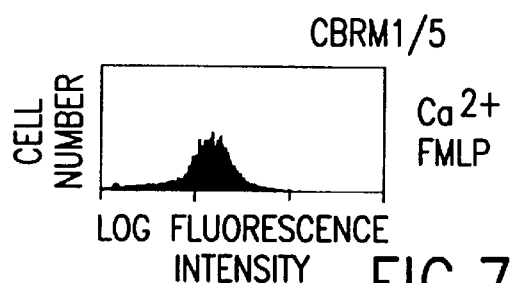
Figure 7S:
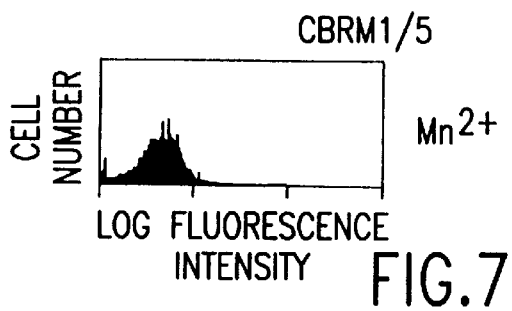
Figure 7W:
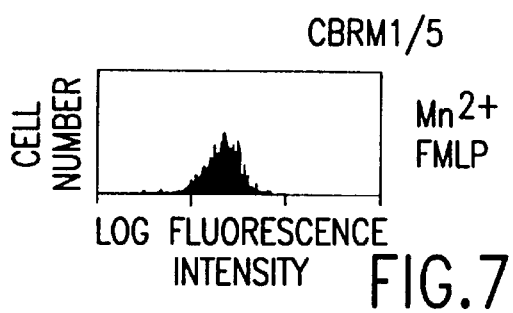
Figure 7T:
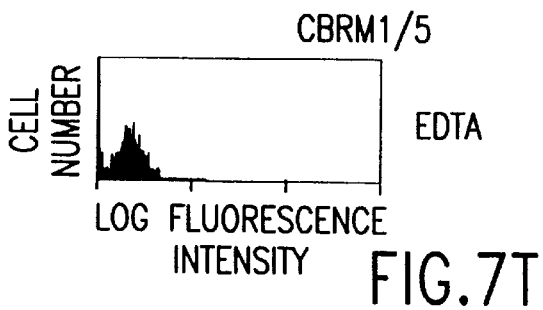
Figure 7X:
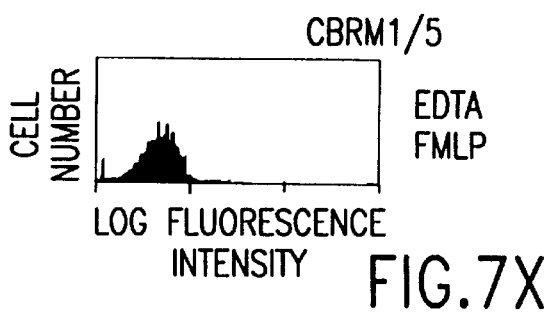
Figure 8:
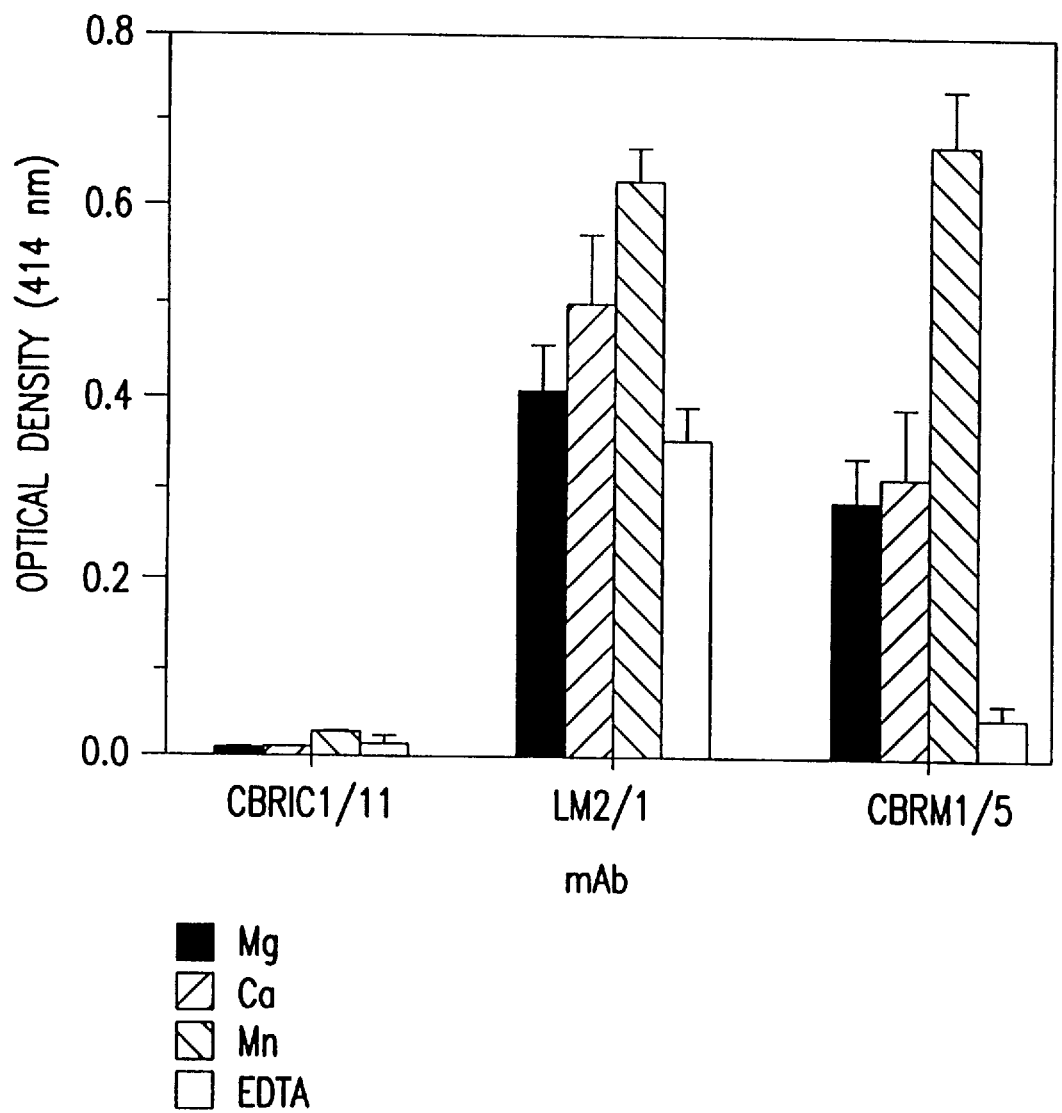

FIGS. 7A–7X. Divalent cations affect expression of Mac-1 MAb epitopes. Neutrophils were incubated at 4° C. (resting) and 37° C. (fMLP, $10^{-7}$M) for ten minutes in HBSS that was supplemented by the indicated divalent cation or chelating agent. Cells were immunostained with either a negative control (X63), a MAb to Mac-1 α subunit (LM2/1), or CBRM1/5. All subsequent washes were performed in the presence of the indicated divalent cation. Representative histograms show the log fluorescence intensity versus cell number. FIG. 8, Purified Mac-1 was adsorbed to plastic and non-specific sites were blocked after sequential washes with HSA and TWEEN 20 in the presence of the indicated divalent cation (see Materials and Methods). Solid-phase Mac-1 was incubated with MAbs (CBRIC1/11, anti-ICAM-1; LM2/1, anti-Mac-1 α; CBRM1/5, anti-Mac-1α) and developed by an ELISA with horseradish peroxidase couple goat anti-mouse IgG. This representative experiment was performed in triplicate and the bars indicate the standard error of the mean.

Figure 9:
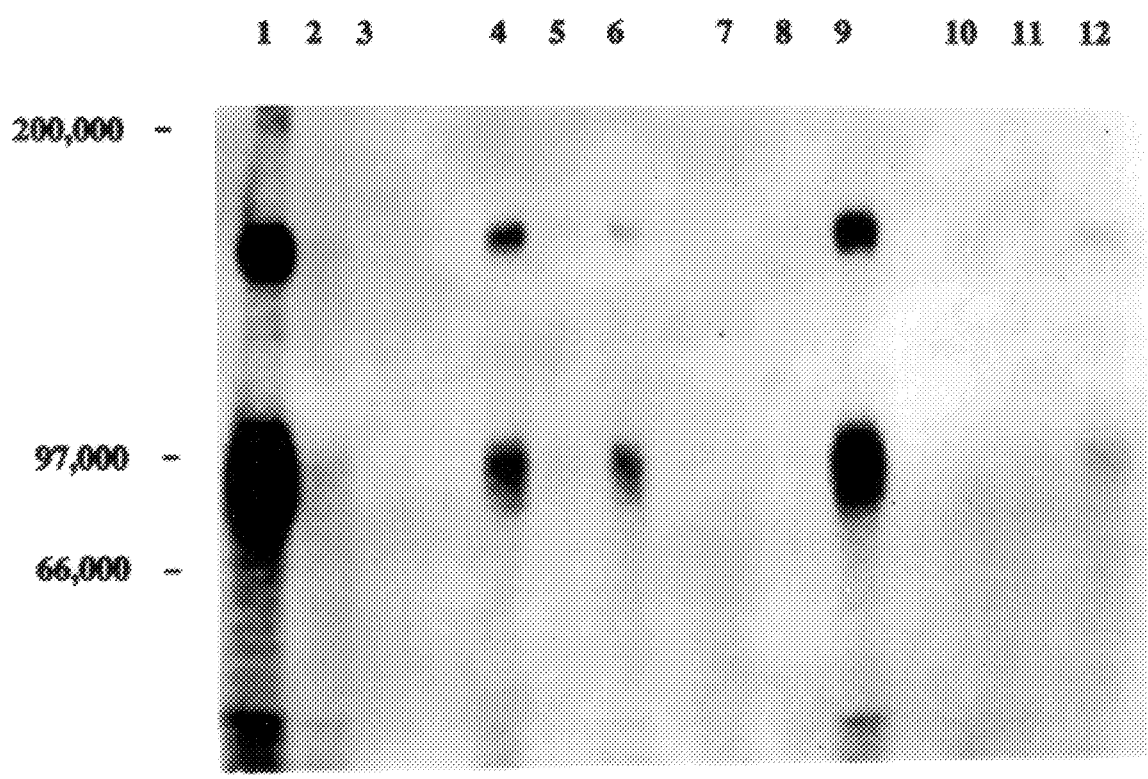

FIG. 9. SDS-5% PAGE analysis of immunoprecipitates from neutrophil lysates. Iodinated neutrophils were lysed in 1% TRITON-X-100 and aliquots (60 μl, 1:4 dilution) were incubated with directly coupled Sepharose (Lane 1, LM2/1; Lane 4, CBRM1/5; Lanes 7 and 10, Mouse IgG) for 2h at 4° C. The beads were pelleted, the pre-cleared supernatants were retrieved and reprecipitated with additional directly coupled Sepharose (Lane 2, LM2/1; Lane 5, CBRM1/5; Lanes 8 and 11, Mouse IgG) for 2h at 4° C. After pelleting, the supernatants were again collected but the LM2/1 precleared lysate was precipitated with CBRM1/5 (Lane 3), the CBRM1/5 precleared lysate was precipitated with LM2/1 (Lane 6), and the mouse IgG precleared lysates were precleared with LM2/1 (Lane 9) or CBRM1/5 (Lane 12). Material eluted from the beads was run under reducing conditions and subjected to autoradiography. Molecular weight standards are shown at the left.

Figure 10A:
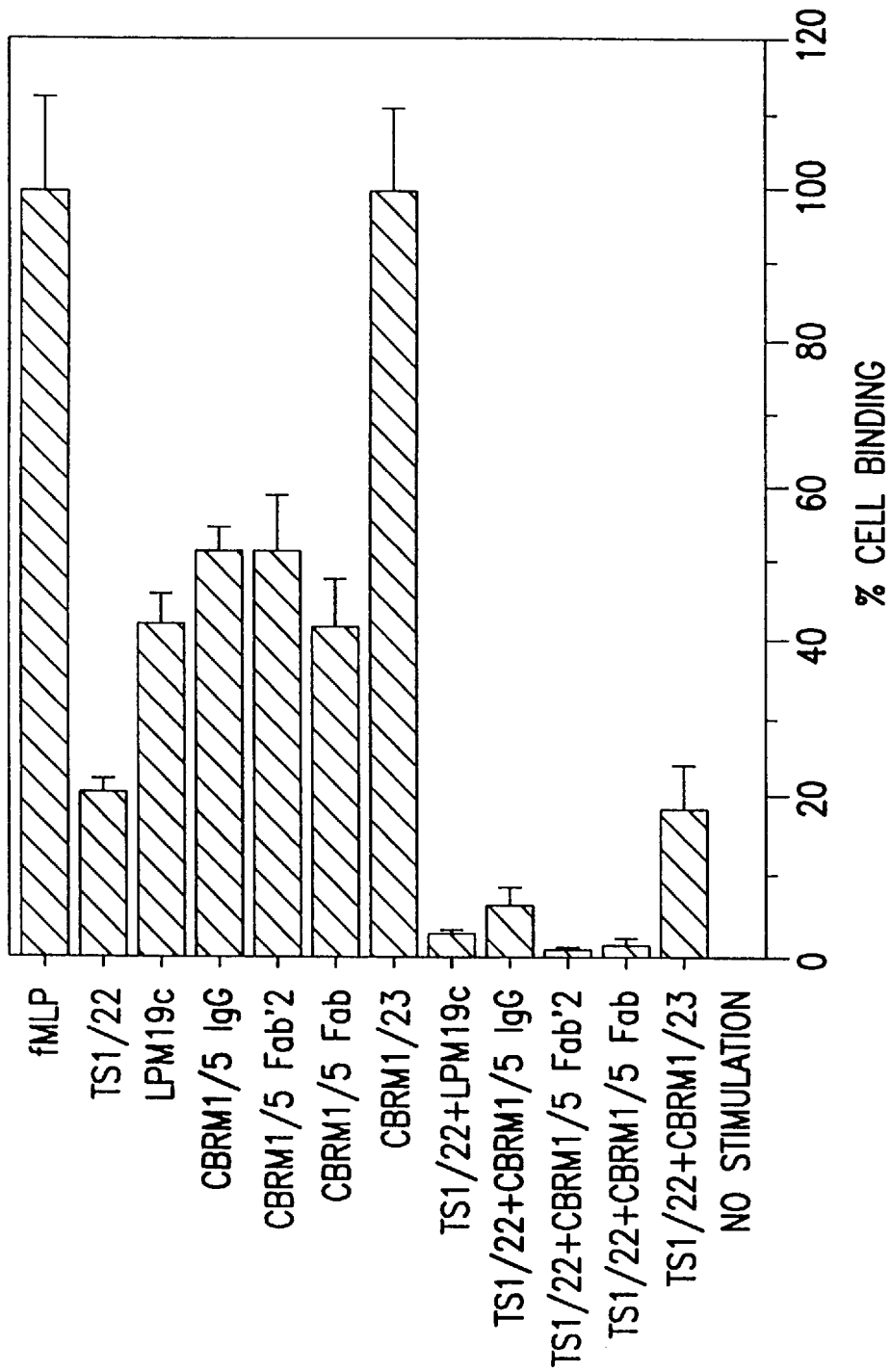
Figure 10B:
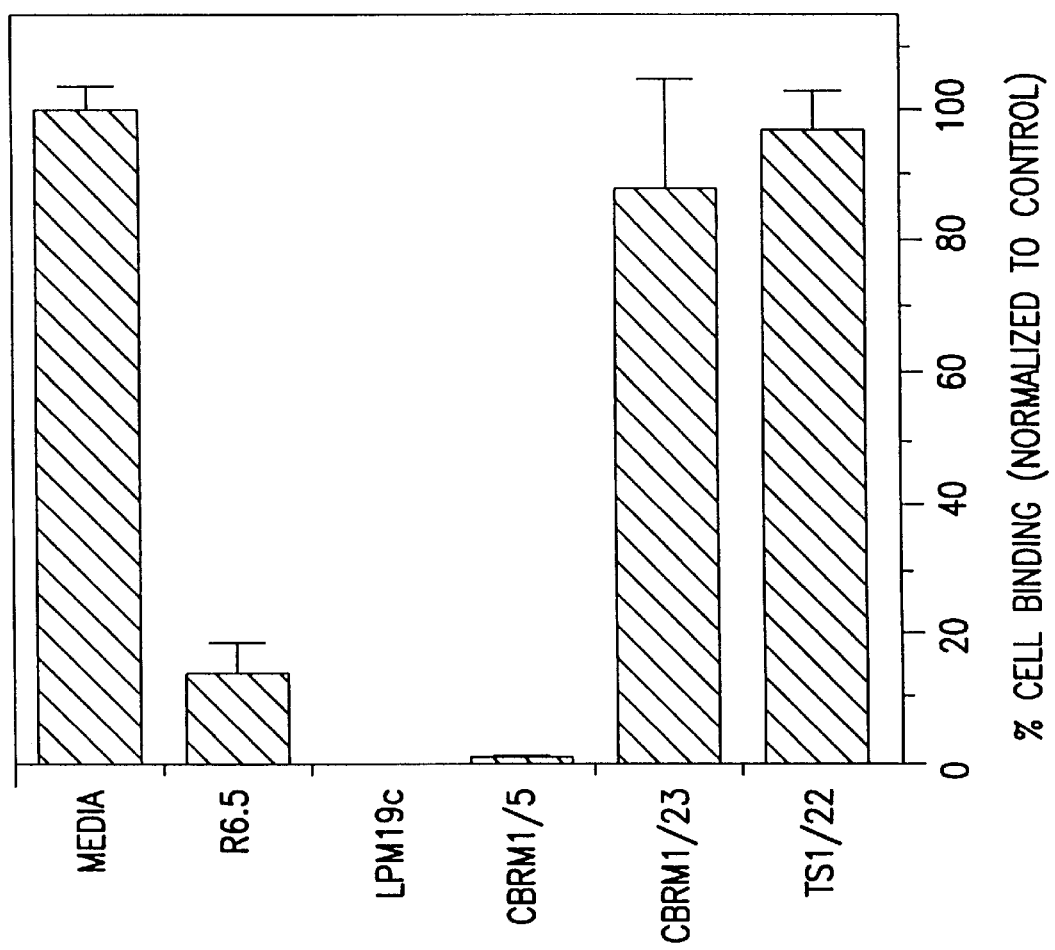
Figure 10C:
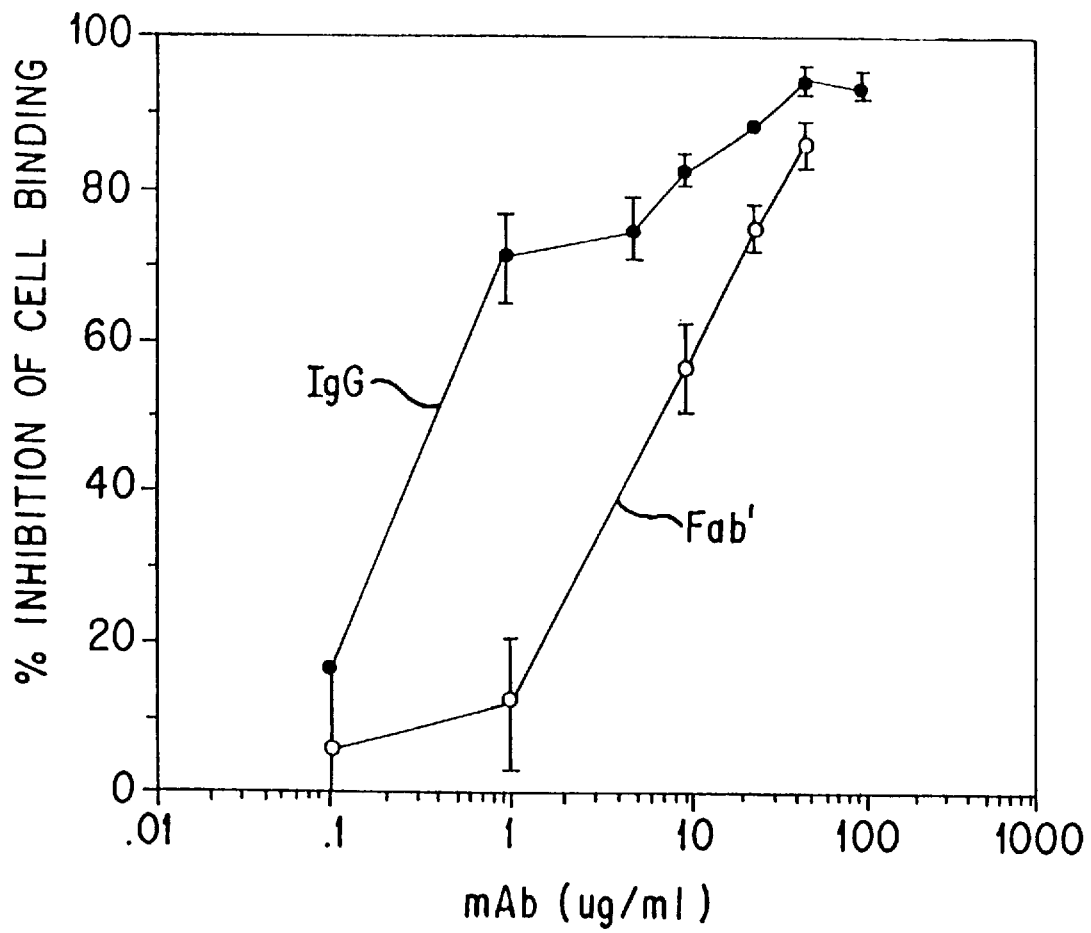

FIGS. 10A–10C. The effect of CBRM1/5 on neutrophil adhesion to its ligands. FIG. 10A. Neutrophils were allowed to bind to purified sICAM-1 in 6 cm Petri dishes for four minutes at room temperature in the presence of fMLP ($10^{-7}$M) after a ten minute preincubation with the following MAbs: TS1/22 (anti-LFA-1 α, 1/250 dilution of ascites), LPM19c (anti-Mac-1 α, 1/250 dilution of ascites), CBRM1/5 (anti-Mac-1 α, 25 μg/ml IgG and Fab'$_2$; 50 μg/ml Fab), CBRM1/23 (anti-Mac-1 α, 25 μg/ml). FIG. 10B. The effect of CBRM1/5 on ICAM-1$^+$L cell adhesion to purified Mac-1. ICAM-1$^+$L cells were allowed to bind to purified Mac-1 in 6 cm Petri dishes for 60 minutes at 37° C. after a 25 minute preincubation with the following MAbs: TS1/22 (anti-LFA-1 α), LPM19c (anti-Mac-1 α), CBRM1/5 (anti-Mac-1 α), and CBRM1/23 (anti-Mac-1 α). Data is expressed as the percent cell binding relative to a media control. Datapoints are the average of five microscopic fields and the bars indicate the standard error of the mean. FIG. 10C, Dose dependent inhibition of neutrophil binding to fibrinogen by CBRM1/5. Neutrophils were allowed to bind to purified fibrinogen in 6 cm Petri dishes for four minutes at room temperature in the presence of fMLP ($10^{-7}$M) after a ten minute preincubation increasing concentrations of CBRM1/5 IgG or Fab. The binding was determined by light microscopy (40x) after the unbound cells were removed by serial washes with a Pasteur pipette. Data is expressed as the percent inhibition of cell binding relative to a media control. Datapoints are the average of five microscopic fields and the bars indicate the standard error of the mean. The graphs are representative experiments that were repeated several times.

Figure 11A:
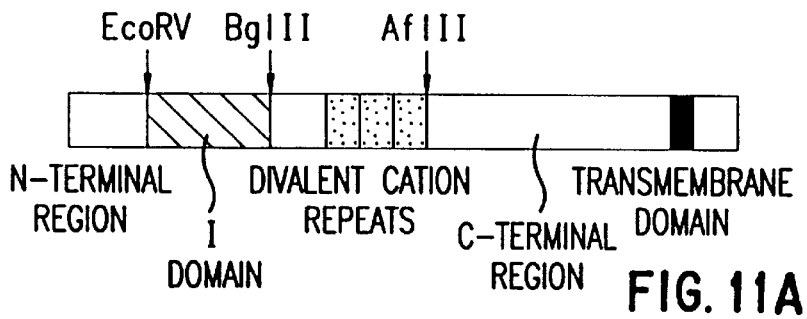
Figure 11B:
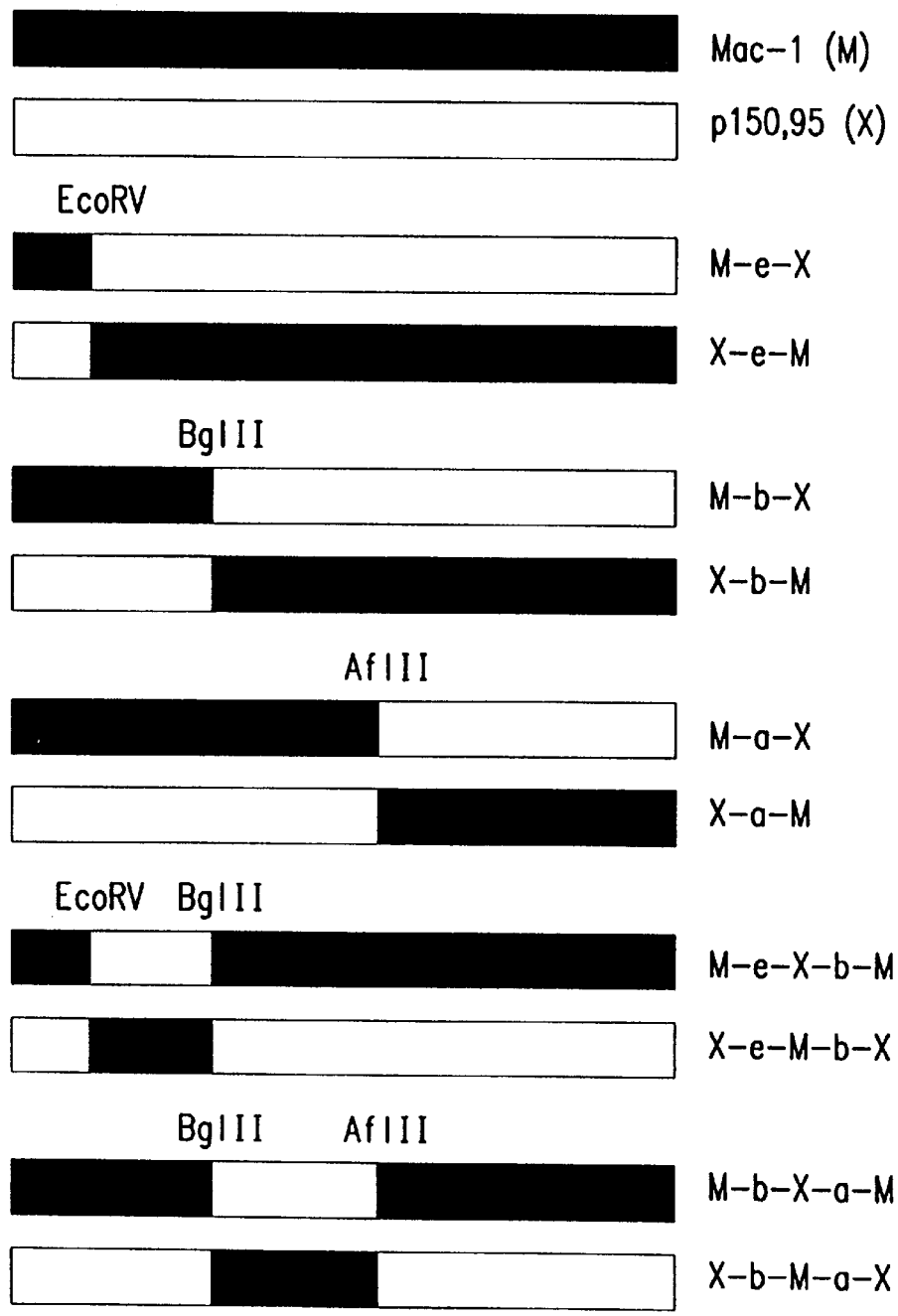
Figure 12A:
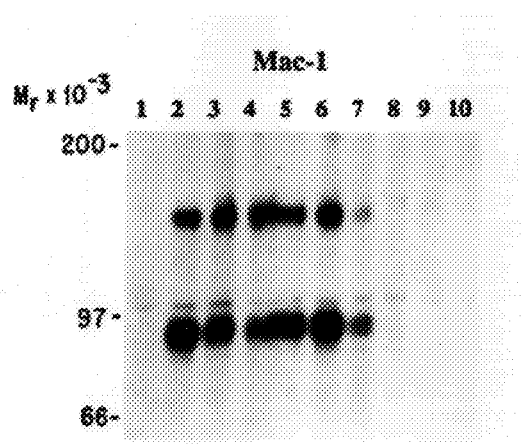
Figure 12B:
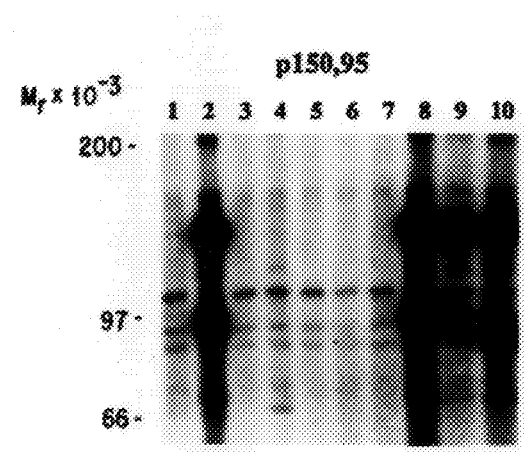
Figure 12C:
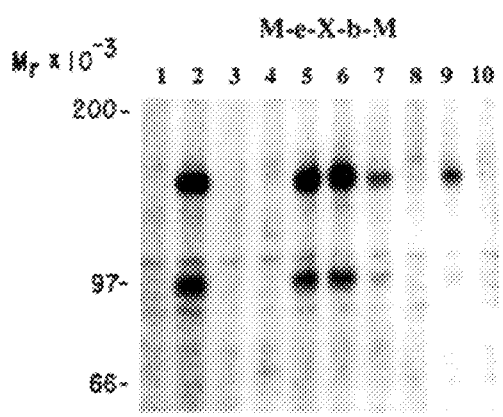
Figure 12D:
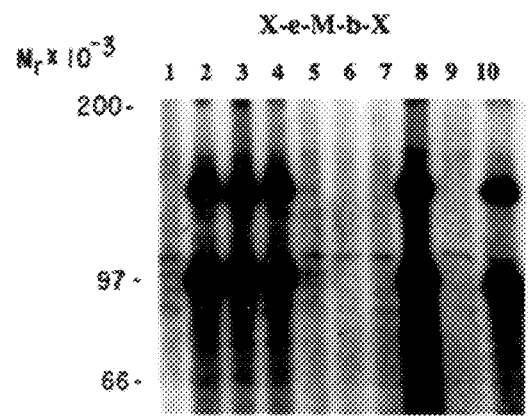

FIGS. 11A–11B. Schematic representation of the leukocyte integrin α chain (FIG. 11A and Mac-1/p150,95 chimeras (FIG. 11B). Restriction sites (e, EcoRV; b, BglII; a, AflII) that facilitated reciprocal exchanges are indicated with arrows or in the name of each chimera.

FIGS. 12A–12D. SDS-PAGE of Mac-1, p150,95 or Mac-1/p150,95 chimeras immunoprecipitated from $^{125}$I-COS cell detergent lysates. COS cells were cotransfected with the β subunit and (A) Mac-1, (B) p150,95, (C) M-e-X-b-M, or (D) X-e-M-b-X cDNA, surface labelled with $^{125}$I, and immunoprecipitated with the X63 (Lane 1, negative control), TS1/18 (Lane 2, anti-CD18), LM2/1 (Lane 3, anti-CD11b), Mn41 (Lane 4, anti-CD11b), VIM12 (Lane 5, anti-CD11b), OKM1 (Lane 6, anti-CD11b), OKM10$_{old}$ (Lane 7, anti-CD11b), SHCL3 (Lane 8, anti-CD11c), BLY6 (Lane 9, anti-CD11c), L29 (Lane 10, anti-CD11c) as described in the Materials and Methods. Material was boiled in SDS sample buffer with 5% β-mercaptoethanol, electrophoresed on a 7% polyacrylamide gel, and autoradiographed. Molecular weights of the protein standards are indicated in the center.

Figure 13A:
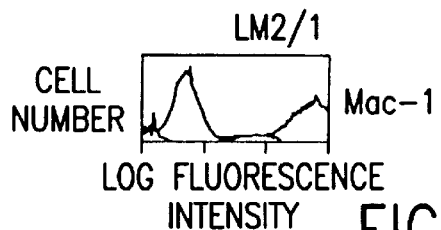
Figure 13G:
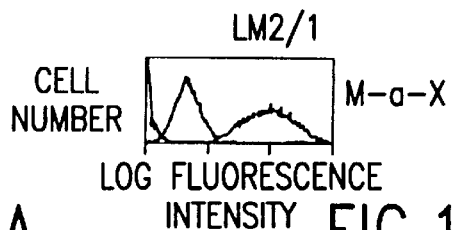
Figure 13B:
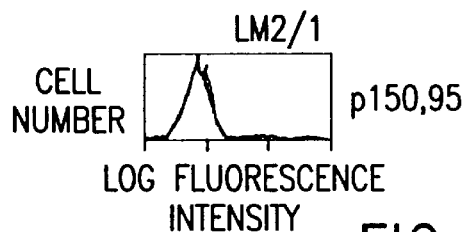
Figure 13H:
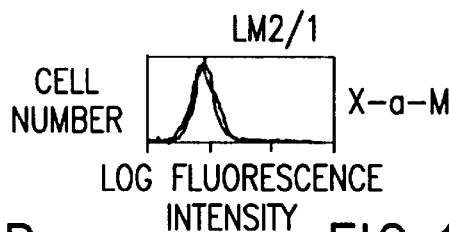
Figure 13C:
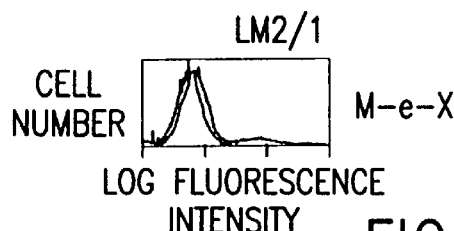
Figure 13I:
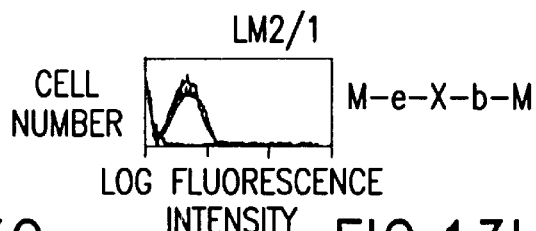
Figure 13D:
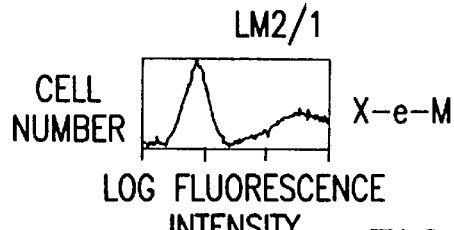
Figure 13J:
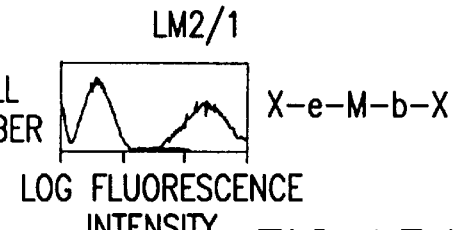
Figure 13E:
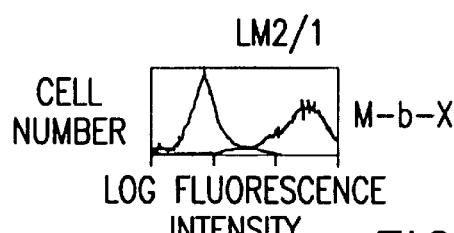
Figure 13K:
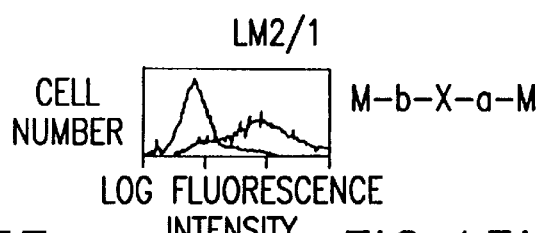
Figure 13F:
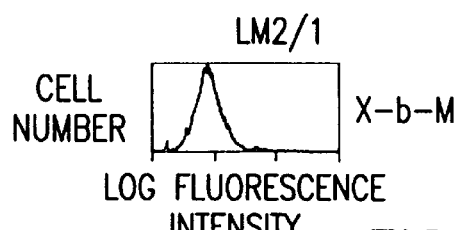
Figure 13L:
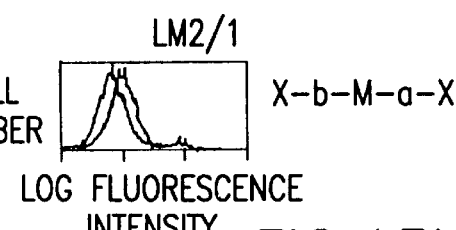
Figure 13M:
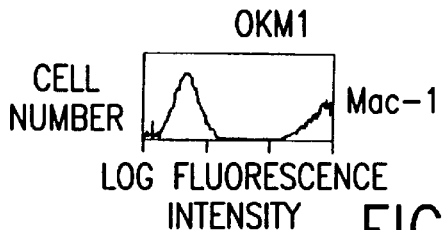
Figure 13S:
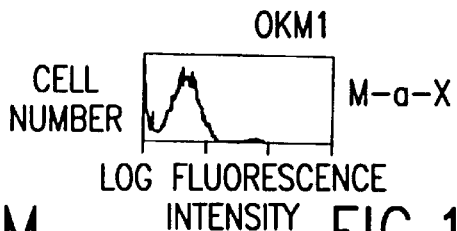
Figure 13N:
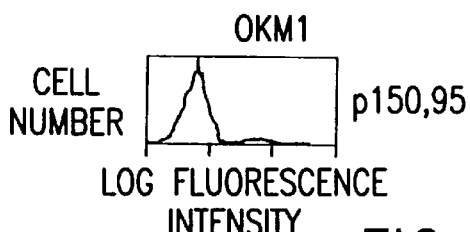
Figure 13T:
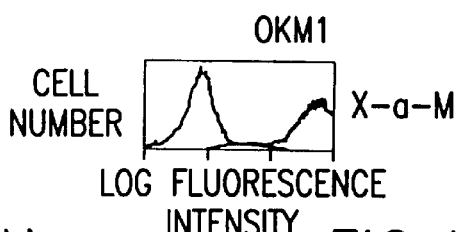
Figure 13O:
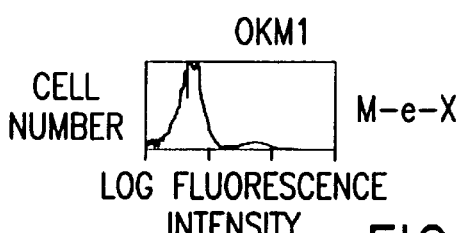
Figure 13U:
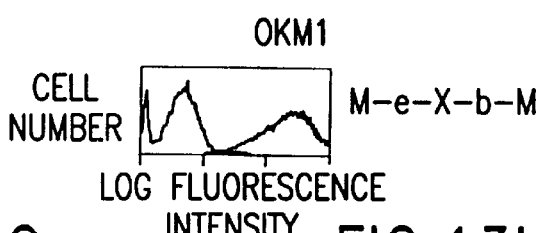
Figure 13P:
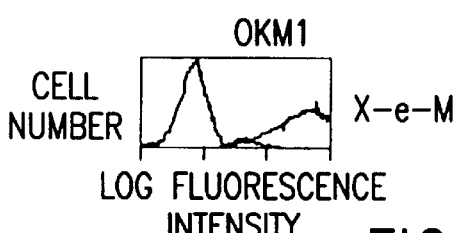
Figure 13V:
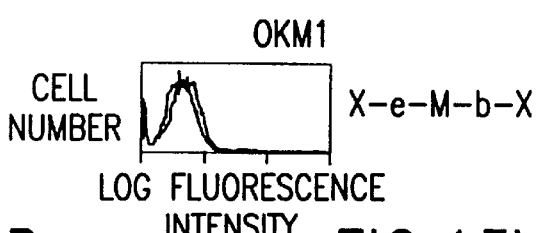
Figure 13Q:
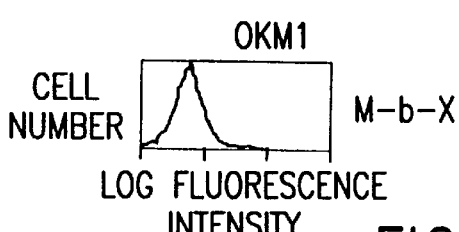
Figure 13W:
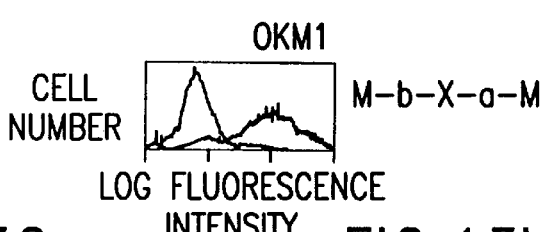
Figure 13R:
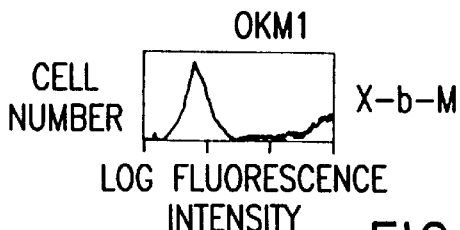
Figure 13X:
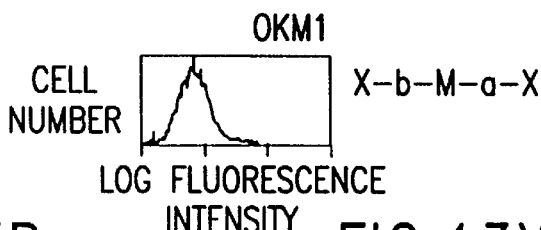
Figure 13Y:
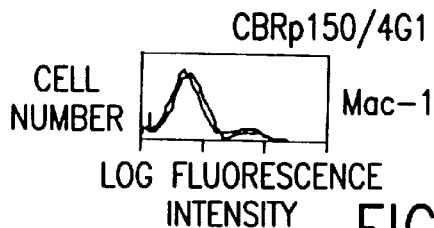
Figure 13E:
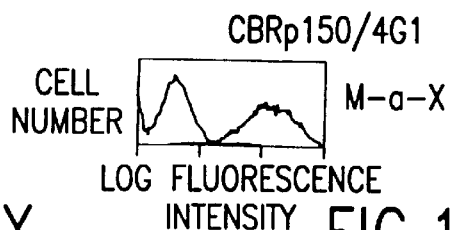
Figure 13Z:
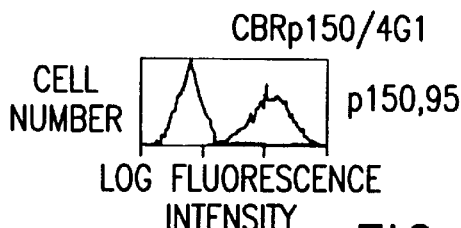
Figure 13F:
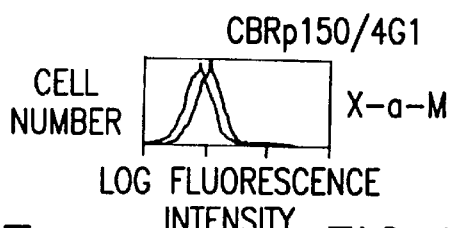
Figure 13A:
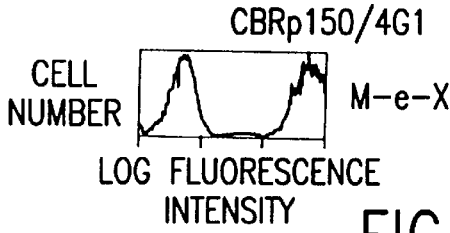
Figure 13G:
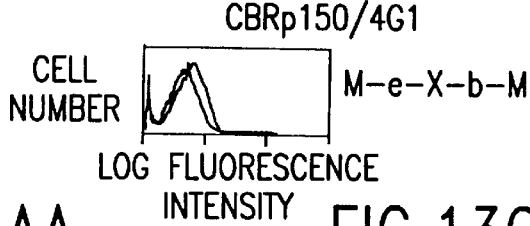
Figure 13B:
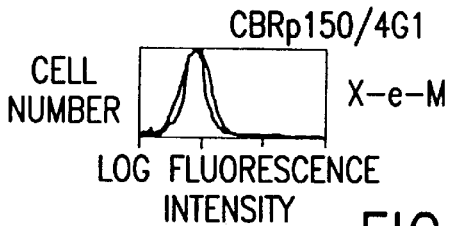
Figure 13H:
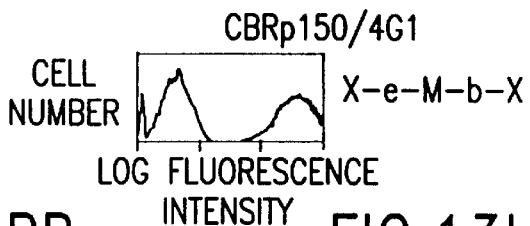
Figure 13C:
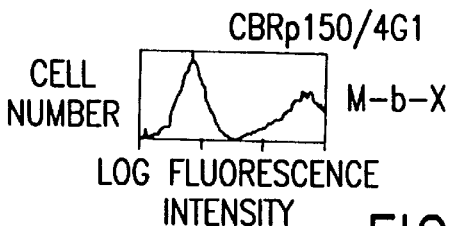
Figure 13I:
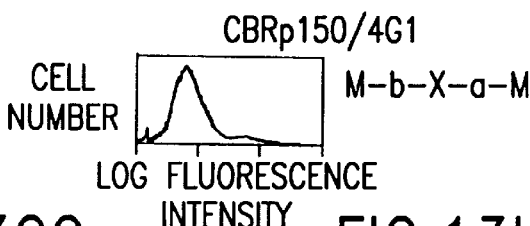
Figure 13D:
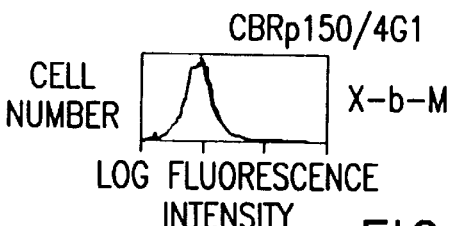
Figure 13J:
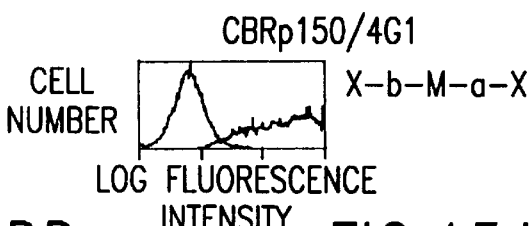
Figure 13K:
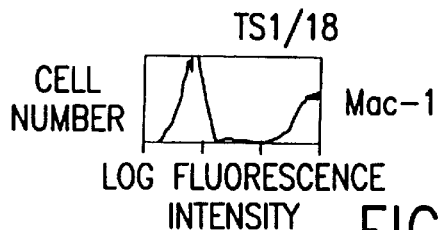
Figure 13Q:
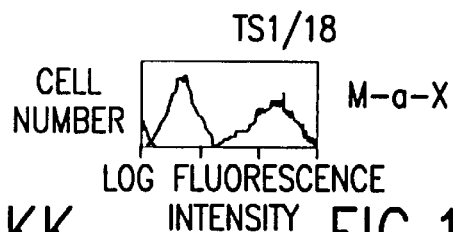
Figure 13L:
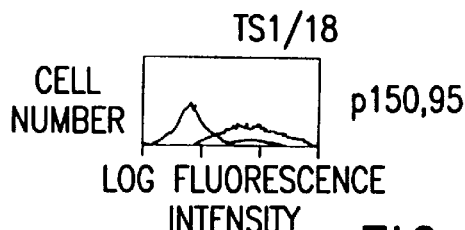
Figure 13R:
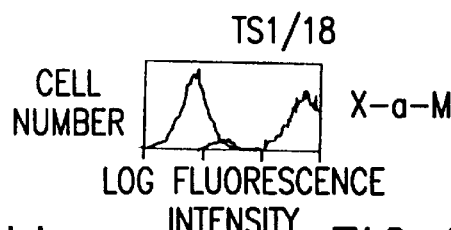
Figure 13M:
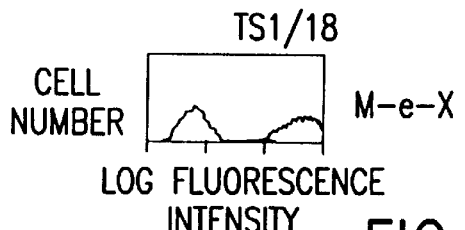
Figure 13S:
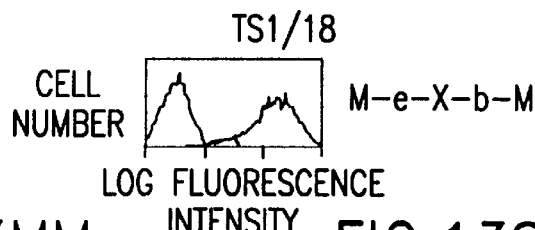
Figure 13N:
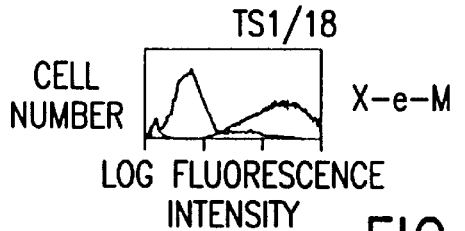
Figure 13T:
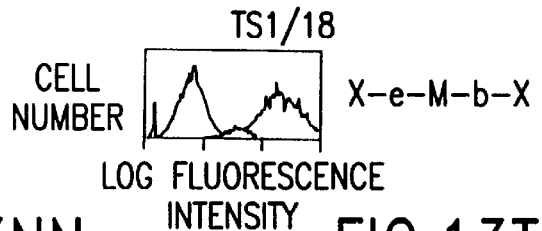
Figure 13O:
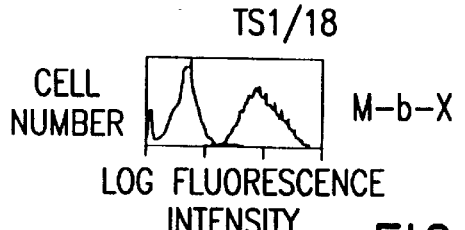
Figure 13U:
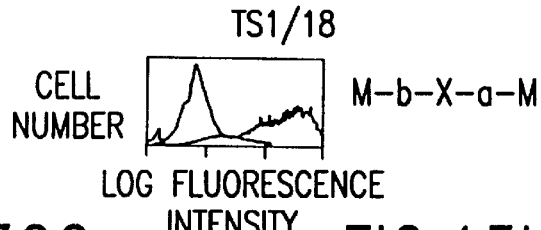
Figure 13P:
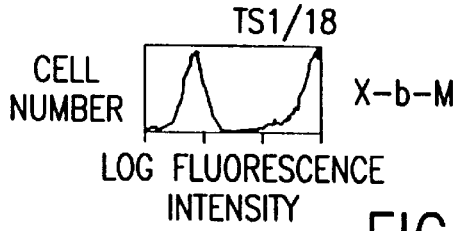
Figure 13V:
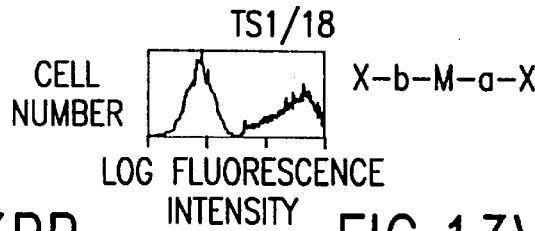

FIGS. 13A–13VV. Flow cytometry profiles of CHO cells expressing Mac-1, p150,95 and Mac-1/p150,95 chimeras. CHO cell transfectants (as indicated) were immunostained with either a negative control (X63), a MAb to the I domain (LM2/1) or C-terminal (OKM1) region of the Mac-1 α subunit, a MAb to the C-terminal region of the p150,95 α subunit (CBRp150/4G1), or a MAb to the CD18 β subunit (TS1/18). Cells were subjected to immunofluorescent flow cytometry. Each histogram shows the negative control (X63, light line) and the MAb indicated at the top of the column (dark line).

Figure 14:
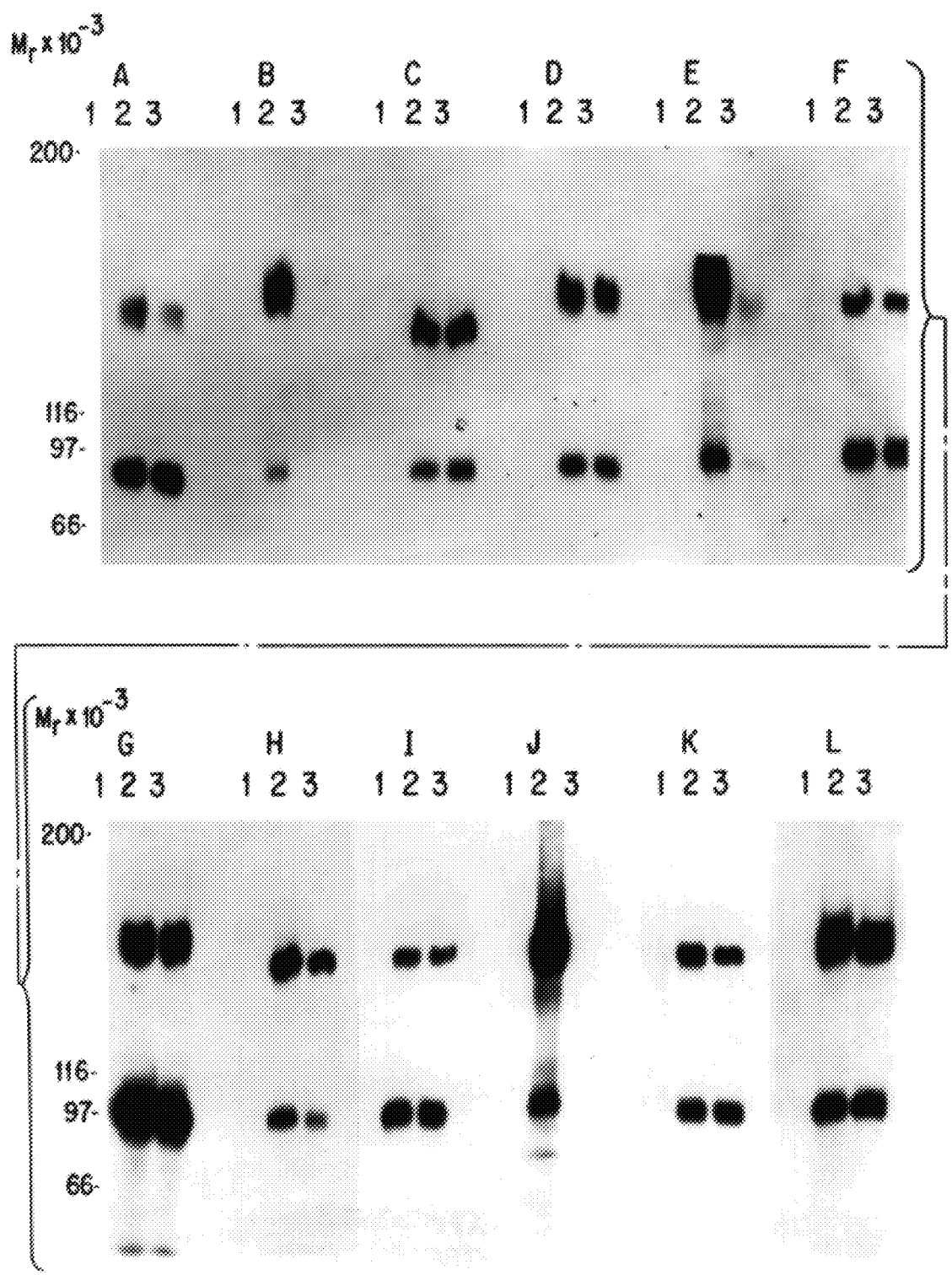

FIG. 14. SDS-PAGE of Mac-1, p150,95 or Mac-1/p150, 95 chimera immunoprecipitated from $^{125}$I-CHO cell detergent lysates. CHO cells transfectants (A) Mac-1, (B) X-e-M, (C) M-e-X, (D) X-a-M, (E) X-b-M, (F) X-e-M-b-X, (G) M-b-X-a-M, (H) p150,95, (I) M-b-X, (J) X-b-M-a-X, (K) M-a-X, and (L) M-e-X-b-M were surface labelled with $^{125}$I, and immunoprecipitated with a negative control MAb (X63, Lane 1), a MAb to the I domain of Mac-1 (LM2/1, Lanes A2, B2, F2, I2 and K2), a MAb to the C-terminal region of Mac-1 (OKM1, Lanes D2, E2, G2 and L2), a MAb to the C-terminal region of p150,95 (CBRp150/4G1, Lanes C2, H2, J2), and a MAb to the CD18 β subunit (TS1/18, Lane 3) as described in the Materials and Methods. Material was boiled in SDS sample buffer with 5% β-mercaptoethanol, electrophoresed on a 5% polyacrylamide gel, and autoradiographed. Molecular weights of protein standards are indicated to the left.

FIGS. 15A–15B. Summary of MAb reactivity as determined by immunofluorescent flow cytometry with CHO cells transfected with wild type or chimeric Mac-1 and p150,95 molecules. (+++) indicates that 100% of cells stained the MAb with a pattern similar to that shown in FIG. 3. (+) indicates that 100% of cells stained positively with the MAb but with a significantly lower fluorescence intensity. (+/−) indicates that the MAb stained a subpopulation of cells of cells positively. (−) indicates that the MAb staining was not significantly different from the negative control (X63).

FIGS. 16A–16B. Summary of the functional effects of MAbs on Mac-1 interaction with ligands. The assays for the interaction with the four ligands are described in the Methods. The inhibition data with OKM10$_{old}$ was obtained from iC3b binding to transfected COS cells instead of neutrophils. The data is expressed as the percent inhibition by each MAb and is the average of at least three independent experiments. Standard error of the means are indicated after the±sign. ND indicates that the value was not determined.

Figure 17:
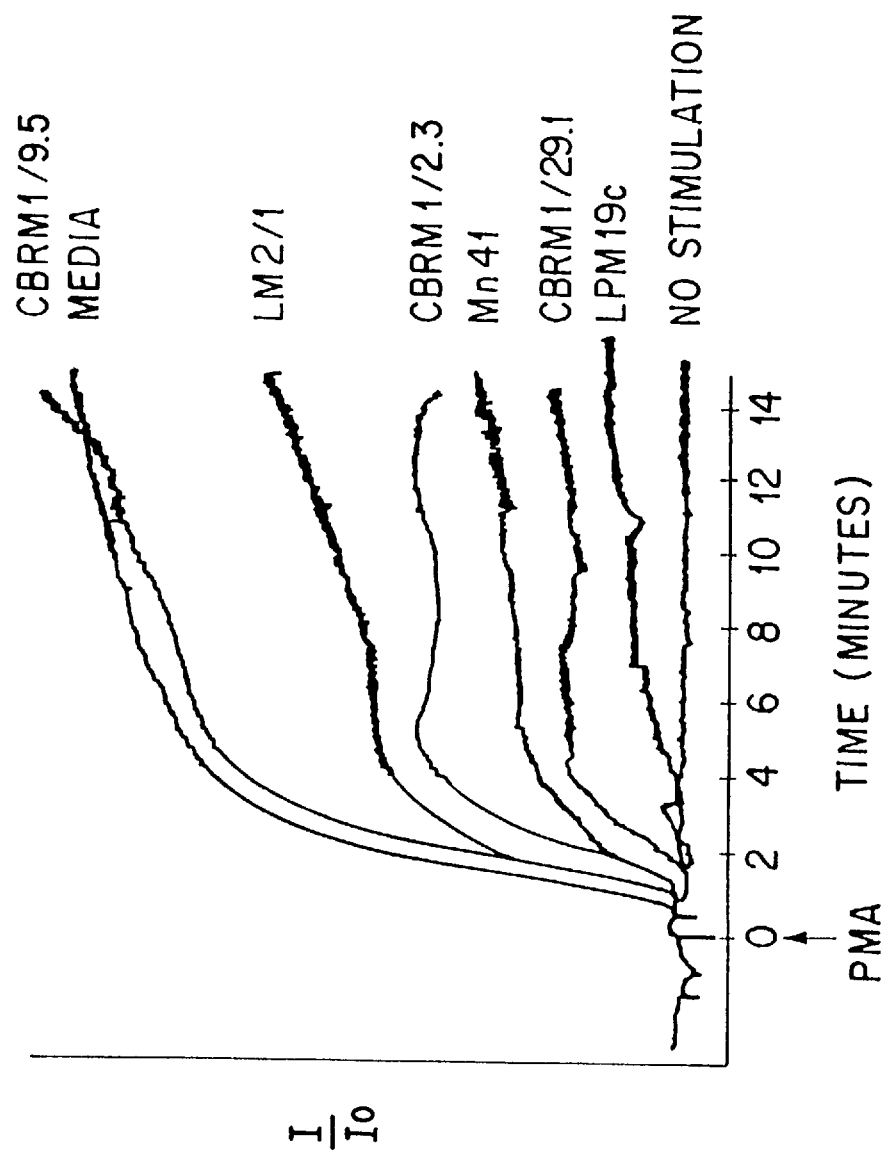

FIG. 17. Aggregometry profiles of neutrophils activated with PMA. Neutrophils were preincubated with the indicated MAbs for 25 minutes at room temperature, equilibrated at 37° C., and activated with PMA (100 ng/ml, t=0 min). Individual representative tracings are shown for experiments that were performed at least three times. I/I$_0$ represents the relative light transmission.

Figure 18A:
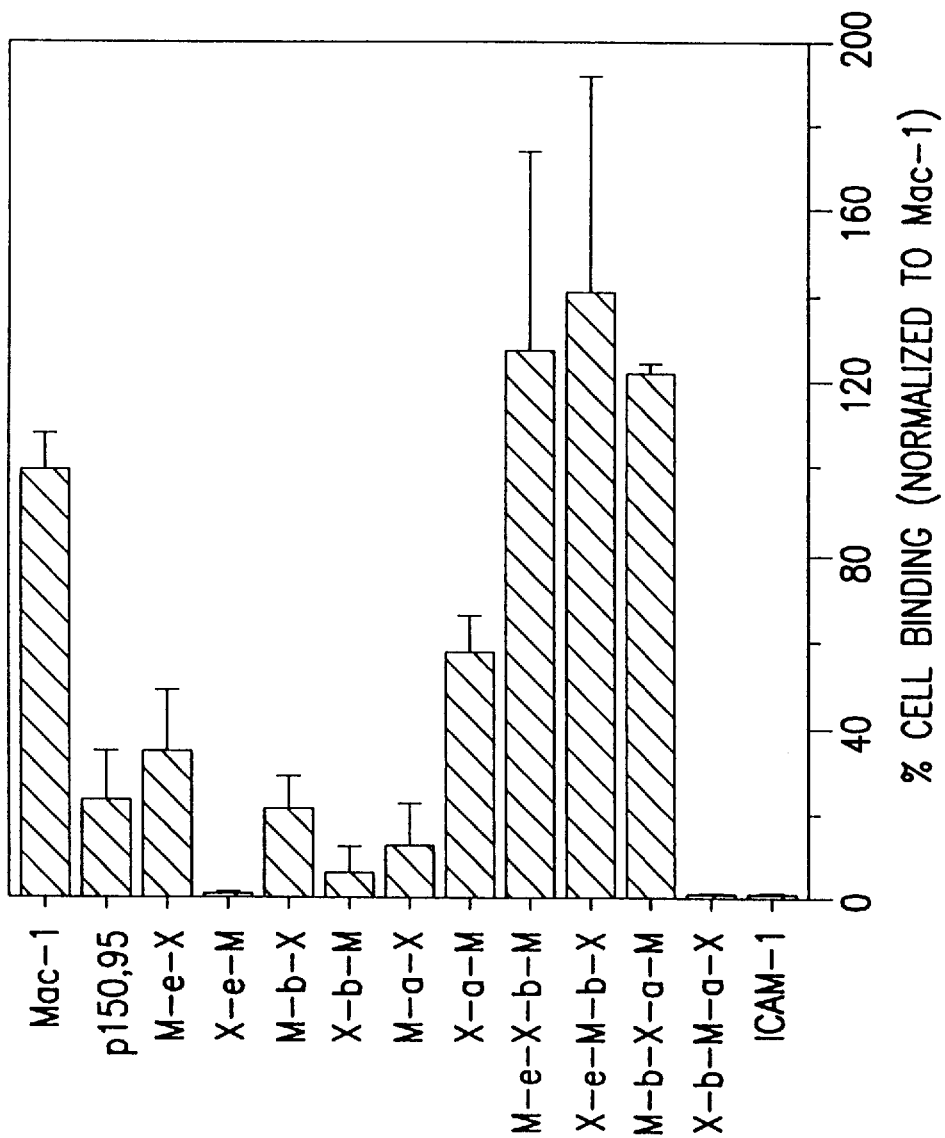

FIGS. 18A–18B. CHO cell transfectant binding to ICAM-1 (A) and iC3b-E (B). FIG. 18A. Mac-1, p150,95, Mac-1/p150,95 chimeras, and ICAM-1 transfected CHO cells were detached, resuspended ($8\times10^5$ cells) in 1 ml, stimulated with PMA (100 ng/ml), and bound to immunoaffinity purified ICAM-1 adsorbed to plastic for 90 minutes at room temperature. Unbound cells were removed by five washes with a transfer pipette. Bound cells were quantitated by visually scoring the number of cells in five microscopic fields (40×magnification). Background binding to plates lacking ICAM-1 was determined for each transfectant and subtracted. The data is the average of three experiments and is normalized to the binding of wild type Mac-1. Bars indicate the standard error of the means. FIG. 14B. Transfected CHO cells were detached, replated on tissue culture treated 6 well plates ($4\times10^5$ cells/ml, 0.5 ml/well), and adhered for greater than 3 hours at 37° C. at 10% $CO_2$. Erythrocytes (iC3b-E, 50 μl of $2\times10^8$ cells/ml) were added and incubated with transfectants for 60 minutes at 37° C. Non-adherent erythrocytes were removed after eight washes with a transfer pipette and rosettes (>10 erythrocytes/CHO cell, >100 cells examined) were scored by light microscopy at 100×magnification. The data is the average of three experiments. Bars indicate the standard error of the means.

DESCRIPTION OF THE PREFERRED EMBODIMENTS

The present invention is based on the novel observation that when resting myeloid cells are stimulated, not all of the Mac-1 molecules present on the cell surface become activated and capable of binding ligand. Only select subpopulations of Mac-1 molecules as well as subpopulation of myeloid cells become activated and capable of binding to ligands of Mac-1. Upon activation, activation specific epitopes appear on the Mac-1 molecule which differentiate the activated Mac-1 molecules and stimulated myeloid cells from the non-activated Mac-1 molecules and resting myeloid cells.

Based on this disclosure, the present invention discloses the generation of a novel class of monoclonal antibodies, MAbs, which bind to activated Mac-1 molecules present on stimulated myeloid cells but are substantially incapable of binding to non-activated Mac-1 molecules on stimulated and resting myeloid cells. These antibodies were also found to possess the novel ability to bind to purified Mac-1 substrates, as well as detergent solubilized cell lysates.

Anti-Mac-1 MAbs are generated using routine procedures known in the art (Harlow et al., *Antibodies: A Laboratory Manual*, Cold Spring Harbor Press (1988)) using either purified Mac-1 or cells expressing activated Mac-1 as an immunogen. Once anti-Mac-1 antibodies have been generated, antibodies which selectively bind to activated Mac-1 can be identified in several fashions.

First, antibodies which selectively bind stimulated myeloid cells can be identified by screening the antibody for the ability to bind to stimulated myeloid cells such as neutrophils, and the inability to bind to resting myeloid cells.

Alternatively, antibodies which bind stimulated myeloid cells can be identified by screening the antibody for the ability to bind to purified activated Mac-1, and the inability to bind to purified deactivated Mac-1.

As used herein, a monoclonal antibody is said to "selectively bind" to activated Mac-1 or stimulated myeloid cells when the antibody binds to stimulated myeloid cells or activated Mac-1 but is substantially incapable of binding to non-activated Mac-1 or resting myeloid cells. An antibody is said to be "substantially incapable" of binding to resting myeloid cells if the level of binding to the resting myeloid cells is less than 10% of the level of binding to stimulated cells.

As used herein, a myeloid cell is said to be stimulated when the cell is capable of binding to a ligand of Mac-1 or is capable of participating in a Mac-1 dependent biological function. Therefore, a stimulated myeloid cell is a cell which is capable of binding to ICAM-1, iC3b, fibrinogen, and/or is capable of participating in Mac-1 dependent fractions such as homotypic aggregation. Treatments which stimulate myeloid cells include, but are not limited to agents such as fMLP and PMA.

As used herein, a myeloid cell is said to be resting when the cell is incapable of binding to a ligand of Mac-1 or is incapable of participating in a Mac-1 dependent biological function. Therefore, a resting myeloid cell is a cell which is incapable of binding to ICAM-1, iC3b, fibrinogen, and/or is incapable of Mac-1 dependent homotypic aggregation.

In detail, differential screening is performed using two populations of myeloid cells, or purified Mac-1 molecules. Myeloid cells, such as neutrophils, and Mac-1 molecules (activated and de-activated forms) are isolated using known methods. When using purified cells, the purified cells are separated into two populations. The two populations are preincubated under conditions which keeps Mac-1 on these cells in a resting conformation, for example at about 37° C. for about five minutes in HHMC. One of the population of cells is incubated under conditions which activate Mac-1, for example, in a media containing 100 ng/ml PMA, while the other population is maintained in the resting medium.

The antibodies which are to be screened are then incubated with a sample of the two populations of cells, or a sample of purified activated and de-activated Mac-1, and antibodies are selected which selectively bind to the activated population of myeloid cells, or purified activated Mac-1 molecules. Any method for screening antibody binding to a cell or molecule can be used. These include, but are not limited to, flow cytometry, ELISA, and RIA. When large numbers of antibodies are screened, it may be preferable to fixed the myeloid cells prior to incubation with the antibody, for example by incubating the cell in 2% paraformaldehyde.

Alternatively, the above procedures can be performed with two populations of cells expressing recombinant Mac-1. Any cell capable of expressing Mac-1 can be used. These include, but are not limited to yeast, bacteria such as *E. coli*, mammalian cells and insect cells.

Using such a procedure, two antibodies designated as CBRM1/5, and CBRM1/19 were generated and identified.

Using CBRM1/5 or CBRM1/19 as a marker of a distinct subpopulation of stimulated myeloid cells and activated Mac-1 molecules, other members of this class of antibodies can be identified.

Antibodies which bind to the same activation specific epitope, or to a sterically overlapping activation specific epitope on the activated Mac-1 molecule as that bound by CBRM1/5 or that bound by CBRM1/19 can be identified using a two antibody binding assay or a competitive binding assay. Such antibodies may recognize the same subpopulation of Mac-1 molecules as that bound by CBRM1/5 or CBRM1/19 or may bind to a different subpopulation of activated Mac-1 molecules.

As used herein, "activation specific epitope" refers to an epitope which is present on activated Mac-1 molecules but is not present on non-activated Mac-1 molecules. Such epitopes are often referred to as a neoepitope.

As used herein, two epitopes are said to be the "same" or "sterically overlapping" if antibodies to the two epitopes compete with and exclude each other's ability to bind to the antigen.

Antibodies which bind to different or non-sterically overlapping activation specific epitopes can be identified by their ability to non-competitively bind to the same sub-population of stimulated myeloid cells or the ability to non-competitively bind to the same sub-population of activated Mac-1 as that bound by CBRM1/5 or that bound by CBRM1/19.

Any of the known method for testing whether two antibodies bind to the same population of cells or the same molecule can be modified by one skilled in the art to identify antibodies which bind to the same population of cells or molecules in either a competitive or non-competitive fashion, as that bound by CBRM1/5 or that bound by CBRM1/19. Such assays include, but are not limited to, flow cytometry and ELISA analysis.

The present invention further provides the antibodies CBRM1/5 and CBRM1/19 in substantially purified form. As used herein, an antibody is said to be "substantially purified" if it purified to the level necessary in order to be effectively administered to a subject or to be of use for a desired purpose. In some cases the antibody will be substantially free from all cellular components while in other instances the antibody will only be free from other immunoglobulin like proteins.

The present invention further provides a hybridoma capable of producing the CBRM 1/5 antibody. The hybridoma producing this antibody has been deposited and designated HB11460 on Oct. 14, 1993, at the American Type Culture Collection (ATCC), 12301 Parklawn Drive, Rockville, Md. 20852, USA.

The present invention further provides a hybridoma capable of producing the CBRM1/19 antibody. The hybridoma producing this antibody has been deposited and designated HB11461 on Oct. 14, 1993, at the American Type Culture Collection (ATCC), 12301 Parklawn Drive, Rockville, Md. 20852, USA.

The present invention further includes fragments of the antibodies of the present invention which maintain their ability to bind to stimulated myeloid cells or to activated Mac-1. Such fragment include, but are not limited to, the Fv, the Fab, and the $Fab_2$ fragments. One skilled in the art can readily generated antibody fragments which maintain binding ability using routine methodology.

The present invention further includes derivatives of the antibodies of the present invention (antibody derivative). As used herein, an "antibody derivative" contains an antibody of the present invention, or a fragment of said antibody, as well as an additional moiety which is not normally a part of the antibody. Such moieties may improve the antibodies' solubility, absorption, biological half life, etc, or may alternatively decrease the toxicity of the antibody, eliminate or attenuate any undesirable side effect of the antibody, etc. Moieties capable of mediating such effects are disclosed in *Remington's Pharmaceutical Sciences* (1980).

"Toxin-derivatized" antibodies constitute a special class of antibody derivatives. A "toxin-derivatized" antibody is an antibody, or antibody fragment which contains an additional toxin moiety. The binding of such an agent to a cell brings the toxin moiety into close proximity to the cell and thereby promotes cell death. Any suitable toxin moiety may be employed; however, it is preferable to employ toxins such as, for example, the ricin toxin, the diphtheria toxin, radio-isotopic toxins, membrane-channel-forming toxins, etc. Procedures for generating such toxin derivatives are well known in the art.

"Detectably labeled" antibodies constitute another special class of the antibody derivatives of the present invention. An antibody is said to be detectably labeled if the antibody, or fragment thereof, is attached to a molecule which is capable of identification, visualization, or localization using known methods. The detectable labels of the present invention include, but are not limited to, radioisotopes labels, affinity labels (such as biotin, avidin, etc.) fluorescent labels, paramagnetic atoms, etc. Procedures for accomplishing such labeling are well known to the art.

The present invention further includes humanized forms of the antibodies of the present invention. Humanized forms of the antibodies of the present invention may be produced, for example by replacing an immunogenic portion of an antibody with a corresponding, but non-immunogenic portion (i.e. chimeric antibodies) (Cabilly, et al., European Patent Application 125,023; Better, et al., *Science* 240:1041–1043 (1988); Liu, et al., *Proc. Natl. Acad. Sci. USA* 84:3439–3443 (1987); Liu, et al., *J. Immunol.* 139:3521–3526 (1987); Wood, et al., *Nature* 314:446–449 (1985)); all of which references are incorporated herein by reference).

Alternatively, suitable "humanized" antibodies can be produced by CDR or CEA grafting/substitution (Jones, et al., *Nature* 321:552–525 (1986); Verhoeyan et al., *Science* 239:1534 (1988); Beidler, et al., *J. Immunol.* 141:4053–4060 (1988); all of which references are incorporated herein by reference).

The present invention further provides methods of selectively inhibiting the binding of stimulated myeloid cells to a ligand of Mac-1.

As used herein, a ligand of Mac-1 is defined as a non-antibody molecule which is capable of binding to Mac-1. Ligands of Mac-1 include, but are not limited to, iC3/b, ICAM-1, and fibrinogen.

In detail, stimulated myeloid cells can be blocked from binding to a Mac-1 ligand by supplying to the myeloid cells an antibody, antibody fragment, or antibody derivative which is capable of binding to activated Mac-1 present on stimulated myeloid cells and is substantially incapable of binding to non-activated Mac-1. For example, CBRM1/5, when supplied to a stimulated myeloid cell, will bind to the activated Mac-1 molecules present on the cell and block the binding of the cell to ICAM-1 and fibrinogen. However, activation specific anti-Mac-1 antibodies which inhibit other Mac-1/ligand interactions, such as Mac-1/iC3b binding, can be isolated.

The adhesion, migration, and biological activity of circulating myeloid cells such as neutrophils and monocytes results from interactions involving Mac-1 and it's ligands. Cellular adhesion has been found to be required for neutrophil and monocyte migration to sites of inflammation and for various neutrophil and monocyte effector functions contributing to inflammation.

Non-activation specific anti-Mac-1 antibodies which inhibit such cellular adhesion, have been demonstrated to be effective at preventing an inflammatory response when administered to a human subject. In addition, anti-Mac-1 antibodies have been demonstrated to inhibit phagocytosis of foreign material by monocytes. Further, antibodies which bind to Mac-1 have been demonstrated to be effective at mediating other monocyte and neutrophil activities such as chemokinesis, and chemotaxis both in vitro as well as in vivo.

Because of their specificity and selectivity, the antibodies, the antibody fragments, and the antibody derivatives of the present invention agents provide an improvement over previously disclosed anti-Mac-1 antibodies for use as an anti-inflammatory agent, an anti-malarial agent, an anti-HIV agent, and an anti-asthma agent, for example, see Fisher et al., *Lancet* 2:1058 (1986), Perez et al., *Bone Marrow Transp.* 4:379 (1989), Patarroyo et al., *Scan J. Immunol.* 30:129–164 (1989), Lindbom et al., *Clin. Immun. Inmuno Patholo.* 57: 105–119 (1990), Butcher, *Amer. J. Pathol.* 136:3–11 (1990), Falanga et al. *Eur. J. Immunol.* 21:2259–2263 (1991), Dreyer et al. *Circulation* 84:400–411 (1991), Simpson et al., *Circulation* 81:226–237 (1990) and Wegner et al., *Chest* 101:345–395 (1992), all of which are herein incorporated by reference. As previously demonstrated, anti-Mac-1 antibodies are effective in treating inflammation caused by a reaction of the non-specific defense system.

The term "inflammation," as used herein, is meant to include only reactions of the non-specific defense system. A "reaction of the non-specific defense system" is a response mediated by myeloid cells incapable of immunological memory. Such cells include neutrophils and macrophages. As used herein, inflammation is said to result from a response of the non-specific defense system, if the inflammation is caused by, mediated by, or associated with a reaction of the non-specific defense system. Examples of inflammation which result, at least in part, from a reaction of the non-specific defense system include inflammation associated with conditions such as: adult respiratory distress syndrome (ARDS) or multiple organ injury syndromes secondary to septicemia or trauma; reperfusion injury of myocardial or other tissues; acute glomerulonephritis; reactive arthritis; dermatoses with acute inflammatory components; acute purulent meningitis or other central nervous system inflammatory disorders; thermal injury; hemodialysis; leukapheresis; ulcerative colitis; Crohn's disease; necrotizing enterocolitis; granulocyte transfusion associated syndromes; and cytokine-induced toxicity.

The activation specific anti-Mac-1 antibodies of the present invention, fragments of said antibodies, and derivatives thereof, are administered to a patient as an anti-inflammatory agent to treat the above recited condition as well as others conditions which are mediated by the non-specific defense system. Such agents differ from general anti-inflammatory agents in that they are capable of selectively targeting stimulated myeloid cell populations and inhibit Mac-1/specific ligand interaction. Such specificity will only affect specific biological function of the myeloid cell and will not cause side effects such as nephrotoxicity and myeloid cell depletion which are found with conventional and less specific anti-inflammatory agents. Further, such agents differ from other previously known anti-Mac-1 antibody agents in that they do not affect non-activated myeloid cell populations. Therefore, the antibodies, antibody fragments, and antibody derivatives of the present invention provide an improvement over all the previously recognized usage of anti-Mac-1 antibodies such as the treatment of inflammation resulting from a reaction of the non-specific defense system.

The ability of activation specific anti-Mac-1 antibodies to inhibit the interactions necessary for an inflammatory reaction provides the basis for their therapeutic use in the treatment of chronic inflammatory diseases and autoimmune diseases such as lupus erythematosus, autoimmune thyroiditis, experimental allergic encephalomyelitis (EAE), multiple sclerosis, some forms of diabetes Reynaud's syndrome, rheumatoid arthritis, etc. Such antibodies may also be employed as a therapy in the treatment of psoriasis. In general, the monoclonal antibodies capable of binding to activated Mac-1 may be employed in the treatment of those diseases currently treatable through steroid therapy and in which previous know non-activation specific anti-Mac-1 antibodies have been suggested.

Of special interest to the present invention are antibodies to activated Mac-1 which recognize the same subpopulation of stimulated myeloid cells or activated Mac-1 as that bound by the antibody CBRM1/5. Such antibodies can be used to block myeloid/ICAM-1 and myeloid/fibrinogen binding and hence can be used in vivo as a means of treating an inflammatory response of the non-specific defense system without affecting the reactions of the specific defense system and without the potential side effects of depleting non-activated neutrophils.

The present invention further provides methods of determining the location and distribution of expressing activated Mac-1 cells within a subject. The administration of detectably labeled activation specific anti-Mac-1 antibodies to a patient provides a means for imaging or visualizing the location, migration, and aggregation of cells expressing activated Mac-1 such as stimulated myeloid cells and myeloid tumor cells. Clinical application of antibodies in diagnostic imaging are reviewed by Grossman, *Urol. Clin. North Amer.* 13:465–474 (1986)), Unger, et al., *Invest. Radiol.* 20:693–700 (1985)), and Khaw, et al., *Science* 209:295–297 (1980)).

In such a use, the antibodies of the present invention, or fragments thereof, are administered to a patient in detectably labeled form. As described earlier with regards to antibody derivatives, antibodies can be detectably labeled through the use of radioisotopes, affinity labels (such as biotin, avidin, etc.) fluorescent labels, paramagnetic atoms, etc using procedures known to the art for use in the present invention.

The present invention further provides methods of selectively killing expressing activated Mac-1 cells. In detail, cells expressing activated Mac-1 can be selectively killed by contacting them with a "toxin derivatized antibody" which is capable of binding to activated Mac-1 but is substantially incapable of binding to non-activated Mac-1. As described above, the antibody derivatives of the present invention include antibodies which are conjugated to toxic molecules such as the ricin A chain. The present procedure provides a means of both treating Mac-1 dependent biological process by selectively killing the myeloid cells which mediate the process as well as a means of selectively killing tumor cells expressing activated Mac-1.

In providing a patient with antibodies, antibody fragments, or antibody derivatives capable of binding to activated Mac-1, the dosage of the agent which is to be administered will vary depending upon such factors as whether the antibody agent is being administered as a diagnostic agent or a therapeutic agent. Factors such as the patient's age, weight, height, sex, general medical condition, previous medical history, etc will also affect the dosage administered.

Techniques of dosage determination are well known in the art for diagnostic antibody agents as well as therapeutic antibody agents. In general, it is desirable to provide the recipient with a dosage of antibody which is in the range of from about 1 pg/kg to 10 mg/kg (body weight of patient). As discussed below however, the therapeutically effective dose can be lowered if the anti-Mac-1 antibody agent is additionally administered with an anti-ICAM-1 antibody, or its equivalent.

As used herein, one compound is said to be additionally administered with a second compound when the administration of the two compounds is in such proximity of time that both compounds can be detected at the same time in the patient's serum.

The activation specific anti-Mac-1 antibodies of the present invention, or fragment thereof, whether for use as a diagnostic or therapeutic agent, may be administered to patients intravenously, intranasally, intramuscularly, subcutaneously, enterally, or parenterally. When administering such molecules by injection, the administration may be by continuous infusion, or by single or multiple boluses.

The anti-inflammatory agents of the present invention are intended to be provided to recipient subjects in an amount sufficient to suppress the binding of activated Mac-1 to the Mac-1 ligand which mediates the biological function which is to be inhibited. For example, antibodies used to treat inflammation are administered to a patient in sufficient concentration so as to inhibit ICAM-1/Mac-1 binding.

An amount is said to be sufficient to "suppress" Mac-1/ligand interaction if the dosage, route of administration, etc. of the agent are sufficient to attenuate or prevent Mac-1/ligand interaction. Such attenuation or prevention can be assayed by examining whether the biological function mediated by the targeted interaction is occurring in vivo, for example by examining neutrophil infiltration into a site of inflammation, or by correlating in vitro blocking studies with predicted in vivo efficacy.

The activation specific anti-Mac-1 antibodies of the present invention may be administered either alone or in combination with one or more additional immunosuppressive agents (especially to a recipient of an organ or tissue transplant). The administration of such compound(s) may be for either a "prophylactic" or "therapeutic" purpose. When provided prophylactically, the compound(s) are provided in advance of any inflammatory response or symptom. The prophylactic administration of the compound(s) serves to prevent or attenuate any subsequent inflammatory response.

When provided therapeutically, the compound(s) is provided at (or shortly after) the onset of a symptom of actual inflammation. The therapeutic administration of the compound(s) serves to attenuate any actual inflammation. The anti-inflammatory agents of the present invention may, thus, be provided either prior to the onset of inflammation (so as to suppress an anticipated inflammation) or after the initiation of inflammation.

A composition is said to be "pharmacologically acceptable" if its administration can be tolerated by a recipient patient. Such an composition is said to be administered in a "therapeutically effective amount" if the amount administered is physiologically significant. An agent is physiologically significant if its presence results in a detectable change in the physiology of a recipient patient.

The antibody based agents of the present invention can be formulated according to known methods to prepare pharmaceutically useful compositions, whereby these materials, or their functional derivatives, are combined in admixture with a pharmaceutically acceptable carrier vehicle. Suitable vehicles and their formulation, inclusive of other human proteins, e.g., human serum albumin, are described, for example, in *Remington's Pharmaceutical Sciences* (16th ed., Osol, A., Ed., Mack, Easton Pa. (1980)). In order to form a pharmaceutically acceptable composition suitable for effective administration, such compositions will contain an effective amount of anti-Mac-1 antibody.

Additional pharmaceutical methods may be employed to control the duration of action. Control release preparations may be achieved through the use of polymers to complex or absorb the therapeutic agents of the invention. The controlled delivery may be exercised by selecting appropriate macromolecules (for example polyesters, polyamino acids, polyvinyl, pyrrolidone, ethylenevinylacetate, methylcellulose, carboxymethylcellulose, or protamine, sulfate) and the concentration of macromolecules as well as the methods of incorporation in order to control release. Another possible method to control the duration of action by controlled release preparations is to incorporate anti-Mac-1 antibodies into particles of a polymeric material such as polyesters, polyamino acids, hydrogels, poly(lactic acid) or ethylene vinyl acetate copolymers. Alternatively, instead of incorporating these agents into polymeric particles, it is possible to entrap these materials in microcapsules prepared, for example, by coacervation techniques or by interfacial polymerization, forexample, hydroxymethylcelluloseorgelatine-microcapsules and poly (methylmethacylate) microcapsules, respectively, or in colloidal drug delivery systems, for example, liposomes, albumin microspheres, microemulsions, nanoparticles, and nanocapsules or in macroemulsions. Such techniques are disclosed in *Remington's Pharmaceutical Sciences* (1980).

The present invention further provides methods of identifying agents capable of activating Mac-1 present on resting myeloid cells. Agents can be assayed for their ability to stimulate resting myeloid cells or activate Mac-1 by examining treated cells, or purified Mac-1 molecules which have been treated with the agent for the appearance of activation specific epitopes.

In detail, isolated myeloid cells such as neutrophils or isolated de-activated Mac-1 molecules are first contacted with the agent which is to be tested. The treated cells or Mac-1 molecules are then contacted with an antibody which is capable of binding to activated Mac-1 but is substantially incapable of binding to non-activated Mac-1 and resting myeloid cells. The cells or Mac-1 molecules are then examined to determine whether the cells or molecules binds to the activation specific antibody. If the cells or Mac-1 molecules are able to bind such an antibody, the agent which was placed in contact with the cells Mac-1 or molecules are said to be a "stimulating agent."

The present invention further provides methods of capable of deactivating Mac-1. In detail, stimulated myeloid cells such as PMA treated neutrophils, or isolated activated Mac-1 molecules, are first contacted with the agent which is to be tested. The treated cells or Mac-1 molecules are then contacted with an antibody which is capable of binding to activated Mac-1 but is substantially incapable of binding to non-activated Mac-1 or to resting myeloid cells. The cells or Mac-1 molecules are then examined to determine whether the cells or Mac-1 molecules binds to the antibody. If the cells or molecules are no longer able to bind to the antibody, the agent which was first placed in contact with the cells or Mac-1 molecules are said to be a "deactivating agent."

The present invention further provides methods of identifying agents capable of blocking the activation of Mac-1 present on resting myeloid cells. In detail, resting myeloid cells, such as neutrophils, or isolated de-activated Mac-1 molecules, are first contacted with the agent which is to be tested. The contacted cells or Mac-1 molecules are then treated with an agent capable of stimulating myeloid cells, or activating Mac-1 molecules, for example PMA. These cells or Mac-1 molecules are then incubated with an antibody which is capable of binding to activated Mac-1 but is substantially incapble of binding to non-activated Mac-1 or to resting myeloid cells. The cells or Mac-1 molecules are then examined to determine whether the cells or Mac-1 molecules binds to the antibody. If the cells or Mac-1 molecules are not capable of binding to the antibody, the agent which was first placed in contact with the cells or Mac-1 molecules is said to be an "activation blocking agent".

The present invention further provides methods of selectively removing cells from fluids or tissues which contain activated Mac-1 on their cell surface. In detail, stimulated myeloid cells which contain activated Mac-1 can be selectively removed from a fluid or tissue, such as a patient's blood, by passing the fluid over an immobilized antibody which is capable of binding to activated Mac-1 present on stimulated myeloid cells but is substantially incapable of binding to non-activated Mac-1 or resting myeloid cells. For example, stimulated myeloid cells or tumor cells expressing activated Mac-1 can be removed from a patient's blood by subjecting the patient to leukophoresis in which the leukophoresis contacts the patient's blood with an immobilized, activation specific anti-Mac-1 antibody.

The present invention is further based on the novel observation that a majority of the antibodies which block Mac-1/ligand interactions bind to regions within the I domain of the Mac-1 molecule (see example 2). Further, it was found that antibodies could be generated which block specific subsets of Mac-1/ligand interaction, for example CBRM1/1 completely blocked Mac-1/ICAM-1 interaction but had no effect on Mac-1/neutrophil binding. Based on this observation, the present invention provides methods of identifying agents which are capable of blocking specific Mac-1/ligand interaction.

In detail, the antibodies described in FIGS. 13 and 14, or an equivalent set of antibodies, can be used to map the peptide residues within the Mac-1 molecule which bind to specific Mac-1 ligands. A similar approach to epitope mapping is described in U.S. Pat. No. 5,288,854.

The present invention discloses that the sites of interaction between Mac-1 and the various Mac-1 ligands (iC3b, ICAM-1, and fibrinogen) are located within the I domain of Mac-1 and are distinct and mostly do not overlap. Based on this disclosure short peptide fragments of the Mac-1 sequence can be generated which are substantially capable of blocking specific subsets of Mac-1/ligand interaction.

As used herein "specific subsets of Mac-1/ligand interaction" refers to an agent's ability to block one or more Mac-1/ligand interactions. For example, a peptide may block a specific subset of Mac-1/ligand interactions by blocking Mac-1 binding to a single ligand such as ICAM-1.

Among the preferred short peptide fragment of the present invention are peptides which bind to the Mac-1 contact site on the Mac-1 ligand, which comprises amino acid sequences derived from the amino acid sequence of Mac-1, as well as peptide which bind to the ligand binding site present on Mac-1 which comprise amino acid sequences derived from the Mac-1 ligand.

The monoclonal antibody blocking data presented herein can be combined with routine mutagenesis studies in order to further map MAb epitopes to distinct regions within the I domain of Mac-1. In addition, amino acid substitution and domain deletion mutagenesis of Mac-1 can performed, for example by oligonucleotide directed mutagenesis as described by Kunkel, (*Proc. Natl Acad. Sci. USA*, 82:488–492, (1985)), as modified by Peterson et al. (*Nature*, 329:842–846 (1987)), in order to generate Mac-1 deletion and substitution mutants which lack the ability to bind to a specific Mac-1 ligand or antibody. By using such procedures, short peptide sequences which serve as the ligand contact site on Mac-1 can be determined.

The present invention further provides chimeric molecules comprising a fusion between Mac-1 and p150,95, see Example 2. Such chimeric molecules are useful in mapping epitopic domains and ligand contact regions within the Mac-1 and p150,95 molecules. Further, chimeric molecules can be generated which maintain the ability to associate with the β-subunit (CD11) of the protein dimer and participate in a select set of α-subunit ligand binding. For example, a chimeric Mac-1/p150,95 α subunit can be generated which maintains the ability to form a dimer with CD18 as well as bind ICAM-1 and fibrinogen, but is incapable of neutrophil aggregation or Mac-1 dependent homotypic aggregation. Methods of generating such chimeras, as well as suggestions of their use are described U.S. Pat. No. 5,288,854.

Having now generally described the invention, the same will be more readily understood through reference to the following examples which are provided by way of illustration, and are not intended to be limiting of the present invention, unless specified.

EXAMPLE 1

IDENTIFICATION OF A NOVEL CLASS OF ANTI-MAC-1 ANTIBODIES

Materials and Methods

MAbs

The following murine MAbs against human antigens were used: TS1/22 (anti-CD11a, IgG1, ascites)(Sanchez-Madrid et al., *Proc. Natl. Acad. Sci. USAS* 79:7489–7493 (1982)); LM2/1 (anti-CD11b, IgG1, protein A-purified) (Miller et al., *J. Immunol.* 137:28910–2900 (1986)); CBRM1/23 (anti-CD11b, IgG2a, protein-A purified); OKM1 (anti-CD11b, IgG2b, protein-A purified (Wright et al., *Proc. Natl. Acad. Sci. USA* 80:5699–5703 (1983), LPM19c (anti-CD11b, IgG2a, a gift of Dr. K. Pulford, Oxford, UK (Uciechowski et al., *In Leukocyte Typing IV: White Cell Differentiation Antigens*, Knapp editor, Oxford University Press, Oxford, pages 543–551 (1989)); BLY6 (anti-CD11c, IgG1, ascites (Uciechowski et al., *In Leukocyte Typing IV: White Cell Differentiation Antigens*, Knapp editor, Oxford University Press, Oxford, pages 543–551 (1989)); R6.5 (anti-CD54, IgG2a, generous gift of Dr. R. Rothlein, Boehringer-Ingelheim, Ridgefield, Conn.) (Smith et al., *J. Clin. Invest.* 82:1746–1756 (1988); CBRIC1/11 anti-CD54, IgG1, protein-A purified); and My4 (anti-CD14, IgG2b, purified) (Griffin et al., *J. Clin. Invest.* 69:932–941 (1981)) (Coulter Immunology, Hialeah, Fla.). X63 (nonbinding antibody, IgG1) and 3G8 (anti-CD16, IgG1) (Fleit et al., *In Leucocyte Typing IV: White Cell Differentiation Antigens*, Knapp et al. editors, Oxford University Press, Oxford, pages 579–581 (1989)) were used as culture supernatants.

Protein Purification

Mac-1 was purified from leukocyte lysates by immunoaffinity chromatography after detergent solubilization as described (Diamond et al., *Cell* 65:961–971 (1991)). Soluble ICAM-1 (sICAM-1, generous gift of Dr. S. Marlin, Boehringer-Ingelheim Pharmaceuticals, Ridgefield, Conn.) was purified from supernatants of ICAM-1 transfected CHO cells by immunoaffinity chromatography as described (Marlin et al., *Nature* 344:70–72 (1990)).

Tissue Culture, Transfection, and Cell Preparation

Neutrophils were isolated from the whole blood of healthy volunteers by dextran sedimentation at room temperature, with Ficoll gradient centrifugation and hypotonic lysis at 4° C. as described (English et al., *J. Immunol. Methods* 5:249 (1974), Miller et al, *J. Clin. Invest.* 80:535–544 (1987)). Prior to $^{125}$I-MAb binding experiments, neutrophils ($2\times10^7$ cells/ml) were stored at 4° C. at in HBSS, 10 mM HEPES pH 7.3, 1 mM $MgCl_2$, 1 mM $CaCl_2$ (HHMC) in polypropylene tubes (Falcoln 2097, Becton Dickinson, Lincoln Park, N.J.). For time course and temperature studies the leukocyte rich supernatant was used after dextran sedimentation. Cell suspensions were placed on ice immediately and washed four times to remove platelets in HBSS, 10 mM HEPES pH 7.3, and resuspended at $5\times10^6$ cells/ml in HHMC. Neutrophils were identified during flow cytometry by forward and 90° scatter, and confirmed by immunostaining with a MAb to CD16. Mononuclear cells were isolated from the interface of the Ficoll gradient and washed five times in RPM1 1640, 5 mM EDTA, 2.5% FCS (heat-inactivated, low endotoxin, Hyclone, Utah), and resuspended in L15, 2.5% FCS, 1 mg/ml human γ-globulin (ICN ImmunoBiologicals, Costa Mesa, Calif.) at $5\times10^6$ cells/ml at 4° C. Mononuclear cells were immunostained according to the protocol for neutrophils (see below). The monocyte subpopulation was determined by the flow cytometric forward and 90° scatter pattern and confirmed by immunostaining with the a MAb to the monocyte-specific CD14 antigen.

The generation and selection of CHO cells expressing wild type and chimeric forms of Mac-1 and p150,95 will be described. They were maintained in ce-MEM, 10% dialyzed FCS, 16 μM thymidine, 0.05 μM methotrexate, 2 mM glutamine, and 50 μg/ml gentamicin.

Generation and Labelling of CBRM1/5 IRG and Fab Fragments

The generation of MAbs against Mac-1 are described in Example 2. In brief, hybridomas were prepared from BALB/c mice that were immunized with immunoaffinity purified Mac-1. Hybridomas (500) were screened as follows. Purified neutrophils were isolated, separated into two groups, and preincubated at 37° C. for five minutes in HHMC. One population was treated with phorbol esters (PMA, 100 ng/ml) for ten minutes while the other remained untreated. Cell suspensions were placed on ice for five minutes, incubated with hybridoma supernatants, and processed by flow cytometry. In some cases, neutrophils were fixed with 2% paraformaldehyde prior to incubation with MAbs. CBRM1/5 was identified for its ability to bind PMA stimulated but not resting neutrophils. It was cloned twice by limiting dilution, and purified from culture supernatant by protein-A Sepharose affinity chromatography after $NH_4SO_4$ precipitation (Harlow et al., *Antibodies: A Laboratory Manual* (Cold Spring Harbor: Cold Spring Harbor Laboratory (1988)). CBRM1/5 was determined to be of the IgG1 subclass (ImmunoPure Monoclonal Antibody Isotyping Kit, Pierce, Rockford, Ill.)

Fab fragmentation of CBRM1/5 was performed by pepsin digestion followed by cysteine reduction (Parham, P., *In Immunological Methods in Biomedical Sciences*, Weir et al. editors, Blackwell, Oxford (1983)). Fab' were separated by 1.5 cm×75 cm S-200 SEPHACRYL (Pharmacia, Piscataway, N.J.) size exclusion chromatography. Fab' eluted from the column as a single homogeneous peak with an apparent $M_r$ of 40,000. Purity of $F(ab')_2$ and Fab' fragments was confirmed by reducing (5% β-mercaptoethanol) and non-reducing (50 mM iodoacetamide) SDS-8% PAGE. Proteins were visualized by silver staining (Morrissey, J.H. *Anal Biochem.* 117:307–310 (1981)). Unlabelled (Bio-Rad, Richmond, Calif.) or $^{14}$C-labelled (GIBCO BRL, Gaithersburg, Md.) protein standards included myosin ($M_r$ 200,000), β-galactosidase ($M_r$ 116,000), phosphorylase B ($M_r$ 97,000), serum albumin ($M_r$ 66,000), ovalbumin ($M_r$ 43,000), carbonic anhydrase ($M_r$ 31,000), trypsin inhibitor ($M_r$ 21,500), and lysozyme ($M_r$ 14,000).

MAbs (100 μg) were labelled with $Na^{125}I$ (1 mCi) using 1,3,4,6-tetrachloro-3α,6α-diphenylglycouril (Pierce Chemical Co, Rockford, Ill.) (Fraker et al., *Bioichem. Biophys. Res. Commun* 80:849–857 (1978)). The specific activity of the iodinated MAbs was determined (protein recovery averaged 83 μgs, specific activity was $6-7\times10^6$ CPM/μg).

$^{125}$I-MAb Binding Assays

Purified neutrophils ($2\times10^7$ cells/ml in HHMC) were either kept on ice or warmed to 37° C. for five minutes and stimulated (PMA, 100 ng/ml; fMLP, $10^{-7}$M) for ten minutes. Activated neutrophils were immediately placed on ice and 500,000 cells were aliquotted into U-bottom plates (96 well non-tissue culture treated microtiter plates, Linbro-Titertek, Flow Laboratories, McLean, Va.) containing increasing concentrations of iodinated MAb (0.109 nM–112 nM) in the absence or presence of 20–100 fold excess cold MAb. The binding media contained L15, 2.5% FCS, 1 mg/ml human γ-globulin. Neutrophils were incubated with iodinated MAbs for 4 h on ice, washed five times with L15, 2.5% FCS by 21 gauge needle aspiration, lysed with L15, 2.5% FCS, 0.2N NaOH, and counted for γ-emission. Specific binding was determined by subtracting the CPM in the presence of excess cold MAb. Scatchard plots were generated (Scatchard, G. *Ann N. Y. Acad. Sci.* 51:660–672 (1949)) and site densities were determined using the data point at which there was no additional increase in specific binding of labelled MAb.

Surface Labelling, Immunoprecipitation, and Gel Electrophoresis

Purified neutrophils ($2\times10^7$ cells) were washed twice in PBS, 1 mM $MgCl_2$, 0.5 mM $CaCl_2$ and resuspended in 2 mls; fMLP ($10^{-7}$M) was added to some aliquots of neutrophils. The cells were iodinated, lysed and precleared as described (Diamond et al., *Cell* 65:961–971 (1991)).

Immunoprecipitations were performed one of two ways: (i) indirectly by incubating 250 μl of MAb (neat supernatant or 20 μg/ml purified IgG) with 1 μl of 1 mg/ml purified rabbit anti-mouse IgG (Zymed, San Francisco Calif.) for 4 hours at 4° C. Protein-A-SEPHAROSE (20 μl of a 1:1 slurry) was added for overnight incubation. Eppendorf tubes were centrifuged, supernatants were aspirated, 50 μl of iodinated neutrophil lysate was added and the mixture was incubated for 2 hours at 4° C. while shaking vigorously; (ii) directly by adding 60 μl of a 1:4 diluted lysate to 60 μl of directly coupled MAb-SEPHAROSE (2–3 mg purified MAb per ml CNBr-activated SEPHAROSE CL-4B) and incubating for 2 h at 4° C. while shaking vigorously. The washing and elution of the immunoprecipitates has been described (Diamond et al., *Cell* 65:961–971 (1991)). Samples were loaded, and subjected to SDS-7% PAGE (Laemmli, U.K. *Nature* 227:680–685 (1970)) in the presence of β-mercaptoethanol, and autoradiographed with intensifying screens (Laskey et al., *FEBS Letters* 82:314–316 (1977)). Preclearing experiments were performed with directly coupled SEPHAROSE as follows: after the initial immunoprecipitation with control (mouse IgG) or specific SEPHAROSE (LM2/1, CBRM1/5), the beads were pelleted, the supernatant (60 μl) was transferred to a second aliquot of the same MAb-SEPHAROSE, and incubated as described above. Subsequently, these beads were pelleted, the supernatants (60 μl) transferred to an aliquot of either LM2/1 or CBRM1/5-SEPHAROSE, and incubated. After each round of immunoprecip-itation, the beads were washed and the bound protein eluted as described (Diamond et al., *Cell* 65:961–971 (1991)). Samples were loaded, and subjected to SDS-5% PAGE (Laemmli, U.K. *Nature* 227:680–685 (1970)) in the presence of β-mercaptoethanol, and autoradiography (Laskey et al., *FEBS Letters* 82:314–316 (1977)).

ELISA with Purified Mac-1

Immunoaffinity purified human Mac-1 was diluted 1/20 in 25 mM Tris-HCl, 150 mM NaCl, 2 mM $MgCl_2$ and adsorbed to individual wells of a non-tissue culture treated microtiter plate (Linbro-Titertek, Flow Laboratories, McLean, Va.) for 1 h at 37° C. Plates were washed five times and blocked for one hour at 37° C. in HHMC supplemented with 1% human serum albumin. Plates were then washed twice with HBSS, 10 mM HEPES pH 7.3, 10 mM EDTA, 0.05% Tween 20 and twice with HBSS, 10 mM HEPES pH 7.3, 0.05% Tween 20. MAb solution (100 μl of 20 μg/ml of purified MAbs) in HBSS, 10 mM HEPES pH 7.3, 0.05% Tween 20 supplemented with either 1 mM $MgCl_2$, 1 mM $CaCl_2$, 1 mM $MnCl_2$ or 5 mM EDTA (HHTcation) was added to the wells and allowed to incubate for 1 h at 37° C. The plates subsequently were iced for five minutes and washed four times with HHTcation at 4° C. Enzyme linked second antibody (50 μl of 1/400 dilution of horseradish peroxidase goat anti-mouse IgG, Zymed Laboratories, San Francisco, Calif.) was added in HHTcation, incubated for 1 h at 4° C. and the plates were washed five times with HHTcation at 4° C. Substrate (2,2-azino-di (3-ethylbenzthiazoline) sulfonic acid, Zymed Laboratories, San Francisco, Calif.) was added in 0.1M citrate with 0.05% $H_2O_2$, and the results quantitated at 414 nm on an ELISA plate reader (Titertek Multiscan MCC340).

Flow Cytometry Studies

The time course and temperature studies were performed as follows: Purified neutrophils or leukocyte rich supernatants after dextran sedimentation ($5.0 \times 10^6$ cells/ml in HHMC) were preincubated in eppendorf (1.5 ml) tubes at 0°, 25°, or 37° C. for five minutes before stimulus was added (IL-8, 25 ng/ml (72 amino acid form), PeproTech, Rocky Hill, N.J.; fMLP, $10^{-7}$M; PMA, 100 ng/ml). After a time point was reached, samples were placed on ice immediately and aliquots were added to individual wells of a U-bottom microtiter plate on ice containing MAb. In some cases, after a time point was reached cells were fixed immediately with paraformaldehyde (2%) and incubated for 30 minutes on ice. Immunofluorescence and flow cytometry was performed as described (Diamond et al., *J. Cell. Biol.* 111:3129–3139 (1990)). The protocol for conversion of logarithmic fluorescence into linear fluorescence has been described (Schmid et al., *Cytometry* 9:533–538 (1988)).

Adhesion Assays

Purified fibrinogen (2.0 mg/ml, in PBS, Sigma Chemical Co., St. Louis, Mo.) or purified sICAM-1 (200 μg/ml in PBS) were spotted (25 μl) onto 6 cm bacterial Petri dishes (Fisher 1007) for 90 minutes at room temperature. Plates were blocked with the detergent Tween 20 as described (Diamond et al., *Cell* 65:961–971 (1991)). Neutrophils ($4 \times 10^6$ cells in 1 ml) were resuspended in HBSS, 10 mM HEPES pH 7.3, 1 mM $MgCl_2$ and preincubated with MAbs for 10 minutes at room temperature. Subsequently, cells were added to the dishes in the presence or absence fMLP ($10^{-7}$M, final volume of 3 ml), and allowed to adhere for four minutes. Non-adherent cells were removed by twelve washes with a Pasteur pipette after gentle swirling with same buffer supplemented with 0.5% BSA. Binding was quantitated by scoring the number of adherent cells of at least four different fields using an ocular grid at 100× magnification. The percent inhibition by MAb was determined upon comparison with the media control.

The binding of ICAM-1$^+$ L cells is a modification of previously described protocols (Diamond et al., *J. Cell Biol.* 111:3129–3139 (1990)). Briefly, purified Mac-1 was diluted and adsorbed (30 μl) to 6 cm Petri dishes. After a 90 minute incubation at room temperature, non-specific binding sites were blocked with 0.5% heat-treated BSA. ICAM-1$^+$ L cells, after removal from tissue culture plates with trypsin-EDTA (GIBCO, Long Island, N.Y.), were washed twice and resuspended in PBS, 2 mM $MgCl_2$, 0.5% heat-treated BSA ($0.5–1.0 \times 10^6$ cells/ml). Thirty minutes prior to the binding assay, the Petri dishes or cells were preincubated at room temperature with MAb (1/200 dilution of ascites or 20 μg/ml of purified MAb) in PBS, 2 mM $MgCl_2$, 0.5% heat-treated BSA (2 mls). Cells (1 ml) were added to Petri dishes, and incubated for 60 minutes at 37° C. The Petri dishes then were swirled and non-adherent cells were removed by tipping the plate at an angle, removing the binding buffer with a Pasteur pipette, and adding fresh media (3 ml) to the edge of the dish. This procedure was repeated five times. Subsequently, the number of adherent cells was determined by light microscopy at 100× using an ocular grid. The percentage binding was normalized to a media control.

RESULTS

MAb to a neoepitope on Mac-1

Figure 1A:
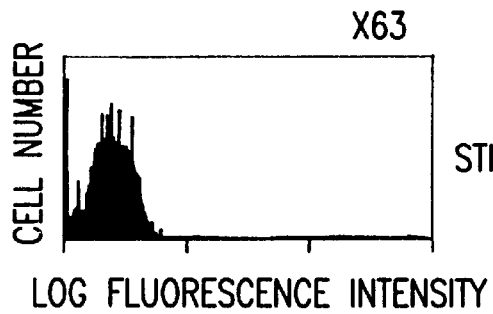
FIG. 1A–1F. A. Immunofluorescence flow cytometry of peripheral blood neutrophils that were unstimulated or treated with PMA (100 ng/ml) for ten minutes at 37° C. Neutrophils were stained with either a negative control (X63), a MAb to Mac-1 α subunit (LM2/1), or CBRM1/5. B. Immuno-precipitation of Mac-1 from TRITON X 100 detergent lysates of $^{125}$I-labelled peripheral blood neutrophils. Immunoprecipitates with the following MAbs were subjected to reducing SDS-5% PAGE and autoradiography.
Figure 1B:
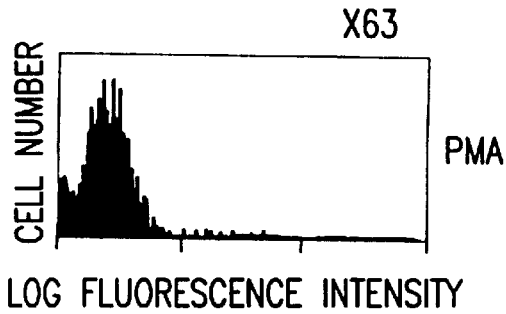
Figure 1C:
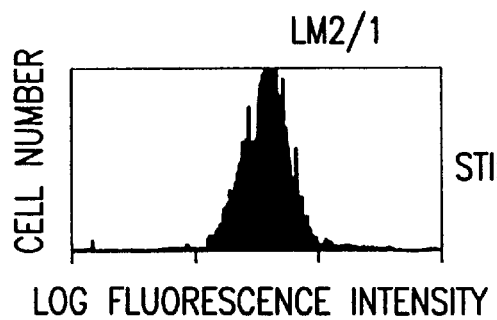
Figure 1D:
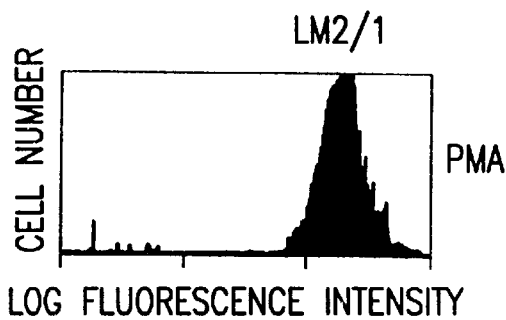
Figure 1E:
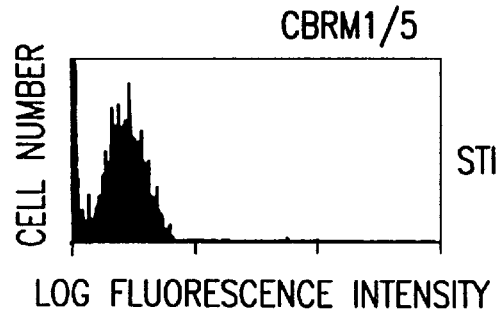
Figure 1F:
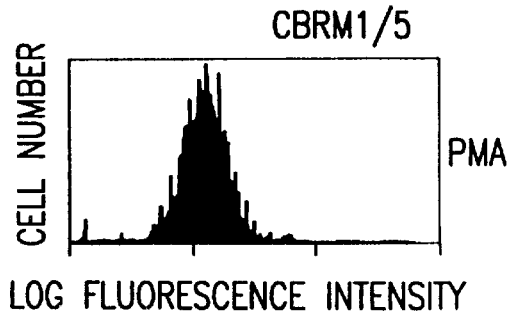
Figure 1G:
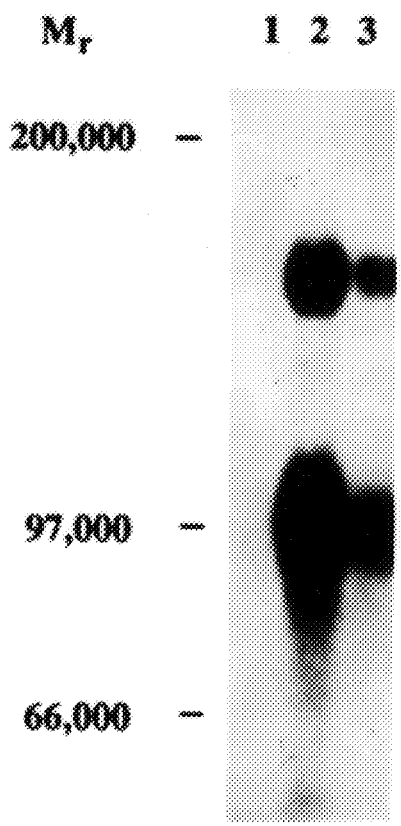

If a conformational change in Mac-1 was involved in the regulation of its adhesiveness, specific epitopes should be expressed on activated but not resting cells. To generate MAbs that recognize these activation-dependent epitopes, immunoaffinity purified Mac-1 that was judged functional by its capacity to bind several ligands (Diamond et al. *In Leukocyte Typing IV*, Knapp et al editors, Oxford University, London pages 570–574 (1989); Diamond et al., *J. Cell Biol.* 111:3129–3139 (1990)) was used to immunize BALB/c mice. Hybridomas were screened for their differential ability to bind to resting and phorbol ester-activated neutrophils. One MAb, CBRM1/5, showed little binding to resting neutrophils but bound to neutrophils that were stimulated with phorbol esters (FIGS. 1A–1F). CBRM1/5 bound to activated cells at a significantly lower level compared to previously characterized MAbs to Mac-1. Immunoprecipitation from detergent lysates of surface labelled neutrophils (FIG. 1G) or transfected COS cells (data not shown) confirmed that CBRM1/5 recognized Mac-1.

The lower level of expression of the CBRM1/5 epitope on PMA-stimulated neutrophils was not due to insufficient amounts of MAb, as studies by flow cytometry suggested that saturation was reached at 20 μg/ml (data not shown). This was confirmed by binding experiments with $^{125}$I-CBRM1/5 and $^{125}$I-LM2/1. CBRM1/5 bound specifically to activated (fMLP or PMA) neutrophils but not to resting neutrophils (FIG. 2a and 2b, note difference in scale, and Table 1). Despite the lower absolute numbers of binding sites, the binding of CBRM1/5 was saturable, and of comparable affinity ($K_d$=15 nM) to LM2/1 ($K_d$=2 nM). Neutrophils stimulated with fMLP or PMA had a total Mac-1 site density of 139,000 and 197,000 sites/cell (determined with LM2/1) but a CBRM1/5 neoepitope site density of 13,000 to 57,000 sites/cell, respectively (Table 1). Bivalent binding of CBRM1/5 to Mac-1 was not strictly required, because monovalent Fab' fragments of CBRM1/5 bound specifically to activated neutrophils and displaced ($K_i$ of Fab'=200 nM) bivalent CBRM1/5 IgG (FIG. 2D, and data not shown).

Kinetics and Temperature Studies

IL-8, fMLP, or PMA prompted a time dependent increase in expression of the CBRM1/5 epitope that plateaued after 10 minutes (FIG. 3). In all cases, CBRM1/5 reacted with a subset of the LM2/1-reactive Mac-1 molecules on the cell surface.

MAb binding studies were carried out at different temperatures to determine whether the CBRM1/5 epitope expression correlated with an increase in surface expression or the activation of Mac-1 (FIG. 4). Elevating the temperature from 4° to 37° C. increases the surface expression of Mac-1 but does not necessarily promote Mac-1-dependent adhesion (Buyon et al., *J. Immunol.* 140:3156–3160 (1988); Lo et al., *J. Exp. Med.* 169:1779–1793 (1989), and Schleiffenbaum et al., *J. Immunol.* 142:3537–3545 (1989)). This temperature-dependent increase is primed by preparative procedures. We found that raising the temperature from 4° C. to 37° C. significantly increased the overall amount of surface Mac-1 whereas expression of the CBRM1/5 epitope remained virtually absent on both monocytes FIG. (4a) and neutrophils (FIG. 4b). In contrast, in both monocytes and neutrophils, fMLP triggered expression of the CBRM1/5 epitope. These experiments suggest that the expression of CBRM1/5 is associated with the activation of Mac-1.

Epitope Mapping of CBRM1/5 on Transfected Cells

We examined the expression of CBRM1/5 on CHO cells that were transfected with wild type and chimeric Mac-1 molecules (FIG. 5). A subset of Mac-1 molecules on transfected CHO cells constitutively expressed the CBRM1/5 epitope. This agrees with our previous observations that the activation MAb NKI-L16 reacted constitutively with a subset of LFA-1 molecules on transfected COS cells (Larson et al., *Cell Reg.* 1:359–367 (1990)Keizer et al., *J. Immunol.* 140:1393–1400 (1988)). CHO cell transfectants that express wild type Mac-1 are functional as they rosetted with iC3b coated erythrocytes, bound Leishmania promastigotes, and adhered to purified ICAM-1 (data not shown). CBRM1/5 localized specifically to the I domain of the Mac-1 α chain as it, like LM2/1, bound to CHO cells that expressed the wild type Mac-1 and chimera X-e-M-b-X which contains the I domain of Mac-1 on a p150,95 frame. In contrast, CBRM1/5 did not bind to wild type p150,95 or the reciprocal chimera, M-e-X-b-X which contains a p150,95 I domain on a Mac-1 backbone (FIG. 5).

Effect of Divalent Cations on CBRM1/5 Expression

For integrins to bind to their ligands, divalent cations are required. Adhesion is abolished uniformly by the presence of EDTA and altered quantitatively by the type of divalent cation that is present (Gailit et al., *J. Biol. Chem.* 263:12927–12932 (1988); Diamond et al., In *Leukocyte Typing IV*, Knapp et al editors, London, Oxford University, pp. 570–574 (1989); Altieri, D. C. *J. Immunol.* 147:1891–1898 (1991) and Dransfield et al., *J. Cell. Biol.* 116:219–226 (1992)). We tested the CBRM1/5 and LM2/1 epitopes for their sensitivity to different divalent cations. For binding to cell surface (FIGS. 6a) or purified Mac-1 (FIG. 6b), the presence of divalent cations was required for CBRM1/5 epitope expression but not for LM2/1. EDTA (5 mM) abrogated the expression of CBRM1/5 but only slightly reduced expression of LM2/1. Neutrophils stimulated with fMLP expressed the neoepitope better in the presence of $Ca^{2+}$ than in $Mg^{2+}$ alone but in other studies, CBRM1/5 was expressed better on neutrophils stimulated with PMA in the presence of $Mg^{2+}$ alone (data not shown). $Mn^{2+}$, which is reported to enhance Mac-1 adhesive function in vitro (Altieri, D. C. *J. Immunol.* 147:1891–1898 (1991)), augmented the expression of CBRM1/5 on purified Mac-1 and promoted the expression of the epitope on resting neutrophils. Unlike the Mac-1 on neutrophils, Mac-1 that was purified by immunoaffinity chromatography expressed equivalent levels of the CBRM1/5 and LM2/1 epitopes in the presence of divalent cations. In contrast, Mac-1 that was purified by iC3b-Sepharose chromatography (Hermanowski-Vosatka et al., *Cell* 68:341–352 (1992)) expressed the LM2/1 epitope but lacked the CBRM1/5 epitope, and was unable to sustain ligand binding (M S Diamond, K P M van Kessel, S D Wright, and T A Springer, unpublished observations).

Structural subsets of Mac-1

To determine whether CBRM1/5 recognized a subset of Mac-1 molecules, sequential immunoprecipitation experiments were performed (FIG. 9). After preclearing a neutrophil lysate twice with CBRM1/5-Sepharose so that negligible amounts of CBRM1/5 reactive Mac-1 remained, LM2/1-Sepharose immunoprecipitated a significant quantity of Mac-1. However, if the lysate was precleared with LM2/1-Sepharose first, CBRM1/5-Sepharose was unable to immunoprecipitate any additional Mac-1. These experiments suggest that CBRM1/5 recognizes a subset of the LM2/1 reactive Mac-1 molecules in the cell lysate.

Functional effects of CBRM1/5

Bivalent IgG, $Fab_2$, or monovalent Fab fragments of CBRM1/5 inhibited greater than 80% of the Mac-1-dependent binding of fMLP-stimulated neutrophils to ICAM-1 (FIG. 10c). CBRM1/5 was comparable in effectiveness, to LPM19c, a MAb to Mac-1 that binds a similar number of sites/cell as LM2/1 and completely blocks Mac-1-ICAM-1 interaction (FIG. 10a, (Diamond, et al., *J. Cell Biol.* 111:3129–3139 (1990)), and data not shown). As a control, a third MAb to Mac-1, CBRM1/23, had no significant inhibitory effect on neutrophil adhesion to ICAM-1. When CBRM1/5 was added to a blocking MAb to LFA-1 (TS1/222), similar to the case with LPM 19c (Diamond, et al., *Cell* 65:961–971 (1991)), the combination of MAbs virtually abolished neutrophil binding to ICAM-1. The ability of CBRM1/5 to inhibit Mac-1 dependent neutrophil interaction with ICAM-1 was confirmed in binding assays with purified Mac-1 (FIG. 10b). Preincubation of purified Mac-1 with CBRM1/5 completely abolished $ICAM-1^+$ L adhesion.

When we tested the effect of CBRM1/5 on fMLP stimulated neutrophil adhesion to purified fibrinogen, nearly complete abolition of binding was also observed. Saturating concentrations of CBRM1/5 IgG, $F(ab')_2$, or Fab blocked adhesion to fibrinogen approximately 90%, and half-maximal blocking was observed at an IgG concentration of approximately 1 µg/ml (FIG. 10c, and data not shown). Again, other MAbs to Mac-1 (CBRM1/23) used at similar concentrations showed little inhibitory effect (data not shown). Thus, the 10% subset of Mac-1 molecules present on neutrophils after fMLP stimulation which are identified by CBRM1/5 mediates at least 90% of the adhesive activity of Mac-1.

DISCUSSION

Disclosed herein is the characterization of a novel MAb, CBRM1/5, that binds to a subpopulation of Mac-1 molecules on activated, but not resting peripheral blood neutrophils and monocytes. This MAb recognizes an activation-dependent neoepitope and acts as a reporter for the activation state of Mac-1. Our results demonstrate that the subset which expresses the CBRM1/5 neoepitope contains the structurally active Mac-1 molecules that sustain adhesion to at least two of its characterized ligands, ICAM-1 and fibrinogen. Evidence for this includes the following: (i) CBRM1/5 does not react by immunofluorescence with Mac-1 on the surface of resting neutrophils or monocytes. However, stimulation with the chemoattractant fMLP, the chemoattractive cytokine IL-8, or phorbol esters rapidly promotes expression of the epitope on a subset of Mac-1 molecules. The time course of expression of the neoepitope and adhesive activity of Mac-1 (Anderson, et al., *J. Immunol.* 137:15–27 (1986); Detmers, et al., *J. Exp. Med.* 171:1155–1162 (1990)) are parallel as both occur within two minutes. (ii) The quantitation of site densities by saturation binding experiments with $^{125}$I-labelled MAbs to Mac-1 demonstrates that resting neutrophils express approximately 12,000 LM2/1 binding sites/cell but no specific CBPM1/5 sites/cell. Treatment with fMLP and PMA increases the overall site density of Mac-1 (as reported by LM2/1) greater than tenfold as has been described (Berger, et al., *J. Clin. Invest.* 74:1566–1571 (1984); Lo et al., *J. Exp. Med.* 169:1779–1793 (1989); Miller, et al., *J. Clin. Invest.* 80:535–544 (1987); Todd, et al., *J. Clin. Invest.* 74:1280–1290 (1984)), and induces expression of the CBRM1/5 neoepitope on 10–30% of these molecules (13,000–57,000 sites/cell after stimulation). (iii) Sequential immunoprecipitation confirms that CBRM1/5 recognizes a structural subset of Mac-1 molecules on neutrophils. Lysates that are precleared of the CBRM1/5 epitope contain residual Mac-1 molecules that are immunoprecipitated by LM2/1 but lysates that are precleared of Mac-1 containing the LM2/1 epitope do not contain residual quantities of CBRM1/5 precipitable material. (iv) Functional studies reveal that despite binding to less than 15% of Mac-1 molecules on neutrophils stimulated with fMLP, CBRM1/5 (IgG or Fab fragments) inhibits almost completely (>85%) the Mac-1-dependent adhesion to fibrinogen and ICAM-1. Additional experiments confirmed the blocking capacity of CBRM1/5, as it abrogates adhesion of ICAM-1+L cells to purified Mac-1.

While several MAbs have been characterized that block Mac-1-dependent adhesion to ICAM-1 and fibrinogen (Altieri, et al., *J. Biol. Chem.* 265:12119–12122 (1990); Diamond, et al., *J. Cell Biol.* 111:3129–3139 (1990); Smith, et al., *J. Clin. Invest.* 83:2008–2017 (1989); Wright, et al., *Proc. Natl. Acad. Sci. USA* 85:7734–7738 (1988)), CBRM1/5 is unique as it recognizes the subset of Mac-1 molecules that mediates ligand interaction. CBRM1/5 maps to the I domain on Mac-1 which appears to contain the major recognition site for ICAM-1 and fibrinogen (described below). Not all MAbs, however, which bind to subsets of Mac-1 molecules recognize functional epitopes. We have generated two additional MAbs (anti-CD18, CBRM1/19; anti-CD11b, CBRM1/28) that bind to activated but not resting neutrophils that do not block function (M S Diamond and T A Springer, unpublished data). The finding of structurally distinct subsets of Mac-1 molecules may explain why neutrophils do not show significant changes in the redistribution of surface Mac-1 after activation with fMLP (Detmers, et al., *J. Cell Biol.* 105:1137–1145 (1987); Smith et al., *J. Clin. Invest.* 65:804–812 (1980)).

Although activation of neutrophils and monocytes with chemotactic factors, cytokines, nucleotides, or phorbol esters increases the avidity of Mac-1 for several of its ligands (Altieri, et al., *J. Cell. Biol.* 107:1893–1900 (1988); Altieri et al., *J. Biol. Chem.* 263:7007–7015 (1988); Diamond, et al., *J. Cell Biol.* 111:3129–3139 (1990); Philips, et al., *J. Clin. Invest.* 82:495–501 (1988); Smith, et al., *J. Clin. Invest.* 83:2008–2017 (1989); Wright et al. *J. Immunol.* 136:1759–1764 (1986); Wright, et al., *Proc. Natl. Acad. Sci. USA* 85:7734–7738 (1988)), the molecular basis for this change has remained unclear. The quantitative increase in Mac-1 expression on neutrophils does not correlate directly with adhesive functions (Buyon, et al., *J. Immunol.* 140:3156–3160 (1988); Lo et al., *J. Exp. Med.* 169:1779–1793 (1989); Vedder et al., *J. Clin. Invest.* 81:676–682 (1988)) but until now, no direct evidence has been obtained for a structural change. Studies at 4° C., 25° C., and 37° C. show that an increase in overall Mac-1 expression does not induce the CBRM1/5 epitope on neutrophils or monocytes. Similarly, an increase in Mac-1 surface expression is not sufficient to promote Mac-1-dependent adhesion to ICAM-1, fibrinogen, or other ligands (Buyon, et al., *J. Immunol.* 140:3156–3160 (1988), Vedder et al., *J. Clin. Invest.* 81:676–682 (1988)), and M S Diamond, unpublished observations). Adhesion to fibrinogen and ICAM-1, and expression of the CBRM1/5 epitope both require cell stimulation. We suggest that activation prompts a subset of Mac-1 molecules to acquire the functionally relevant CBRM1/5 epitope, and to become competent structurally to bind to ICAM-1 and fibrinogen.

Several other MAbs against activation-dependent neoepitopes on integrin superfamily members have been described recently. MAbs against the platelet integrin gpIIb-IIIa have been reported to monitor structural changes that are induced either by cellular activation or ligand binding (Du et al., *Cell* 65:409 (1991)). Indeed, the initial evidence for a structural change in integrins came from the development of the PAC-1 MAb that recognizes gpIIb-IIIa on ADP, epinephrine, or thrombin-treated but not resting platelets (O'Toole, et al., *Cell Reg.* 1:883–893 (1990); Shattil, et al., *J. Biol. Chem.* 260:11107–11114 (1985)). PAC-1 binds to a subset (20–50%) of gpIIb-IIIa molecules after stimulation and inhibits fibrinogen-mediated platelet aggregation (Shattil, et al, *J. Biol. Chem.* 260:11107–11114 (1985)). Furthermore, CHO cells that express gpIIb-IIIa are unable to bind soluble fibrinogen or the PAC-1 MAb until a structural change has occurred (O'Toole, et al., *Cell Reg.* 1:883–893 (1990)). Additional evidence for structural changes has come from the characterization of a class of MAbs that recognize ligand-induced binding sites (LIBS) on gpIIb-IIIa (Frelinger et al., *J. Biol. Chem.* 265:In press (1990)). The generation of MAbs to multiple conformations of gpIIb-IIIa suggests that cell activation and ligand binding may effect distinct structural changes that facilitate adhesion and mediate function (Frelinger et al., *J. Biol. Chem.* 266:17106–17111 (1991)). Because PAC-1 and CBRM1/5 share similar binding properties, we suggest that the leukocyte integrins, like the platelet integrins, require similar structural changes to promote adhesion.

Several activation-dependent epitopes on leukocyte integrins also have been described. The MAb 7E3, that was raised originally against gpIIb-IIIa (Coller, *J. Clin. Invest.* 76:101–108 (1985)), binds to all Mac-1 molecules on ADP-stimulated but not resting monocytes or monocyte cell lines (Altieri et al., *J. Immunol.* 141:2656–2660 (1988)). Unlike PAC-1 or CBRM1/5, it has no reported functional effects. The NKI-L16 MAb recognizes the leukocyte integrin LFA-1 on resting T lymphocytes only weakly (Larson et al., *Cell Reg.* 1:359–367 (1990); van Kooyk, et al., *J. Cell Biol.* 112:345–354 (1991)), but binds to T lymphocytes that have been activated with phorbol esters, IL-2, or MAbs that crosslink CD3. NKI-L16 induces homotypic adhesion of B cell lines and T cell clones and restores partially binding to purified ICAM-1 of COS cells that have been transfected with a wild type LFA-1 chain and a defective CD18 β subunit (Hibbs et al., *Science* 251:1611–1613 (1991)). The NKI-L16 epitope, however, is not sufficient for cell binding since cloned T cells express high levels constitutively but do not aggregate spontaneously (van Kooyk, et al., *J. Cell Biol.* 112:345–354 (1991)). The MAb KIM 127 recognizes the common CD18 β subunit of the leukocyte integrins and promotes LFA-1 and Mac-1 dependent adhesive events (Robinson, et al., *J. Immunol.* 148:1080–1085 (1992)). Binding of this MAb may trigger a conformational change that mimics activation, and increases avidity for ligand. In comparison with these activation-dependent MAbs against leukocyte integrins, CBRM1/5 appears unique as it binds to a subset of molecules on stimulated cells, blocks rather than promotes adhesion, and has an epitope whose presence correlates with, but does not induce, the highly avid form of Mac-1 on neutrophils and monocytes.

Recent studies have begun to address the structural events that effect the increase in avidity. One model is that stimulation of cells promotes or alters the divalent cation binding by an integrin, and this event triggers the high avidity conformation (Altieri, *J. Immunol.* 147:1891–1898 (1991); Dransfield, et al., *J. Cell Biol.* 116:219–226 (1992); Dransfield et al., *EMBO J.* 8:3759–3765 (1989)). Integrin a chains contain a region of extensive homology to the divalent cation binding sites on $Ca^{2+}$ regulatory proteins (Argraves, et al., *J. Biol. Chem.* 261:12922–12924 (1986); Corbi, et al., *EMBO J.* 6:4023–4028 (1987); Poncz, et al., *J. Biol. Chem.* 262:8476–8482 (1987); Suzuki, et al., *J. Biol. Chem.* 262:14080–14085 (1987)), and numerous studies demonstrate a requirement for divalent cations in integrin function (Altieri, *J. Immunol.* 147:1891–1898 (1991); Bajt, et al., *J. Biol. Chem.* 267:3789–3794 (1992); Dransfield, et al., *J. Cell Biol.* 116:219–226 (1992); Elices et al., *J. Cell Biol.* 112:169–181 (1991); Gailit et al., *J. Biol. Chem.* 263:12927–12932 (1988); Hynes, R. O., *Cell* 48:549–554 (1987); Kirchhofer et al., *J. Biol. Chem.* 266:4471–4477 (1991); Loftus, et al., *Science* 249:915–918 (1990); Martz, *Human Immunol.* 18:3–37 (1987); Rothlein et al., *J. Exp. Med.* 163:1132–1149 (1986); Sonnenberg, et al., *Nature* 336:487–489 (1988)). Several activation-dependent neoepitopes on leukocyte integrins have been shown to require the presence of divalent cations. Binding of the MAb 24 (Dransfield, et al., *J. Cell Biol.* 116:219–226 (1992); Dransfield et al., *EMBO J.* 8:3759–3765 (1989)), which recognizes a common determinant on the a chain of the three leukocyte integrins, requires either $Mg^{2+}$ or $Mn^{2+}$, but is abolished in the presence of $Ca^{2+}$. In contrast, expression of the NKI-L16 epitope requires $Ca^{2+}$ as it is abolished in the presence of EGTA or EDTA (van Kooyk, et al., *J. Cell Biol.* 112:345–354 (1991)). CBRM1/5 is the first example of an activation-specific MAb against an integrin a subunit whose expression requires divalent cations but is known to bind to a region outside the divalent cation binding repeats. $Mg^{2+}$ or $Ca^{2+}$ is sufficient and EDTA abolishes the expression of the CBRM1/5 epitope; on neutrophils, $Mn^{2+}$ increases the CBRM1/5 epitope expression in the absence of stimulation, and thus may impose structural alterations that mimic cell activation (Altieri, *J. Immunol.* 147:1891–1898 (1991); Dransfield, et al., *J. Cell Biol.*116:219–226 (1992)). Although these studies suggest that divalent cations modulate integrin function, it remains unclear if they are permissive for ligand binding or whether divalent cations are involved actively in the regulation of adhesion.

While leukocyte trafficking is a protective response of the host defense system against foreign pathogens or tissue repair, under some circumstances leukocytes can mediate significant degrees of vascular and tissue injury. Neutrophils have been implicated in the pathogenesis of a number of clinical disorders including adult respiratory distress syndrome, ischemia-reperfusion injury following myocardial infarction, vasculitis, and shock (for review see Carlos et al., *Immunol. Rev.* 114:1–24 (1990)). Already, several groups have demonstrated that the inflammatory injury mediated by leukocytes can be attenuated by antibodies against the leukocyte integrins (Mileski, et al., *Surgery* 108:206–212 (1990); Rosen, et al., *J. Exp. Med.* 169:535–548 (1989); Simpson, et al., *J. Clin. Invest.* 81:624–629 (1988); Vedder, et al., *J. Clin. Invest.* 81:939–944 (1988)). MAbs like CBRM1/5, which recognize activated, and not resting leukocytes, are useful clinically to target, monitor or deplete the highly adhesive cells that effect inflammatory injury.

TABLE 1

Site Density of Mac-1 on Neutrophils

| | $^{125}$I-LM2/1<br>Sites/Cell | $^{125}$I-CBRM1/5<br>Sites/Cell |
|---|---|---|
| Unstimulated | 11,300 ± 1600 | No sites detected |
| fMLP | 138,700 ± 21000 | 13,200 ± 1400 |
| PPMA | 196,900 ± 800 | 57,200 ± 1300 |

The site densities were determined from the amount of MAb bound at saturation. Data (± standard error of the mean) are the average of two independent experiments performed in triplicate on a single donor.

EXAMPLE 2

IDENTIFICATION OF THE LIGAND BINDING DOMAINS OF MAC-1

Materials and Methods

MAbs

The following murine MAbs against human antigens were used from ascites: TS1/22 (anti-CD11a, IgG1) (Sanchez-Madrid, et al., *Proc. Natl. Acad. Sci. USA* 79:7489–7493 (1982)), LPM19c (anti-CD11b, IgG2a, a gift of Dr. K. Pulford, Oxford, UK) (Uciechowski and Schmidt, "Cluster Report: CD11, " in *Leucocyte Typing IV: White Cell Differentiation Antigens*, Knapp et al., eds., Oxford University Press, Oxford. 543–551 (1989)), TMG-65 (anti-CD11b, IgG1, a gift of Dr. I. Ando, Szeged, Hungary) (Uciechowski and Schmidt, "Cluster Report: CD11, " in *Leucocyte Typing IV. White Cell Differentiation Antigens*, Knapp et al., eds., Oxford University Press, Oxford. 543–551 (1989)), Mn41 (anti-CD11b, IgG1, a gift of Dr. J. Buyon, New York) (Eddy, et al., *Clin. Immunol. Immunopathol.* 31:371–389 (1984)), OKM10 (anti-CD11b, IgG2a, a gift of Dr. P. Rao, Ortho Pharmaceuticals, Raritan, N.J.) (Wright, et al., *Proc. Natl. Acad. Sci. USA* 80:5699–5703 (1983)), VIM 12 (anti-CD11b, IgG1) (Bernstein and Self, "Joint Report of the Myeloid Section of the Second International Workshop on Human Leukocyte Differentiation Antigens," in *Human Myeloid and Hematopojetic Cells*, Reinherz et al, eds., Springer-Verlag, N.Y. 1–25 (1986)), 14B6E.2 (anti-CD11b, IgM) and 5A4. C5 (anti-CD11b, IgG1), gifts of Dr. L. Ashman, Adelaide, Australia (Uciechowski and Schmidt, "Cluster Report: CD11, " in *Leucocyte Typing IV: White Cell Differentiation Antigens*, Knapp et al., eds., Oxford University Press, Oxford. 543–551 (1989)), CBRp150/4G1 (anti-CD11c, IgG2a) (Stacker et al., *J. Immunol.* 146:648–655 (1991)), L29 (anti-CD11c, IgG1) (Uciechowski et al., "Cluster Report: CD11, " in *Leucocyte Typing IV: White Cell Differentiation Antigens*, Knapp et al., eds., Oxford University Press, Oxford. 543–551 (1989)), BLY6 (anti-CD11c, IgG1) (Uciechowski et al., "Cluster Report: CD11, " in *Leucocyte Typing IV: White Cell Differentiation Antigens*, Knapp et al., eds., Oxford University Press, Oxford. 543–551 (1989)), TS1/18 (anti-CD18, IgG1) (Sanchez-Madrid et al., *Proc. Natl. Acad. Sci. USA* 79:7489–7493 (1982)). The following MAbs were used as purified IgG: R15.7 (anti-CD18, a gift of Dr. R. Rothlein, Boehringer- Ingelheim, Ridgefield, CT) (Entman, et al., *J. Clin. Invest.* 85:1497–1506 (1990)), OKM1 (anti-CD11b, IgG2a) (Wright, et al., *Proc. Natl. Acad. Sci. USA* 80:5699–5703 (1983)), OKM9 (anti-CD11b, IgG1, a gift of Dr. P. Rao, Ortho, Pharmaceuticals, Raritan, N.J.) (Wright, et al., *Proc. Natl. Acad. Sci. USA* 80:5699–5703 (1983)), LM2/1 (anti-CD11b, IgG1) (Miller, et al., *J. Immunol.* 137:2891–2900 (1986)), SHCL3 (anti-CD11c, IgG2b) (Schwarting, et al., *Blood* 65:974–983 (1985)). M1/87 (anti-Forssman antigen, IgM) (Springer, et al., *Eur. J. Immunol.* 8:539–551 (1978)) was used as a culture supernatant after treatment at 60° C. for 1 h. X63 (non-binding MAb, IgG1) was used as culture supernatant.

Generation of MAbs against human Mac-1 (CBRM 1 series) was based on a previously published protocol (Stacker et al., *J. Immunol.* 146:648–655 (1991)). In brief, female BALB/c mice were immunized with purified Mac-1 (2 µg/immunization) (Diamond, et al., *J. Cell Biol.* 111:3129–3139 (1990)) on day 31 (intraperitoneally) and day 3 (intraperitoneally and intravenously) prior to fusion with the non-secreting murine myeloma P3X63Ag8.653 (ATCC CRL 1580). Mac-1 was prepared for the first immunization by combining 10 µg of purified Mac-1 with trehalose dimycolate from *Mycobactefium phlei*, monophosphoryl lipid A from *Salmonella Minnesota* R595, PBS, 0.2% Tween 80, and squalene as described in the manufacturer's instructions (RIBI Immunochemical Research, Hamilton Minn.). The second immunization was performed in PBS. Mice were test bled on day 8 prior to fusion and the titer of the antisera by ELISA against purified Mac-1 was 1/5000. The protocol for fusion and hybridoma maintenance has been described (Springer, et al., *Eur. J. Immunol.* 9:301–306 (1979)).

Indirect immunofluorescence flow cytometry was used to identify hybridomas that produced MAbs which bound to peripheral blood neutrophils (Diamond, et al., *J. Cell Biol.* 111:3129–3139 (1990)). Of the 500 hybridoma supernatants examined approximately 20% contained MAbs that bound to neutrophils. These were tested subsequently for their ability to bind to peripheral blood lymphocytes, and Mac-1 or p150,95 transfected COS or CHO cells to determine whether the MAb recognized the α or β chain of Mac-1. 24 MAbs were subcloned and determined to be specific for the Mac-1 α subunit. MAbs were isotyped using an Immunopure MAb Isotyping Kit (Pierce, Rockford Ill.).

Generation of Mac-1/p150,95 Chimeras

For production of chimeric Mac-1 and p150,95 α chains, oligonucleotide directed mutagenesis (Kunkel, *Proc. Natl. Acad. Sci. USA* 82:488–492 (1985); Peterson et al., *Nature* 329:842–846 (1987)) was used to introduce restriction sites into homologous regions of the cDNA without altering the coding sequence of $\alpha^M$ (Mac-1) (Corbi, et al., *J. Biol. Chem.* 263:12403–12411 (1988)) and $\alpha^X$ (p 150,95) (Corbi, et al., *EMBO J.* 6:4023–4028 (1987)) in pCDM8. The nucleotide sequence numbering was according to the published cDNA clones (Corbi, et al., *J. Biol. Chem.* 263:12403–12411 (1988); Corbi, et al., *EMBO J.* 6:4023–4028 (1987)). Changes were introduced at the following nucleotide sequences to facilitate reciprocal exchanges: EcoRV ($\alpha^M$ bp 520–525, GACATT is changed to GATATC; $\alpha^X$ bp 515–520, GACATT is changed to GATATC), BglII ($\alpha^M$ bp 1064–1069, AGATCT is native; $\alpha^X$ bp 1059–1064, AGATCT is native), and AflII ($\alpha^M$ bp 1908–1913, GCTCAG is changed to CTfAAG; $\alpha^X$ bp 1900–1905, GCTCAG is changed to CTTAAG). These sites were selected to bracket the I domain and divalent cation binding regions based on amino acid sequence homology patterns among the leukocyte integrin family (Larson, et al., *J. Cell Biol.* 108:703–712 (1989)). Genomic cloning of p150,95 (Corbi, et al., *J. Biol. Chem.* 265:2782–2788 (1990)) identified the exon-intron boundaries that distinguish these regions and confirmed that EcoRV and BglII bracket the I domain: the EcoRV site is located 23 nucleotides into the first exon (exon 7) of the I domain and the BglII site is 15 nucleotides before the end of the last exon (exon 10) of the I domain. The BglII and AflII restriction sites define a region that contains exons 11 to 13 and the three divalent cation binding repeats (exons 14 to 16): for simplicity this will be referred to as the divalent cation binding region: the BglII site is 10 nucleotides before the end of exon 10 and the AflII site is precisely at the end of the last exon (exon 16) of the divalent cation binding repeats (Corbi, et al., *J. Biol. Chem.* 265:2782–2788 (1990)). Mac-1 α subunits that contained silent mutations were intact antigenically and functionally as they bound iC3b-E and appropriate α chain specific MAbs after transfection into COS cells (data not shown).

For all chimeras, M represents a region of the Mac-1 α subunit, X represents a region of the p150,95 α subunit, and e, b, and a refer to the restriction sites EcoRV, BglII, and AflII. M-e-X and X-e-M were constructed by ligating the EcoRV/NotI fragments of pCDM8-$\alpha^M$ (4.7 kb) or pCDM8-$\alpha^X$ (4.1 kb) with the NotI/EcoRV fragments (3.5 or 4.7 kb) of pCDM8-$\alpha^X$ or pCDM8-$\alpha^M$. M-b-X and X-b-M, or M-a-X and X-a-M were constructed similarly using the BglII/NotI or the Afill/NotI fragments of the corresponding plasmids. M-b-X-a-M and X-b-M-a-X were constructed by ligating the 0.8 kb BglII/AflII of $\alpha^M$ or $\alpha^X$ with the AflII/BglII fragment of pCDM8-$\alpha^X$ (6.7 kb) or pCDM8-$\alpha^M$ (7.2 kb). M-e-X-b-M was constructed by ligating a SalI/EcoRV (4.5 kb) fragment of pCDM8-$\alpha^M$ with a BglII/SalI fragment (3.0 kb) of pCDM8-$\alpha^M$ and a EcoRV/BglII (0.5 kb) fragment of $\alpha^X$. X-e-M-b-X was constructed by ligating a EcoRV/BglII fragment (0.5 kb) of $\alpha^M$ with the BglII/EcoRV fragment (7.0 kb) of pCDM8-$\alpha^X$. The construction of each chimera was confirmed by restriction digest analysis, hybridization with appropriate segments of cDNA, and by sequencing through the junctions (Maniatis, et al., *Molecular Cloning: A Laboratory Manual*, Cold Spring Harbor Laboratory, Cold Spring Harbor, N.Y. (1982)).

Tissue Culture. Transfection. and Cell Preparation

Neutrophils were isolated from whole blood of healthy volunteers by dextran sedimentation, Ficoll gradient centrifugation, and hypotonic lysis as described (English et al., *J. Immunol. Methods* 5:249 (1974); Miller, et al., *J. Clin. Invest.* 80:535–544 (1987)). Prior to experimentation, cells were stored at room temperature in HBSS, 10 mM HEPES pH 7.3, 1 mM $MgCl_2$ in polypropylene tubes (Falcon 2097, Becton Dickinson, Lincoln Park, N.J.).

COS cells were grown on 15-cm tissue culture treated plates in RPMI 1640, 10% FCS (JRH Biosciences, Lenexa, KS), 2 mM glutamine, and 50 µg/ml gentamicin, and then co-transfected with CsCl purified $\alpha^M$, $\alpha^X$ or chimeric $\alpha^{M/X}$ and the common β (Kishimoto, et al., *Cell* 48:681–690. (1987)) cDNA in pCDM8 by the DEAE-Dextran method as described (Staunton, et al., *Cell* 61:243–254 (1990)). Surface expression was monitored three days after transfection by flow cytometry as described (Diamond, et al., *J. Cell Biol.* 111:3129–3139 (1990)).

CHO DG 44 cells which have a deletion of the DHFR gene were obtained from Dr. L.Chasin (Columbia University, New York N.Y.) and maintained as described (Qu, et al., *J. Exp. Med.* 167:1195–1210 (1988)). Cells were cotransfected by electroporation at 380 V and 960 µF (Chan et al., *Mol. Biol. Cell* 3:157–166 (1992)) with 25 µg of wild type or chimeric α in pCDM8, 25 μg of wild type β in pCDM8, and 5 μg of pDCHIP vector that contains a CHO DHFR minigene. Cells were initially selected in α-MEM, 10% dialyzed FCS (JRH Biosciences, Lenexa, Kans.) that lacked hypoxanthine but was supplemented with 16 μM thymidine, 2 mM glutamine, and 50 μg/ml gentamicin. After ten days, selection was augmented by the addition of methotrexate (0.02 μM). After two weeks of growth in media containing methotrexate, cells were detached with HBSS, 5 mM EDTA and incubated with MAbs against either Mac-1 or p150,95 (depending on the chimera) at 4° C. for 30 minutes. Cells were washed thrice in A-MEM, 2.5% dialyzed FCS, and panned for five minutes at room temperature on 10 cm non-tissue culture treated plates (Lab-Tek 4026, Nunc, Inc., Naperville, Ill.) that were coated with 50 μg/ml rabbit anti-mouse IgG (Zymed Laboratories, San Francisco, Calif.) and blocked with 10% FCS. Non-adherent cells were removed by eight changes of media, and adherent cells were recovered after treatment with trypsin-EDTA. Cells were cultured and the panning procedure was repeated several days later. High expressing cells were generated by increasing the concentration of methotrexate (0.02–0.20 μM) in culture. As controls, CHO cells expressing a domain deleted form of ICAM-1 (Domain 3 deleted, F185) (Staunton, D. E., et al., *Cell* 56:849–853 (1989)) were generated by cotransfection of F185 cDNA in pCDM8 with pDCHIP followed by selection and immunopanning as described. For all transfectants, positive surface expression was monitored by immunofluorescent flow cytometry.

The ICAM-1$^+$ L cell stables were maintained on 15 cm tissue culture plates in DME, 10% heat inactivated FCS (Low endotoxin serum (defined), Hyclone Laboratories, Logan, Utah), 2 mM glutamine, and 50 μg/ml gentamicin as previously described (Diamond, et al., *J. Cell Biol.* 111:3129–3139 (1990)). Prior to adhesion assays, cells were removed from tissue culture plates with trypsin-EDTA, and washed twice in PBS, 2 mM MgCl$_2$, 0.5% heat-treated BSA (Diamond, et al., *J. Cell Biol.* 111:3129–3139 (1990)).

Surface Labelling, Immunoprecipitation, and Gel Electrophoresis

Transfected COS or CHO cells (1–2×10$^6$ cells) were detached with HBSS, 5 mM EDTA, washed four times with PBS, and resuspended in 2 mls. The cells were iodinated, lysed, and precleared as described (Diamond, et al., *Cell* 65:961–971 (1991)). Immunoprecipitations were performed as follows: Immune complexes were formed by incubating MAb (250 μl volume of neat supernatant, 1/100 dilution of ascites, 25 μg/ml purified MAb) with purified rabbit anti-mouse antibody (5 μl of 1 mg/ml, Zymed Laboratories, San Francisco, Calif.) for 4 hours at 4° C. Protein-A SEPHAROSE (Pharmacia KLB, Piscataway, N.J.) (25 μl of a 1:1 slurry) was added for overnight incubation. Eppendorf tubes were centrifuged, supernatants were aspirated, and iodinated lysate (50 μl) was added and incubated for 2 hours at 4° C. while shaking vigorously. The washing and elution of the immunoprecipitates have been described (Diamond, et al., *Cell* 65:961–971 (1991)). Samples were loaded, and subjected to SDS-PAGE (Laemmli, *Nature* 227:680–685 (1970)) in the presence of 5% β-mercaptoethanol, and autoradiographed (Laskey et al. *FEBS Letters* 82:314–316 (1977)).

Purified Proteins

Mac-1 was purified from leukocyte lysates after detergent solubilization by LM2/1-Sepharose immunoaffinity chromatography as described (Diamond, et al., *J. Cell Biol.* 111:3129–3139 (1990)). ICAM-1 was purified from detergent lysates of the erythroleukemic cell line K562 by RR1/1-Sepharose immunoaffinity chromatography as described (Marlin et al., *Cell* 51:813–819 (1987)). Fibrinogen was obtained from Sigma Chemical Company (St. Louis, Mo.)

iC3b-E Preparation and Binding Assay

IgM and iC3b-coated erythrocytes (IgM-E, iC3b-E) were prepared as described previously (Rothlein et al., *J. Immunol.* 135:2668–2672 (1985)) with the following modifications. In some experiments, sheep erythrocytes (Colorado Serum Company, Denver, CO) were washed once in PBS, and labelled for 2 h at 37° C. with a 0.22 μm filtered solution of FITC (0.8 mg/ml in PBS after being dissolved in 30 1μl DMSO). Erythrocytes were washed thrice in HBSS, 10 mM HEPES pH 7.3, 2 mM MgCl$_2$, resuspended (6×10$^8$ cells in 10 mls) and incubated with a 1/128 dilution of heat inactivated anti-Forssman IgM MAb (M1/87) for 60 minutes at room temperature while shaking gently. IgM coated erythrocytes (IgM-E) were washed thrice, resuspended (1 ml) in HBSS, 10 mM HEPES, 1 mM MgCl$_2$, 1 mM CaCl$_2$ supplemented with C5 deficient human serum (100 μl) (Sigma Chemical Co, St. Louis, Mo.) and incubated for 60 minutes at 37° C. while rotating. iC3b coated erythrocytes (iC3b-E) and IgM-E were washed thrice and resuspended (4×10$^7$ cells/ml) in HBSS, 1 mM MgCl$_2$, 1mM CaCl$_2$, 10 mM HEPES pH 7.3.

Neutrophils and transfected CHO cells were assayed for binding to iC3b-E. Peripheral blood neutrophils (1.25×10$^5$ cells/well in 50 μl) were seeded onto 96-well tissue culture treated plates (Corning Glass Works, Corning, N.Y.) in HBSS, 10 mM HEPES pH 7.3, 1 mM MgCl$_2$, 1mM CaCl$_2$ for 20 minutes at 37° C. in a 5% CO$_2$ incubator; non-adherent cells were removed after two washes with the same buffer. Adherent neutrophils were preincubated with MAb (addition of 50 μl of diluted ascites or purified MAb in PBS, 1 mM MgCl$_2$, 0.5% BSA) for 20 minutes; each condition was performed in quintuplicate. Subsequently, iC3b-E or IgM-E (2×10$^6$ in 50 μl) and PMA (65 ng/ml final concentration) were added; the erythrocytes were centrifuged (300 RPM, 5 minutes, 4° C.) onto the neutrophils and the plates were incubated in a 37° C. water bath for 15 minutes. Non-adherent erythrocytes were removed by flicking the plates six times after addition of PBS, 1 mM MgCl$_2$, 0.5% BSA (175 μl/well). Bound cells were quantitated in the 96 well plates using a Pandex fluorescence concentration analyzer (Baxter Healthcare Corp., Mundelein, Ill.). The percentage of inhibition was normalized as follows:

% Inhibition = 100 ×

$$\frac{(\% \text{ iC3b-E binding without MAb} - \% \text{ iC3b-E binding with MAb})}{(\% \text{ ic3b-E binding without MAb})}$$

Transfected CHO cells (2×10$^5$ cells/ml in 250 μl) were seeded onto 6-well tissue culture treated plates in L15, 10 mM HEPES pH 7.3, 5% heat-inactivated FCS and adhered for greater than three hours at 37° C. Subsequently, iC3b-E or IgM-E (2×10$^8$/ml, 50 μl) and PMA (100 ng/ml final concentration) were added and cells were bound for 60 minutes at 37° C. Non-adherent erythrocytes were removed after six to eight washes and rosettes (>10 erythrocytes/CHO cell, >100 cells examined) were scored by light microscopy at 200× magnification.

Neutrophil Homotypic Adhesion Assays

Previously, two methods have been utilized to quantitate the effect of MAbs on neutrophil aggregation: microscopic determination of the number of free neutrophils (those not found in cell conjugates) (Diamond, et al., "Differential Effects on Leukocyte Functions of CD11a, CD11b, and CD18 Monoclonal Antibodies," in *Leukocyte Typing IV*, Knapp et al., eds., Oxford University, London, 570–574 (1989); Patarroyo, et al., *Scand. J. Immunol.* 22:171–182 (1985)) or aggregometry, which measures the relative increase in light transmission that occurs when cells go from a single cell dispersion to cell clusters (Anderson, et al., *J. Immunol.* 137:15–27 (1986); Buyon, et al., *J. Immunol.* 140:3156–3160 (1988); Hammerschmidt, et al., *Blood* 5:898–902 (1980)). While both methods are reproducible, the former is labor-intensive, and the latter only indirectly measures the number and size of cell aggregates. We devised an alternate method which uses a Coulter counter; it is automated, reproducible and scores mechanically the total number of cell particles in a fixed volume. Since the Coulter counter treats cell aggregates, regardless of size, as single particles, small numbers of two- or three-cell aggregates dramatically will affect the particle count. Thus, this assay is sensitive in distinguishing MAbs which block weakly from those which block strongly. Neutrophils ($2 \times 10^7$ cells/ml) were resuspended in HBSS, 10 mM HEPES, 1 mM $MgCl_2$, 1 mM $CaCl_2$, 0.5% HSA (HHMCH). Aliquots (0.325 ml) were preincubated with MAb (1/200 dilution of ascites, 20 µg/ml purified MAb) for 25 minutes at room temperature. These cells (0.3 ml) were then added to a pre-wet polypropylene eppendorf tube (1.5 ml) that contained 0.1 ml of HHMCH. PMA was added (100 ng/ml final concentration) and the tubes were rocked on their sides gently for 15 minutes at 37° C. on a Bellco Rocker Platform (Bellco, Vineland, N.J.). Subsequently, an aliquot (0.2 ml) was transferred to a conical tube (3 ml, Sarstedt, Germany) that contained HBSS, 10 mM HEPES, 2% paraformaldehyde (0.1 ml). The number of particles (single cells or cell aggregates) in a fixed volume was determined with a Model S-Plus Coulter counter (Coulter, Hialeah, Fla.). The average of two readings was used as an individual datapoint. Each condition was repeated at least three times with different donors. The percent aggregation was determined according to the following equation:

$$\% \text{ Aggregation} = 100 \times \left\{ 1 - \frac{(\# \text{ of particles in a sample stimulated with } PMA)}{(\# \text{ of particles in unstimulated sample})} \right\}$$

The percent inhibition was determined according to the following equation:

$$\% \text{ Inhibition} = 100 \times \frac{(\% \text{ aggregation } PMA \text{ sample} - \% \text{ aggregation } MAb \text{ sample} + PMA)}{(\% \text{ aggregation } PMA \text{ sample})}$$

Neutrophil aggregometry was performed as described (Hammerschmidt, et al., *Blood* 55:898–902 (1980)). Briefly, purified neutrophils were washed twice and resuspended ($10^7$ cells/ml) in HHMCH (without phenol red). Aliquots of cells (0.5 ml) were preincubated with MAbs for at least 25 minutes at room temperature. Neutrophils (0.4 ml) were stirred (700 RPM) at 37° C. in a siliconized cuvette in a standard platelet aggregometer (Model DP-247F, Sienco, Morrison, Colo.). A baseline was recorded for three minutes at which time PMA (100 ng/ml) was added and the change in light transmission was monitored on a strip chart recorder.

Adhesion of Neutrophils to Purified Fibrinogen

Purified fibrinogen was resuspended in PBS (2.0 mg/ml) and spotted (25 µl) onto 6 cm bacterial Petri dishes (Falcon 1007, Becton Dickinson, Lincoln Park, N.J.) for 90 minutes at room temperature. Plates were blocked with the detergent Tween 20 as described (Diamond, et al., *Cell* 65:961–971 (1991)). Neutrophils ($4 \times 10^6$ cells in 1 ml) were resuspended in HBSS, 10 mM HEPES pH 7.3, 1 mM $MgCl_2$ and preincubated with MAbs for 25 minutes at room temperature. Subsequently, cells were added to the dishes in the presence or absence of fMLP ($10^{-7}$ M, final volume of 3 ml), and allowed to adhere for three minutes and forty-five seconds. Non-adherent cells were removed by twelve washes with a Pasteur pipette after gentle swirling with the same buffer supplemented with 0.5% BSA. Binding was quantitated by scoring the number of adherent cells in at least four different fields using an ocular grid at 100× magnification. The percent inhibition by MAb was determined upon comparison with the media control.

Binding of ICAM-$1^+$ L Cells to Purified Mac-1

The binding of ICAM-$1^+$ L cells to Mac-1 is a modification of previously described protocol (Diamond, et al., *J. Cell Biol.* 111:3129–3139 (1990)). Briefly, purified Mac-1 was diluted, adsorbed (30 µl) to 6 cm Petri dishes and blocked with 0.5% heat-treated BSA as described (Diamond, et al., *J. Cell Biol.* 111:3129–3139 (1990)). Thirty minutes prior to the binding assay, the plates were preincubated at room temperature with MAb (1/200 dilution of ascites or 20 µg/ml of purified MAb) in PBS, 2 mM $MgCl_2$, 0.5% heat-treated BSA (PMBSA, 2 mls). ICAM-$1^+$ L cells were removed from tissue culture plates with trypsin-EDTA (GIBCO, Long Island, N.Y.), washed twice and resuspended in PMBSA ($0.5–1.0 \times 10^6$ cells/ml). Some aliquots were preincubated for 25 minutes at room temperature with control or anti-ICAM-1 MAbs. The binding assay was performed as described (Micklem, et al., *J. Immunol.* 144:2295–2303 (1990)). The percent inhibition by MAb was determined upon comparison with the media control.

Binding of CHO Cell Chimeras to Purified ICAM-1

The binding of transfected CHO cells to ICAM-1 is a modification of a previously described protocol for COS cell transfectants (Diamond, et al., *J. Cell Biol.* 111:3129–3139 (1990)). Briefly, purified ICAM-1 was diluted and adsorbed (25 µl) to 6 cm Petri dishes. After a 90 minute incubation, non-specific binding sites were blocked with 0.5% heat-treated BSA. CHO cell transfectants, after removal from tissue culture plates with HBSS, 10 mM HEPES pH 7.3, 5 mM EDTA, were washed twice and resuspended ($8 \times 10^5$ cells/ml) in HBSS, 10 mM HEPES pH 7.3, 1 mM $MgCl_2$, 0.5% heat treated BSA, and bound to ICAM-1 coated Petri dishes for 90 minutes at room temperature. Non-adherent cells were removed after five washes with a Pasteur pipette and the number of adherent cells was determined by light microscopy at 100× using an ocular grid.

RESULTS

Generation and Expression of Mac-1/p150,95 Chimeras

Naturally occurring restriction sites and sites introduced by silent mutations were used to divide the Mac-1 and p150,95 α subunits into four structurally distinct regions (FIG. 11). COS cells transiently transfected with the chimeric α subunits and the common CD18 β subunit were subjected to immunofluorescence flow cytometry and immunoprecipitation with a panel of previously characterized MAbs to the a subunits of Mac-1 and p150,95. Most of the chimeras were expressed on the cell surface and were stained with a unique pattern of MAbs to Mac-1 and p150,95. The data obtained by immunofluorescence was confirmed by immunoprecipitation and showed that most of the chimeric α subunits associated stably with the β subunit (FIG. 12, and data not shown). Unfortunately, not all of the chimeras were expressed in COS cells: two (X-b-M and X-b-M-a-X) were synthesized in a form that did not associate with the β subunit and were retained in the cell (data not shown), and a third (X-e-M) which showed moderate cell surface expression had an abnormal pattern of immunoprecipitation, as MAbs to the α subunit precipitated only the α chain, and MAbs to the β subunit precipitated neither the a nor β chains (data not shown).

Since we were unable to express a subset of chimeras in COS cells, we attempted to express the molecules in stable cell lines to map definitively the structural epitopes of MAbs and perform functional analyses. Chimeric a and wild type β subunits were cotransfected with the pDCHIP plasmid into CHO DG 44 cells (Qu, et al., *J. Exp. Med.* 167:1195–1210 (1988)) that lack functional dihydrofolate reductase. After drug selection, positive cells were identified, recovered by immunopanning (Aruffo et al., *Proc. Natl. Acad. Sci. USA* 84:8573–8577 (1987)), cultured, and repanned until CHO cell lines that expressed high levels of individual chimeric molecules were obtained. Flow cytometric analyses demonstrated that all of the chimeric molecules were well expressed on the surface of CHO cells (FIG. 13) and for each chimera levels of the α and β chains were equivalent (FIG. 13). In one case (M-b-X-a-M), the level of β subunit on the surface exceeded the level of α subunit. Despite expressing all of molecules on the cell surface, immunoprecipitation studies revealed an improper association between the α and β subunits in three of the chimeras. Immunoprecipitations of surface labelled X-e-M, X-b-M, and X-b-M-a-X chimeras with the β subunit MAb (TS1/18) were either weak or absent, (FIG. 14, Groups B, E, and J; Lane 3). These three chimeras apparently lost the TS1/18 epitope on the β subunit after detergent solubilization. Previously we have shown that TS1/18 immunoprecipitates LFA-1, Mac-1, and p150, 95 from αβ complexes but not from the unassociated β subunit (Springer, et al.,*J. Exp. Med.* 160:1901–1918 (1984) ). Despite the change in antigenic reactivity, the β subunit was still associated with the α subunit to some degree in these chimeras as it was coprecipitated by the α subunit specific MAbs (FIG. 14, Groups B, E, and J; Lane 2). The weakness of the association between subunits also was suggested by the change in the stoichiometry of the precipitated complex. Immunoprecipitation of X-e-M, X-b-M, and X-b-M-a-X with MAbs to the α subunit differed from the other chimeras as there was a significantly greater quantity of α subunit relative to the β subunit.

Epitope Mapping of MAbs to Mac-1

Because an improper association of α and β subunits in a subset of chimeras could affect functional assays and our subsequent analyses, we used MAbs to generate a structure-function map of the ligand binding domains on Mac-1. MAb epitopes were localized on the Mac-1 α subunit by their ability to bind to a particular subset of chimeras and the results correlated with the ability of the MAb to block distinct adhesive functions of the native Mac-1 molecule. To supplement the ten MAbs that had been previously characterized, 24 new MAbs against the α chain of Mac-1 were generated (FIG. 15) by immunization with purified Mac-1 and screening by immunofluorescent flow cytometry on neutrophils, lymphocytes, and transfected cells.

To map the structural epitopes of the 34 MAbs against the Mac-1 α subunit, the CHO cells expressing wild type and chimeric Mac-1 and p150,95 were tested for their differential ability to bind to MAbs (FIG. 13). Of the 34 MAbs examined, 19 localized to the I domain, 11 to the C-terminal region, and one (CBRM1/20) to the region containing the divalent cation binding repeats. Two MAbs (CBRM1/32 and OKM10$_{old}$ localized to a discontinuous epitope that required the presence of both the N-terminal and divalent cation binding regions. The OKM10$_{old}$ that was received from Ortho Pharmaceuticals is distinct from the OKM10$_{old}$ The new OKM10 does not block iC3b-E binding to Mac-1 as was described above and as we have verified for OKM10$_{old}$, and the two MAbs do not localize to the same region of Mac-1 (FIG. 15)).We were unable to localize the structural epitope of two MAbs (OKM10$_{new}$ and CBRM1/28). Three MAbs against the p150,95 α subunit also were mapped with the CHO cell chimeras: CBRp150/4G1 mapped to the C-terminal region, BLY6 localized to the I domain, and SHCL3 mapped to sites both in the N-terminal and divalent cation binding regions.

Inhibitory Activity of MAbs iC3b-E Binding to Mac-1

The ability to inhibit distinct Mac-1-dependent adhesive functions was investigated with the extended panel of MAbs. To test which MAbs block iC3b binding to Mac-1, a quantitative assay was developed in which FITC-labelled iC3b-erythrocytes were incubated with adherent neutrophils in the presence of MAbs to Mac-1 (FIG. 16). MAbs to the I domain inhibited iC3b-E binding to neutrophils with a mean of 72.6% ±24.9, whereas MAbs to the C-terminal blocked with a mean of 33.6% ±16.6. Eleven of nineteen MAbs that mapped to the I domain blocked strongly (>85%), whereas no MAb that localized to the C-terminal region showed greater than 60% inhibition. The one MAb (CBRM1/20) which mapped directly to the divalent cation binding region had little inhibitory effect. The two MAbs (OKM10$_{old}$ and CBRM1/32) that mapped to sites in both the N-terminal and divalent cation regions blocked 81% and 65% of the binding (FIG. 16). These results agree with previous reports that used a limited number of these MAbs to inhibit iC3b-Mac-1 interactions (Anderson, et al., *J. Immunol.* 137:15–27 (1986); Diamond, et aL., "Differential Effects on Leukocyte Functions of CD11a, CD11b, and CD18 Monoclonal Antibodies," in *Leukocyte Typing IV*, Knapp et al., eds., Oxford University, London, 570–574 (1989); Mosser, et al., *J. Cell Biol.* 116:511–520 (1992)).

Neutrophil Homotypic Adhesion

Several groups have demonstrated that activated neutrophils bind homotypically, and that this aggregation response is blocked by MAbs to the α or β chains of Mac-1 (Anderson, et al.,*J. Immunol.* 137:15–27 (1986); Buyon, et al., *J. Immunol.* 140:3156–3160 (1988); Patarroyo, et al., *Scand. J. Immunol.* 22:171–182 (1985)). The ligand on neutrophils for Mac-1 that mediates homotypic aggregation remains uncharacterized. To determine the regions of Mac-1 that were important for neutrophil homotypic adhesion, we tested the panel of MAbs for their ability to inhibit this interaction in a newly developed Coulter counter assay (see Methods). This assay which counts the number of particles is more stringent than the classical aggregometry assay; MAbs that inhibit in this assay by 20–30% such as CBRM1/2 and Mn41 (FIG. 16) show 56 and 67% inhibition in the light scattering aggregometry assay (FIG. 17). MAbs to the I domain blocked the aggregation assays with a mean of 25.9% ±16.1, whereas MAbs to the C-terminal region blocked with a mean of 1.8% ±1.1. Two MAbs (LPM19c and CBRM1/29) to the I domain blocked neutrophil homotypic adhesion strongly by 81% and 51%. The CBRM1/32 MAb to the N-terminal and divalent cation binding regions blocked 21%, and the CBRM1/20 MAb to the divalent cation binding region inhibited 7%.

Neutrophil Adhesion to Purified Fibrinogen

When neutrophils are stimulated with fMLP ($10^{-7}$M) they bind to fibrinogen in an almost exclusively Mac-1-dependent manner. MAbs to the I domain of Mac-1 inhibited binding to fibrinogen strongly (FIG. 16) with an average 77.6% ±13.2, whereas MAbs to the C-terminal region inhibited binding weakly with an average of 5.4% ±22.1. One MAb (CBRM1/32) which mapped outside the I domain to sites in both the N-terminal and divalent cation regions blocked binding to fibrinogen (85%). None of the MAbs against p150,95 that were examined (FIG. 16, and data not shown) inhibited binding to fibrinogen of neutrophils that were stimulated with fMLP.

ICAM-1+ L Cell Adhesion to Purified Mac-1

Neutrophils that are stimulated with fMLP use Mac-1 and LFA-1 cooperatively to bind to ICAM-1 (Diamond et al., *Cell* 65:961–971 (1991); Smith, et al., *J. Clin. Invest.* 83:2008–2017 (1989)). To identify blocking MAbs more easily, we switched to an assay that examined Mac-1 interaction with ICAM-1 exclusively: ICAM-1+ L cell adhesion to purified Mac-1 (Diamond, et al., *J. Cell Biol.* 111:3129–3139 (1990)). MAbs to the I domain inhibited binding with an average of 82.4% ±26.1, whereas MAbs to the C-terminal region inhibited by an average of 24.1% ±26.8 (FIG. 16). 12 of the 19 I domain MAbs inhibited by greater than 90%, whereas the strongest inhibition by a MAb to the C-terminal region was 52%. One MAb which mapped to the sites in both the N-terminal and divalent cation regions inhibited binding strongly (CBRM1/32, 97% reduction). The one MAb (CBRM1/20) that bound directly to the divalent cation binding region did not block ICAM-1 binding to Mac-1.

Functional Studies With Mac-1/p150,95 Chimeras

To examine whether the I domain of Mac-1 was essential for ligand recognition, we tested the CHO cell chimeras for their ability to bind ICAM-1 and iC3b-E. Because control transfected or untransfected CHO cells bound constitutively to fibrinogen, this ligand was not tested.

The transfected CHO cells contained a functional form of Mac-1 as stimulation with phorbol esters prompted Mac-1 transfectants to bind to purified ICAM-1 (FIG. 18A). In contrast to previous studies with transfected COS cells (Diamond, et al., *J. Cell Biol.* 111:3129–3139 (1990)), little binding to ICAM-1 was observed in the absence of stimulation (data not shown). Two chimeras (M-a-X, M-b-X) which contained the I domain of Mac-1 bound to ICAM-1, but more weakly than anticipated. Unexpectedly, the CHO cells that expressed wild type p150,95 also bound to ICAM-1. Despite the low level of binding, it was reproducible, inhibited by MAbs to p150,95, and not observed with control CHO cells transfected with ICAM-1 (FIG. 18A, and data not shown). Although we are uncertain of the physiologic relevance of this p150,95-ICAM-1 interaction, p150, 95 acts as a counter-receptor for an uncharacterized adhesion molecule on stimulated endothelial cells (Stacker et a., *J. Immunol.* 146:648–655 (1991)c), and L cell transfectants that express ICAM-1 bind weakly to purified p150,95 (Stacker and Springer, unpublished data). Chimeras in which the I domains of Mac-1 and p150,95 were exchanged (M-e-X-b-M, X-e-M-b-X) showed no significant difference in adhesion to ICAM-1. Although both wild type Mac-1 and p150,95 transfectants adhered to ICAM-1, three chimeras (X-e-M, X-b-M, X-b-M-a-X), did not bind to ICAM-1; these three chimeras, however, were expressed improperly on COS and CHO cells (see above). Thus, despite expression of all of the chimeras at relatively high levels on CHO cells, no readily interpretable pattern of binding to ICAM-1 was observed.

We tested the CHO cell transfectants for their ability to bind iC3b-E coated erythrocytes. Almost all of the CHO cells expressing wild type Mac-1 rosetted with iC3b-E (FIG. 18B). Although the binding occurred in the absence of stimulation, the average number of iC3b coated particles per cell increased after phorbol ester treatment (data not shown, and Diamond, Mosser, and Springer, unpublished data). The pattern of binding of iC3b-E to the Mac-1/p150,95 chimeras again did not localize the binding region definitively (FIG. 18B). The three chimeras (X-e-M, X-b-M, X-b-M-a-X) that were not expressed properly in COS and CHO cells and did not bind to ICAM-1 in CHO cells, failed to rosette with iC3b-E. Four chimeras that contained the I domain of Mac-1 (M-b-X, M-a-X, X-e-M-b-X, and M-b-X-a-M) rosetted with iC3b-E, but at significantly lower levels than wild type Mac-1 despite similar expression levels. Unexpectedly, one chimera (M-e-X-b-M) which contained the I domain of p150,95 bound iC3b consistently. In independent studies with transfected COS cells, we observed that the same subset of chimeras rosetted with iC3b-E (data not shown).

DISCUSSION

In this report, using chimeras of Mac-1 and p150,95, we localized the epitopes for 34 MAbs to Mac-1 and correlated this with their ability to block distinct adhesive functions of the native Mac-1 molecule. We find that the 200 amino acid I domain on the α subunit of Mac-1 is a major site of ligand recognition for iC3b, ICAM-1, fibrinogen, and the undefined counter-receptor for neutrophil aggregation. One MAb (CBRM1/32) that mapped outside the I domain to an epitope shared by the N-terminal and divalent cation binding regions also blocked binding to iC3b, ICAM-1 and fibrinogen. Thus, the N-terminal and perhaps divalent cation binding regions may contribute to recognition of several of the ligands. MAb epitopes were used to localize the ligand recognition sites because interpretation of the results from functional assays with the Mac-1/p150,95 chimeras was not straightforward.

The I domain appears important in the recognition of all four ligands by Mac-1 because in each of the experimental systems tested, several different MAbs that mapped to the I domain blocked Mac-1-dependent binding strongly (>80%). Furthermore, in all cases, the individual MAb that abrogated binding most completely mapped to the I domain. Two-thirds of the MAbs that mapped to the I domain blocked Mac-1 interaction with iC3b, fibrinogen, and ICAM-1 by greater than 70%, and all of the MAbs that blocked neutrophil homotypic adhesion strongly, mapped to the I domain.

While the majority of MAbs to the I domain were strongly inhibitory in at least one of the assays, not all of the MAbs were able to block several ligand interactions. For example, only five MAbs (LPM19c, TMG-65, Mn41, CBRM 1/29, CBRM 1/34) blocked all Mac-1-ligand interactions strongly. Many of the MAbs that blocked binding to fibrinogen, ICAM-1 and iC3b, only partially inhibited neutrophil homotypic adhesion. There were, however, several exceptions. Two MAbs (OKM9 and CBRM1/27) blocked binding to fibrinogen binding strongly but inhibited interactions with the other three ligands only weakly, whereas three MAbs (CBRM1/1, CBRM1/2, CBRM1/32) that blocked adhesion to fibrinogen and ICAM-1 inhibited binding to iC3b only partially. The differences in patterns of inhibition among MAbs that map to the I domain suggest the presence of several immunoreactive and functional subdomains. For each individual ligand, some or all of these subdomains may contribute to the architecture of the binding site. Thus, we speculate that the ligand recognition sites within the I domain are not identical, but are overlapping.

Despite screening for new MAbs to Mac-1 only by their ability to bind to peripheral blood neutrophils, the majority of new MAbs mapped to the I domain. This was unanticipated because the α subunits of human and murine Mac-1 are 74% identical at the amino acid level (Arnaout, et al., *J. Cell Biol.* 106:2153–2158 (1988); Corbi, et al., *J. Biol. Chem.* 263:12403–12411 (1988); Pytela, *EMBO J.* 7:1371–1378 (1988)), with the divalent cation region showing the greatest identity (84%) and the C-terminal region the least identity (74%) among extracellular domains. It is not clear why the I domain is immunodominant; it is more homologous (81% identity) and smaller in size (200 compared to 500 amino acids) than the C-terminal region. Not surprisingly, the strong identity between I domains of murine and human Mac-1 conserves sites of ligand recognition as both species of Mac-1 bind to human and murine iC3b coated particles (Beller, et al., *J. Exp. Med.* 156:1000–1009 (1982)) and to COS cells transfected with murine ICAM-1 (Diamond, et al. unpublished).

While the homology between human Mac-1 and p150,95 is significantly lower than murine and human Mac-1, the residues that confer ligand specificity appear to be conserved. Human Mac-1 and p150,95 have a 63% overall protein sequence identity with a 55% identity between corresponding I domains (Corbi, et al., *J. Biol. Chem.* 263:12403–12411 (1988); Corbi, et al., *EMBO J.* 6:4023–4028 (1987)). None of the MAbs studied cross react between the α subunits of Mac-1 and p150,95. However, increasing experimental evidence suggests that this degree of conservation is sufficient to conserve sites of ligand recognition as p150,95 binds to a similar repertoire of ligands as Mac-1 including fibrinogen (Loike, et al., *Proc. Natl. Acad. Sci. USA* 88:1044–1048 (1991); Postigo, et al., *J. Exp. Med.* 174:1313–1322 (1991)) and iC3b (Micklem et al., *Biochem. J.* 231:233–236 (1985); Myones, et al., *J. Clin. Invest.* 82:640–651 (1988); Ross, et al., *J. Leukoc. Biol.* 51:109–117 (1992)). LFA-1 and Mac-1, which are 36% identical at the amino acid level share ICAM-1 as a ligand, although the binding appears distinct as LFA-1 binds to the first Ig-like domain (Staunton, et al., *Cell* 61:243–254 (1990)) and Mac-1 binds to the third Ig-like domain on ICAM-1 (Diamond, et al., *Cell* 65:961–971 (1991)). More refined mutagenesis studies are required to determine whether Mac-1, p150,95, and LFA-1 utilize related recognition sites to bind their shared ligands.

MAbs that mapped to the 493 amino acid C-terminal region showed little capacity to block any of the ligand interactions with Mac-1. The average inhibition ranged from a low of 1.8% for neutrophil homotypic adhesion to a high of 33.6% for binding to iC3b. Thus, we suggest that the C-terminal region of Mac-1 does not contain recognition sites that are critical for a direct interaction with any of the four ligands examined.

Because we generated only one MAb that mapped to the 362 amino acid region that contained the 294 amino acid divalent cation binding repeats and the 68 amino acids immediately N-terminal to them, little conclusive statement can be made about the role of this part of the molecule in ligand recognition. The apparent lack of immunogenicity may be attributed, in part, to the 84% amino acid conservation between the corresponding regions of human and murine Mac-1. The one MAb that localized strictly to this region, CBRMM1/20, did not block adhesion in any of the assays by greater than 30%. However, we cannot exclude the existence of recognition sites that were not blocked by CBRM1/20. Indeed, experiments (D'Souza, *J. Biol. Chem.* 265:3440–3446 (1990); D'Souza, *Nature* 350:66–68 (1991)) suggest that the related platelet integrin $\alpha_{IIb}\beta_3$ uses a site within the divalent cation binding repeats to bind to fibrinogen. Future studies with additional MAbs to this region are required to clarify whether the strong sequence conservation among divalent cation binding modules maintains receptor conformation or sustains a direct interaction with ligand.

Although we did not successfully map any of the MAbs to the N-terminal region exclusively, two MAbs to Mac-1 (OKM10$_{old}$ and CBRM1/32) and one MAb to p150,95 (SHCL3) bound to discontinuous epitopes that required the presence of both the N-terminal and divalent cation binding regions of Mac-1 or p150,95. SHCL3 differed from CBRM1/32 and OKM10$_{old}$ as it bound to chimeras that contained only the N-terminus of p150,95; however, it bound more strongly when both the N-terminus and divalent cation binding region of p150,95 were present. Importantly, these MAbs were the only ones that mapped outside the I domain and blocked ligand interaction strongly. CBRM1/32 blocked (70–95%) binding to iC3b, fibrinogen, and ICAM-1, and OKM10$_{old}$ blocked binding to iC3b (FIG. 14 and Anderson, et al., *J. Immunol.* 137:15–27 (1986); Wright, et al., *Proc. Natl. Acad. Sci. USA* 80:5699–5703 (1983)), and inhibits binding to fibrinogen (Wright, et al., *Proc. Natl. Acad. Sci. USA* 85:7734–7738 (1988)). SHCL3 blocks binding of p150,95 to stimulated endothelial cells (Stacker et al., *J. Immunol.* 146:648–655 (1991)) and iC3b (Bilsland, Diamond, Mosser, and Springer, unpublished observations), but not to fibrinogen (Postigo, et al., *J. Exp. Med.* 174:1313–1322 (1991)). The mapping of three MAbs to discontinuous regions of the α chain provides immunological evidence for associations between the N-terminus and the divalent cation binding regions, which are separated by the 200 amino acids of the I domain. Previous electron microscopy studies on the related integrins $\alpha_{IIb}\beta_3$ and $\alpha_5\beta_1$ have shown that the α and β subunits form a globular head at the N-terminal edge of the molecule that is distal to the membrane spanning region (Carrell, *J. Biol. Chem.* 260:1743–1749 (1985); Hynes, *Cell* 69:11–25 (1992); Nermut, et al., *EMBO J.* 7:4093–4099 (1988)). The associations from disparate regions of Mac-1 and p150,95 suggests that the I domain does not intercalate into the globular head to form a string of physically autonomous modules. The structure of the leukocyte integrins thus differs from the linear array of domains that is proposed for members of the immunoglobulin and selectin families of adhesion molecules (Bevilacqua, et al., *Science* 243:1160–1165 (1989); Driscoll, et al., *Nature* 353:762–765 (1991); Kansas, et al., *J. Cell. Biol.* 114:351–358 (1991); Williams et al., *Annu. Rev. Immunol.* 6:381405 (1988)).

Although the experiments with MAbs indicate that the I domain is a primary ligand recognition site, no discernible pattern was observed when the Mac-1/p150,95 chimeras were tested in functional assays. Several factors may have contributed to the failure of these experiments to map directly the ligand binding sites on Mac-1 for iC3b and ICAM-1. As suggested above, others have recently demonstrated that Mac-1 and p150,95 appears to bind to some of the same ligands. Attempts to generate Mac-1/LFA-1 chimeras which have less overlap in ligand repertoire were unsuccessful as these molecules after transfection into COS cells were synthesized in precursor form, but were not expressed on the surface. Although others have reported complement receptor activity for p150,95 (Micklem et al., *Biochem. J.* 231:233–236 (1985); Myones, et al., *J. Clin. Invest.* 82:640–651 (1988); Ross, et al., *J. Leukoc. Biol.* 51:109–117 (1992)), in our experiments, iC3b coated erythrocytes did not bind to transfected CHO cells expressing p150,95 (FIG. 16B, and data not shown). Possibly, in the transfected cells, the I domain of p150,95 may contain the structural information to bind iC3b but lack proper interactions with other parts of the α or β subunits. In favor of this, a human-chicken p150,95 hybrid molecule that was comprised of a human $\alpha^x$ subunit and chicken $\beta_2$ subunit and expressed in COS cells rosetted strongly with iC3b-E although the human $\alpha^x$ that was paired with the human $\beta_2$ subunit did not (Bilsland and Springer, unpublished observations). Our experiments also suggest that at least in vitro, p150,95 binds weakly to ICAM-1 (FIG. 16A). The I domain of p150,95 in the context of a wild type p150,95 frame bound to ICAM-1 poorly, but in the context of a Mac-1 frame (M-e-X-b-M) where secondary sites may be present, the binding to ICAM-1 was enhanced.

The analysis of the functional assays with the chimeras was complicated also by the improper expression or association with the β subunit by three of the chimeric α subunits (X-e-M, X-b-M, X-b-M-a-X) in COS and CHO cells. Immunoprecipitations of surface labelled CHO cell transfectants expressing these three chimeras with the β subunit MAb (S1/18) were either weak or absent although the β subunit was still associated with the (x subunit as it was coprecipitated by the α subunit specific MAbs. In light of this, it is not surprising that X-e-M, X-b-M, and X-b-M-a-X did not bind to iC3b or ICAM-1 when expressed in CHO or COS cells. Two other chimeras (M-a-X and M-b-X) that contained the I domain of Mac-1 and bound to ICAM-1 and iC3b poorly, show evidence of subtle structural anomalies based on changes in antigenic reactivity. M-a-X and M-b-X show a reduction or loss of binding to two MAbs that map to the I domain, CBRM1/2 (FIG. 15) and CBRM1/5 (Diamond and Springer, submitted). It is noteworthy that CBRM1/15 recognizes a subpopulation of functionally active Mac-1 molecules on neutrophils and monocytes (Diamond and Springer, submitted), and is expressed on other chimeras (X-e-M-b-X, M-b-X-a-M) that contain the I domain of Mac-1 and bind ligand (data not shown). Thus, despite the high levels of expression in CHO cells, M-a-X and M-b-X may not be in a conformation that sustains ligand binding; the molecular packing of the I domain may be disrupted sufficiently by the improper context of surrounding domains so that it is unable to recognize ligand. On leukocytes, to recognize ligands, Mac-1 and LFA-1 must convert from a low avidity to high avidity state (Buyon, et al., *J. Immunol.* 140:3156–3160 (1988); Dustin et al. *Nature* 341:619–624 (1989); Lo, et al., *J. Exp. Med.* 169:1779–1793 (1989); van Kooyk, et al., *Nature* 342:811–813 (1989)). It is tempting to speculate that integrins require a physical "opening or closing" of the molecule that enables ligand binding and that the juxtaposition of homologous, but non-native domains in some of the chimeras prevents this change from occurring. Moreover, the β subunit could modulate the structural change in the α subunit. This could explain why deletion or substitution of residues in the cytoplasmic domain of the β subunit abolishes LFA-1 binding to ICAM-1 (Hibbs, et al., *J. Exp. Med.* 174:1227–1238 (1991); Hibbs, et al., *Science* 251:1611–1613 (1991)), why X-e-M, X-b-M, and X-b-M-a-X do not bind to iC3b and ICAM-1, or why a chicken but not human $\beta_2$ subunit allows p150,95 to rosette with iC3b coated particles.

In summary, the studies presented here demonstrate that the I domain on Mac-1 is a major recognition site for both its cellular and soluble ligands. This is the first study to provide a definitive role of the I domain on integrin α subunits. Previously, because of its homology to the ligand binding regions in von Willebrand factor, cartilage matrix protein, and complement proteins, the evolutionarily inserted I domain has been speculated to be important in ligand recognition (Larson, et al., *J. Cell Biol.*108:703–712 (1989); Pytela, *EMBO J*. 7:1371–1378 (1988)).

What is claimed is:

1. An antibody, an antigen binding antibody fragment, or an antigen binding antibody derivative, wherein said antibody, said antigen binding antibody fragment, and said antigen binding antibody derivative, blocks Mac-1/ligand interaction by selectively binding to activated Mac-1 present on stimulated myeloid cells, antibody, wherein said said antigen binding antibody fragment, and said antigen binding antibody derivitive, selectively bind to the same subpopulation of said activated Mac-1 molecules as that bound by the antibody produced by a hybridoma selected from the group consisting of ATCC Deposit HB11460 and ATCC Deposit HB11461.

2. The antibody, antigen binding antibody fragment, and the antigen binding antibody derivative of claim 1 wherein said antibody said antigen binding antibody fragment, and said antigen binding antibody derative selectively bind to said activated Mac-1, and block the binding of said stimulated myeloid cell to ICAM-1.

3. The antibody, antigen binding antibody fragment, or antigen binding antibody derivative of claim 1 wherein said antibody, said antigen binding antibody fragment, and said antigen binding antibody derivative, competitively bind with antibody produced by a hybridoma selected from the group consisting of ATCC Deposit HB11460 and ATCC Deposit HB11461 for activated Mac-1 present on stimulated myeloid cells.

4. An anti-Mac-1 antibody, wherein said antibody is CBRM 1/5 obtainable from ATCC Deposit HB11460.

5. An anti-Mac-1 antibody, wherein said antibody is CBRM 1/19 obtainable from ATCC Deposit HB11461.

* * * * *

UNITED STATES PATENT AND TRADEMARK OFFICE
CERTIFICATE OF CORRECTION

PATENT NO. : 5,877,295

DATED : March 2, 1999

INVENTORS : DIAMOND AND SPRINGER

It is certified that an error appears in the above-identified patent and that said Letters Patent is hereby corrected as shown below.

In column 44, Claim 1, line 6, please delete "antibody, wherein said said" and insert therein --wherein said antibody, said--.

Signed and Sealed this

Twenty-first Day of September, 1999

Attest:

Q. TODD DICKINSON

*Attesting Officer*  *Acting Commissioner of Patents and Trademarks*